United States Patent

Nagasawa et al.

[11] Patent Number: 5,981,557
[45] Date of Patent: Nov. 9, 1999

[54] AMINOTHIAZOLE DERIVATIVE, MEDICAMENT CONTAINING THE SAME, AND INTERMEDIATE FOR PREPARATION OF SAID COMPOUND

[75] Inventors: Masaaki Nagasawa; Masakazu Murata; Hiroyasu Nishioka; Tadashi Kurimoto; Shigeru Ueki; Osamu Kitagawa, all of Konan-machi, Japan

[73] Assignee: Zeria Pharmaceutical Co., Ltd., Tokyo, Japan

[21] Appl. No.: 08/952,106

[22] PCT Filed: May 16, 1996

[86] PCT No.: PCT/JP96/01297

§ 371 Date: Nov. 18, 1997

§ 102(e) Date: Nov. 18, 1997

[87] PCT Pub. No.: WO96/36619

PCT Pub. Date: Nov. 21, 1996

Related U.S. Application Data

[30] Foreign Application Priority Data

May 18, 1995 [JP] Japan ..................................... 7-142399

[51] Int. Cl.$^6$ ........................ C07D 277/56; A61K 31/425
[52] U.S. Cl. ............................................ 514/365; 548/195
[58] Field of Search .............................. 548/195; 514/371

[56] References Cited

U.S. PATENT DOCUMENTS 5,510,478  4/1996  Sabb ........................ 548/195
5,712,270  1/1998  Sabb ........................ 548/195

*Primary Examiner*—Robert Gerstl
*Attorney, Agent, or Firm*—Oblon, Spivak, McClelland, Maier & Neustadt, P.C.

[57] ABSTRACT

The present invention relates to an aminothiazole derivative represented by the following formula (I):

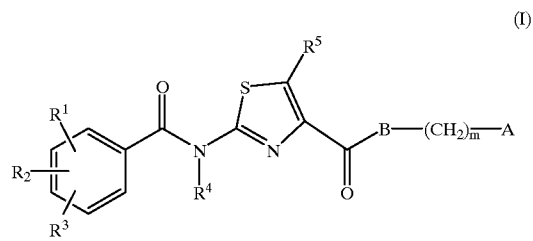

wherein $R^1$, $R^2$ and $R^3$ each independently represents a hydrogen atom, a hydroxy group, a lower alkyl group, a lower alkoxy group or the like; $R^4$ represents a hydrogen atom or a lower alkyl group; $R^5$ represents a hydrogen atom, a halogen atom or a lower alkyl group; m stands for an integer of 0 to 4, A represents a substituted amino group, a substituted imino group, a heterocyclic group or the like; and B stands for an imino group or an oxygen atom, a medicament containing it and an intermediate for the preparation of said compound. The compound has strong restoration effects on dysmotility in the gastrointestinal tract and at the same time has high safety so that it is useful as an excellent gastroprokinetic.

12 Claims, No Drawings

AMINOTHIAZOLE DERIVATIVE, MEDICAMENT CONTAINING THE SAME, AND INTERMEDIATE FOR PREPARATION OF SAID COMPOUND

This application is a 371 of PCT/JP96/01297 filed May 16, 1996.

TECHNICAL FIELD

The present invention relates to a novel aminothiazole derivative having improving effects on the dysmotility in the gastrointestinal tract, a medicament containing the derivative and an intermediate for preparing said compound.

BACKGROUND ART

As a therapeutic agent for gastrointestinal dysmotility, dopamine antagonists such as domperidone and metoclopramide, opioate agonists such as trimebutine maleate, 5-$HT_3$ antagonists/5-$HT_4$ agonists such as cisapride, acetylcholine agonists such as acetylcholine chloride and the like have conventionally been provided for clinical use. In addition to them, a number of prokinetics have been studied with a view to treating gastrointestinal dysmotility (Japanese Patent Applications Laid-Open Nos. HEI 1-313424, HEI 3-163074 and HEI 4-279581). These agents, however, do not always bring about sufficient effects for the improvement of dysmotility. There is a potential problem that side effects may possibly occur owing to the acting mechanism of the agent even if it has sufficient effects. So, the above-described agents are not completely satisfactory. Accordingly, there is a demand for the development of a medicament having excellent improving effects on gastrointestinal dysmotility and having less side effects.

DISCLOSURE OF THE INVENTION

With the forgoing in view, the present inventors have carried out an extensive investigation. As a result, it has been found that a specific aminothiazole derivative has excellent improving effects on gastrointestinal dysmotility and also has less side effects, leading to the completion of the present invention.

The present invention therefore provides an aminothiazole derivative represented by the following formula (I):

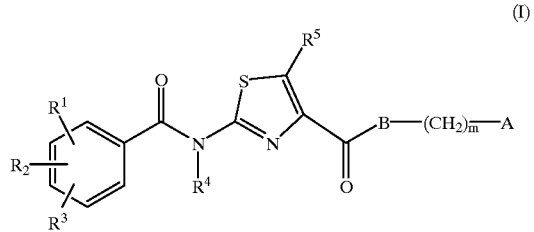

wherein $R^1$, $R^2$ and $R^3$ are the same or different and each independently represents a hydrogen atom, a hydroxy group, a lower alkyl group, a lower alkoxy group, a lower alkylcarbonyloxy group, a halogen atom, a nitro group, an amino group, a mono- or di-(lower alkyl)amino group, a mono- or di-(lower alkyl)carbonylamino group, a formylamino group, a mono- or di-(lower alkyl)aminoalkylamino group, or $R^1$ and $R^2$ may be coupled together to form a methylenedioxy group; $R^4$ represents a hydrogen atom or a lower alkyl group; $R^5$ represents a hydrogen atom, a halogen atom or a lower alkyl group; A represents a group represented by the following formula:

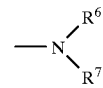

wherein $R^6$ and $R^7$ are the same or different and each independently represents a hydrogen atom, a lower alkyl group, a lower alkoxy group, a hydroxy(lower alkyl) group, a carboxy(lower alkyl) group, a (lower alkoxy)carbonyl (lower alkyl) group, a lower alkoxyalkyl group, a mono- or di-(lower alkyl)aminoalkyl group, a phenylalkyl group which may be substituted with one or two lower alkoxy groups on the benzene ring, a saturated or unsaturated nitrogen-containing heterocyclic group which may be substituted by a lower alkyl group, or $R^6$ and $R^7$, together with an adjacent nitrogen atom, form a saturated or unsaturated nitrogen-containing heterocyclic group which may be substituted by an oxo group (O=) or 1 to 3 lower alkyl or hydroxy(lower alkyl) groups, or a group represented by the following formula:

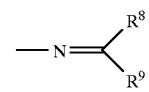

wherein $R^8$ and $R^9$ are the same or different and each independently represents an amino group, a mono- or di-(lower alkyl)amino group, a mercapto group or a lower alkylthio group, or $R^8$ and $R^9$, together with the adjacent carbon atom, form a nitrogen-containing heterocyclic group; and B represents an imino group which may be substituted by a lower alkyl group or an oxygen atom; and m stands for an integer of 0 to 4; B—$(CH_2)_m$—A may form a piperidinyl, branched alkylamino or phenylamino group which may be substituted by a mono- or di-(lower alkyl)amino group, or a piperazinyl, piperidinylamino or piperidinylalkylamino group which may be substituted by a lower alkyl group, or a salt thereof.

The present invention also provides a medicament comprising as an effective ingredient the above-described aminothiazole derivative (I) or salt thereof.

The present invention further provides a pharmaceutical composition comprising the above-described aminothiazole derivative (I) or salt thereof and a pharmaceutically-acceptable carrier.

The present invention still further provides the use of the above-described aminothiazole derivative (I) or salt thereof as a medicament.

The present invention still further provides a prevention and treatment method for the diseases caused by digestive dyskinesia, which comprises administering an effective amount of the above-described aminothiazole derivative (I) or salt thereof to a patient.

The present invention still further provides a thiazole derivative represented by the following formula (II):

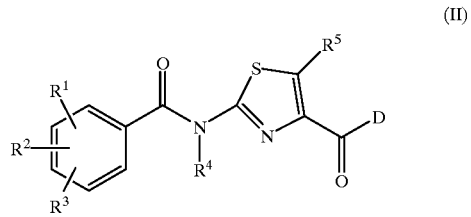

wherein $R^1$, $R^2$, $R^3$, $R^4$ and $R^5$ have the same meanings as defined above, and D represents a hydroxy or a lower alkoxy group or salt thereof which is useful as an intermediate for the preparation of the invention compound (I).

BEST MODES FOR CARRYING OUT THE INVENTION

The term "lower" as used herein means a linear, branched or cyclic carbon chain having 1 to 6 carbon atoms.

Accordingly, examples of the "lower alkyl group" include linear, branched or cyclic alkyl groups having 1 to 6 carbon atoms (which may hereinafter be abbreviated as "$C_{1-6}$ alkyl") such as methyl, ethyl, propyl, isopropyl, cyclopropyl, butyl, isobutyl, sec-butyl, tert-butyl, cyclobutyl, pentyl, 1-methylbutyl, 2-methylbutyl, isopentyl, tert-pentyl, 1,2-dimethylpropyl, neopentyl, 1-ethylpropyl, cyclopentyl, hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methyl-1-ethylpropyl, 1-ethyl-2-methylpropyl, 1,1,2-trimethylpropyl, 1,2,2-trimethylpropyl and cyclohexyl. Among them, preferred are linear or branched $C_{1-4}$ alkyl groups.

Examples of the "lower alkoxy group" include linear, branched or cyclic alkoxy groups having 1 to 6 carbon atoms (which may hereinafter be abbreviated as "$C_{1-6}$ alkoxy") such as methoxy, ethoxy, propoxy, cyclopropoxy, isopropoxy, butoxy, isobutoxy, sec-butoxy, tert-butoxy, cyclobutoxy, pentyloxy, 1-methylbutoxy, 2-methylbutoxy, isopentyloxy, tertpentyloxy, 1,2-dimethylpropoxy, neopentyloxy, 1-ethylpropoxy, cyclopentyloxy, hexyloxy, 1-methylpentyloxy, 2-methylpentyloxy, 3-methylpentyloxy, isohexyloxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-methyl-1-ethylpropoxy, 1-ethyl-2-methylpropoxy, 1,1,2-trimethylpropoxy, 1,2,2-trimethylpropoxy and cyclohexyloxy. Among them, preferred are linear or branched $C_{1-4}$ alkoxy groups.

The term "halogen atom" as used herein means a fluorine, chlorine, bromine or iodine atom.

The term "lower alkylcarbonyl group" means a linear, branched or cyclic $C_{2-7}$ alkylcarbonyl group, while the term "lower alkylcarbonyloxy group" means a linear, branched or cyclic $C_{2-7}$ alkylcarbonyloxy group. Here, those exemplified above as the "lower alkyl group" can also be given as the examples of the lower alkyl portion of the lower alkylcarbonyl or lower alkylcarbonyloxy group. Preferred examples of the alkylcarbonyl group include acetyl, propionyl, butyryl and valeryl groups, while preferred examples of the alkylcarbonyloxy group include acetyloxy, propionyloxy, butyryloxy and valeryloxy groups.

The term "hydroxy(lower alkyl) group" means a linear, branched or cyclic $C_{1-6}$ hydroxyalkyl group. Examples include hydroxymethyl, 1-hydroxyethyl, 2-hydroxyethyl, 1-hydroxypropyl, 2-hydroxypropyl, 3-hydroxypropyl, 1-hydroxy2-methylethyl, 1-hydroxycyclopropyl, 2-hydroxycyclopropyl, 1-hydroxybutyl, 2-hydroxybutyl, 3-hydroxybutyl, 4-hydroxybutyl, 2-hydroxy-2-methylpropyl, 1-hydroxy-2,2-dimethylethyl, 1-hydroxy-1,2-dimethylethyl, 1-hydroxypentyl, 2-hydroxypentyl, 3-hydroxypentyl, 4-hydroxypentyl, 5-hydroxypentyl, 2-hydroxy-2-methylbutyl, 3-hydroxy-2-methylbutyl, 4-hydroxy-2-methylbutyl, 2-hydroxy-3-methylbutyl, 3-hydroxy-3-methylbutyl, 4-hydroxy-3-methylbutyl, 2-hydroxy4-methylbutyl, 3-hydroxy-4-methylbutyl, 4-hydroxy-4-methylbutyl, 1-hydroxycyclopentyl, 2-hydroxycyclopentyl, 3-hydroxycyclopentyl, 1-hydroxyhexyl, 2-hydroxyhexyl, 3-hydroxyhexyl, 4-hydroxyhexyl, 5-hydroxyhexyl, 6-hydroxyhexyl, 2-hydroxy-2-methylpentyl, 2-hydroxy-3-methylpentyl, 2-hydroxy-4-methylpentyl, 2-hydroxy-5-methylpentyl, 3-hydroxy-2-methylpentyl, 3-hydroxy-3-methylpentyl, 3-hydroxy-4-methylpentyl, 3-hydroxy-5-methylpentyl, 4-hydroxy-2-methylpentyl, 4-hydroxy-3-methylpentyl, 4-hydroxy-4-methylpentyl, 4-hydroxy-5-methylpentyl, 5-hydroxy-2-methylpentyl, 5-hydroxy-3-methylpentyl, 5-hydroxy-4-methylpentyl, 5-hydroxy-5-methylpentyl, 1-hydroxycyclohexyl, 2-hydroxycyclohexyl, 3-hydroxycyclohexyl and 4-hydroxycyclohexyl groups. Among them, linear or branched $C_{1-4}$ hydroxyalkyl groups are particularly preferred.

The term "mono- or di-(lower alkyl)amino group" means an amino group substituted by one or two linear, branched or cyclic $C_{1-6}$ alkyl groups. Examples include methylamino, ethylamino, propylamino, isopropylamino, cyclopropylamino, butylamino, isobutylamino, sec-butylamino, tert-butylamino, cyclobutylamino, pentylamino, 1-methylbutylamino, 2-methylbutylamino, isopentylamino, tert-pentylamino, 1,2-dimethylpropylamino, neopentylamino, 1-ethylpropylamino, cyclopentylamino, hexylamino, 1-methylpentylamino, 2-methylpentylamino, 3-methylpentylamino, isohexylamino, 1-ethylbutylamino, 2-ethylbutylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-methyl-1-ethylpropylamino, 1-ethyl-2-methylpropylamino, 1,1,2-trimethylpropylamino, 1,2,2-trimethylpropylamino, cyclohexylamino, dimethylamino, diethylamino, dipropylamino, diisopropylamino, dibutylamino, diiobutylamino, methylethylamino, methylpropylamino, methylisopropylamino, methylbutylamino, ethylpropylamino, ethylisopropylamino, ethylbutylamino, propylisopropylamino, propylbutylamino and isopropylbutylamino groups. Among them, amino groups each substituted by one or two linear or branched $C_{1-4}$ alkyl groups are preferred.

The "mono- or di-(lower alkyl)carbonylamino group" means an amino group substituted by one or two linear, branched or cyclic $C_{2-7}$ alkylcarbonyl groups. Examples include acetylamino, propionylamino, butyrylamino, isobutyrylamino, cyclopropylcarbonylamino, valerylamino, isovalerylamino, sec-butylcarbonylamino, pivaroylamino, cyclobutylcarbonylamino, pentylcarbonylamino, 1-methylbutylcarbonylamino, 2-methylbutylcarbonylamino, isopentylcarbonylamino, tert-pentylcarbonylamino, 1,2-dimethylpropylcarbonylamino, neopentylcarbonylamino, 1-ethylpropylcarbonylamino, cyclopentylcarbonylamino, hexylcarbonylamino, 1-methylpentylcarbonylamino, 2-methylpentylcarbonylamino, 3-methylpentylcarbonylamino, isohexylcarbonylamino, 1-ethylbutylcarbonylamino, 2-ethylbutylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-methyl-1-ethylpropylcarbonylamino, 1-ethyl-2-methylpropylcarbonylamino, 1,1,2-trimethylpropylcarbonylamino, 1,2,2-trimethylpropylcarbonylamino, cyclohexylcarbonylamino, diacetylamino, dipropionylamino, dibutyrylamino, diisobutyrylamino, divalerylamino, diisovalerylamino, acetylpropionylamino, acetylbutyrylamino, acetylisobutyrylamino, acetylvalerylamino, propionylbutyrylamino, propionyliosobutyrylamino, propionylvalerylamino, butyrylisobutyrylamino, butyrylvalerylamino and isobutyrylvalerylamino groups. Among them, amino groups each substituted by one or two linear or branched $C_{2-5}$ alkyl groups are particularly preferred.

Examples of the "lower alkoxyalkyl group" include $C_{1-6}$ alkoxy ($C_{1-6}$ alkyl) groups such as methoxymethyl, ethoxymethyl, propoxymethyl, isopropoxymethyl, butoxymethyl, isobutoxymethyl, sec-butoxymethyl, tert-butoxymethyl, cyclopropoxymethyl, pentyloxymethyl, isopentyloxymethyl, hexyloxymethyl, isohexyloxymethyl, cyclopentyloxymethyl, cyclohexyloxymethyl, methoxyethyl, ethoxyethyl, propoxyethyl, isopropoxyethyl, butoxyethyl, isobutoxyethyl, sec-butoxyethyl, tert-butoxyethyl, cyclopropoxyethyl, pentyloxyethyl, isopentyloxyethyl, hexyloxyethyl, isohexyloxyethyl, cyclopentyloxyethyl, cyclohexyloxyethyl, methoxypropyl, ethoxypropyl, propoxypropyl, isopropoxypropyl, butoxypropyl, isobutoxypropyl, sec-butoxypropyl, tert-butoxypropyl, cyclopropoxypropyl, pentyloxypropyl, isopentyloxypropyl, hexyloxypropyl, isohexyloxypropyl, cyclopentyloxypropyl, cyclohexyloxypropyl, methoxybutyl, ethoxybutyl, propoxybutyl, isopropoxybutyl, butoxybutyl, isobutoxybutyl, secbutoxybutyl, tert-butoxybutyl, cyclopropoxybutyl, pentyloxybutyl, isopentyloxybutyl, hexyloxybutyl, isohexyloxybutyl, cyclopentyloxybutyl and cyclohexyloxybutyl groups. Among them, $C_{1-4}$ alkoxy($C_{1-4}$ alkyl) groups are particularly preferred.

Examples of the "lower alkoxycarbonylalkyl group" include $C_{1-6}$ alkoxycarbonyl($C_{1-6}$ alkyl) groups such as methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, cyclopropoxycarbonylmethyl, pentyloxycarbonylmethyl, isopentyloxycarbonylethyl, hexyloxycarbonylmethyl, isohexyloxycarbonylmethyl, cyclopentyloxycarbonylmethyl, cyclohexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, cyclopropoxycarbonylethyl, pentyloxycarbonylethyl, isopentyloxycarbonylethyl, hexyloxycarbonylethyl, isohexyloxycarbonylethyl, cyclopentyloxycarbonylethyl, cyclohexyloxycarbonylethyl, methoxycarbonylpropyl, ethoxycarbonylpropyl, propoxycarbonylpropyl, isopropoxycarbonylpropyl, butoxycarbonylpropyl, isobutoxycarbonylpropyl, sec-butoxycarbonylpropyl, tert-butoxycarbonylpropyl, cyclopropoxycarbonylpropyl, pentyloxycarbonylpropyl, isopentyloxycarbonylpropyl, hexyloxycarbony:propyl, isohexyloxycarbonylpropyl, cyclopentyloxycarbonylpropyl, cyclohexyloxycarbonylpropyl , methoxycarbonylbutyl, ethoxycarbonylbutyl, propoxycarbonylbutyl, isopropoxycarbonylbutyl, butoxycarbonylbutyl, isobutoxycarbonylbutyl, sec-butoxycarbonylbutyl, tert-butoxycarbonylbutyl, cyclopropoxycarbonylbutyl, pentyloxycarbonylbutyl, isopentyloxycarbonylbutyl, hexyloxycarbonylbutyl, isohexyloxycarbonylbutyl, cyclopentyloxycarbonylbutyl and cyclohexyloxycarbonylbutyl groups. Among them, ($C_{1-4}$ alkoxy)carbonyl($C_{1-4}$ alkyl) groups are particularly preferred.

Examples of the "carboxy(lower alkyl) group" include carboxy($C_{1-6}$ alkyl) groups. Among them, preferred are carboxy($C_{1-4}$ alkyl) groups such as carboxymethyl, carboxyethyl, carboxypropyl and carboxybutyl groups.

Examples of the "mono- or di-(lower alkyl)aminoalkyl group" include mono- or di-($C_{1-6}$ alkyl)amino($C_{1-6}$ alkyl) groups such as methylaminomethyl, methylaminoethyl, methylaminopropyl, methylaminobutyl, ethylaminomethyl, ethylaminoethyl, ethylaminopropyl, ethylaminobutyl, propylaminomethyl, propylaminoethyl, propylaminopropyl, propylaminobutyl, isopropylaminomethyl, isopropylaminoethyl, isopropylaminopropyl, isopropylaminobutyl, butylaminomethyl, butylaminoethyl, isobutylaminomethyl, isobutylaminoethyl, sec-butylaminomethyl, sec-butylaminoethyl, tert-butylaminomethyl, tert-butylaminoethyl, dimethylaminomethyl, dimethylaminoethyl, dimethylaminopropyl, dimethylaminobutyl, diethylaminomethyl, diethylaminoethyl, diethylaminopropyl, dipropylaminomethyl, dipropylaminoethyl, dipropylaminopropyl, diisopropylaminomethyl, diisopropylaminoethyl, diisopropylaminopropyl, dibutylaminoethyl, dibutylaminobutyl, diisobutylaminomethyl, diisobutylaminobutyl, methylethylaminomethyl, methylethylaminobutyl, methylpropylaminomethyl, methylpropylaminoethyl, methylpropylaminopropyl, methylpropylaminobutyl, methylisopropylaminomethyl, methylisopropylaminoethyl, methylisopropylaminopropyl, methylisopropylaminobutyl, ethylisopropylaminomethyl, ethylisopropylaminoethyl, ethylisopropylaminopropyl, ethylisopropylaminobutyl, ethylpropylaminomethyl, ethylpropylaminoethyl, ethylpropylaminopropyl, ethylpropylaminobutyl, methylbutylaminomethyl, methylbutylaminoethyl, methylbutylaminopropyl, methylbutylaminobutyl, ethylbutylaminomethyl, ethylbutylaminoethyl, ethylbutylaminopropyl, ethylbutylaminobutyl, propylbutylaminomethyl, propylbutylaminoethyl, propylbuty-laminopropyl, propylbutylaminobutyl, isopropylbutylaminomethyl, isopropylbutylaminoethyl, isopropylbutylaminopropyl, isopropylbutylaminobutyl, dicyclopropylaminomethyl, dicyclopropylaminoethyl, dicyclopropylaminopropyl, dicyclopropylaminobutyl, methylcyclopropylaminomethyl, methylcyclopropylaminoethyl, methylcyclopropylaminopropyl, methylcyclopropylaminobutyl, ethylcyclopropylaminomethyl, ethylcyclopropylaminoethyl, ethylcyclopropylaminopropyl, ethylcyclopropylaminobutyl, cyclopropylpropylaminomethyl, cyclopropylpropylaminoethyl, cyclopropylpropylaminopropyl, cyclopropylpropylaminobutyl, cyclopropylisopropylaminomethyl, cyclopropylisopropylaminoethyl, cyclopropylisopropylaminopropyl, cyclopropylisopropylaminobutyl, cyclopropylbutylaminomethyl, cyclopropylbutylaminoethyl, cyclopropylbutylaminopropyl, cyclopropylbutylaminobutyl, cyclopentylmethylaminomethyl, cyclopentylmethylaminoethyl, cyclopentylmethylaminopropyl, cyclopentylmethylaminobutyl, cyclopentylethylaminomethyl, cyclopentylethylaminoethyl, cyclopentylethylaminopropyl, cyclopentylethylaminobutyl, cyclopentylpropylaminomethyl, cyclopentylpropylaminoethyl, cyclopentylpropylaminopropyl, cyclopentylisopropylaminomethyl, cyclopentylisopropylaminoethyl, cyclopentylisopropylaminopropyl, cyclopentylisopropylaminobutyl, cyclopentylbutylaminomethyl, cyclopentylbutylaminoethyl, cyclopentylbutylaminopropyl, cyclopentylbutylaminobutyl, cyclohexylmethylaminomethyl, cyclohexylmethylaminoethyl, cyclohexylmethylaminopropyl, cyclohexylmethylaminobutyl, cyclohexylethylaminomethyl, cyclohexylethylaminoethyl, cyclohexylethylaminopropyl, cyclohexylethylaminobutyl, cyclohexylpropylaminomethyl, cyclohexylpropylaminoethyl, cyclohexylpropylamino- propyl, cyclohexylisopropylaminomethyl, cyclohexyliso- propylaminoethyl, cyclohexylisopropylaminopropyl, cyclohexylisopropylaminobutyl, cyclohexylbutylamino- methyl, cyclohexylbutylaminoethyl, cyclohexylbutylaminorpropyl and cyclohexylbutylaminobutyl groups. Among them, mono- or di-($C_{1-4}$ alkyl)amino($C_{1-4}$ alkyl) groups are preferred.

Examples of the "mono- or di-(lower alkyl) aminoalkylamino group" include mono- or di-($C_{1-6}$ alkyl) amino($C_{1-6}$ alkyl)amino groups such as methylaminomethylamino, methylaminoethylamino, methylaminopropylamino, methylaminobutylamino, ethylaminomethylamino, ethylaminoethylamino, ethylaminopropylamino, ethylaminobutylamino, propylaminomethylamino, propylaminoethylamino, propylaminopropylamino, propylaminobutylamino, isopropylaminomethylamino, isopropylaminoethylamino, isopropylaminopropylamino, isopropylaminobutylamino, butylaminomethylamino, butylaminoethylamino, isobutylaminomethylamino, isobutylaminoethylamino, sec-butylaminomethylamino, sec-butylaminoethylamino, tert-butylaminomethylamino, tert-butylaminoethylamino, dimethylaminomethylamino, dimethylaminoethylamino, dimethylaminopropylamino, dimethylaminobutylamino, diethylaminomethylamino, diethylaminoethylamino, diethylaminopropylamino, dipropylaminomethylamino, dipropylaminoethylamino, dipropylaminopropylamino, diisopropylaminomethylamino, diisopropylaminoethylamino, diisopropylaminopropylamino, dibutylaminoethylamino, dibutylaminobutylamino, diisobutylaminomethylamino, diisobutylaminobutylamino, methylethylaminomethylamino, methylethylaminobutylamino, methylpropylaminomethylamino, methylpropylaminoethylamino, methylpropylaminopropylamino, methylpropylaminobutylamino, methylisopropylaminomethylamino, methylisopropylaminoethylamino, methylisopropylaminopropylamino, methylisopropylaminobutylamino, ethylisopropylaminopropylamino, ethylisopropylaminobutylamino, ethylpropylaminomethylamino, ethylpropylaminoethylamino, ethylpropylaminopropylamino, ethylpropylaminobutylamino, methylbutylaminomethylamino, methylbutylaminoethylamino, methylbutylaminopropylamino, methylbutylaminobutylamino, ethylbutylaminomethylamino, ethylbutylaminoethylamino, ethylbutylaminopropylamino, ethylbutylaminobutylamino, propylbutylaminomethylamino, propylbutylaminoethylamino, propylbutylaminopropylamino, propylbutylaminobutylamino, isopropylbutylaminomethylamino, isopropylbutylaminoethylamino, isopropylbutylaminopropylamino, isopropylbutylaminobutylamino, dicyclopropylaminomethylamino, dicyclopropylaminoethylamino, dicyclopropylaminopropylamino, dicyclopropylaminobutylamino, methylcyclopropylaminomethylamino, methylcyclopropylaminoethylamino, methylcyclopropylaminopropylamino, methylcyclopropylaminobutylamino, ethylcyclopropylaminomethylamino, ethylcyclopropylaminoethylamino, ethylcyclopropylaminopropylamino, ethylcyclopropylaminobutylamino, cyclopropylpropylaminomethylamino, cyclopropylpropylaminoethylamino, cyclopropylpropylaminopropy-lamino, cyclopropylpropylaminobutylamino, cyclopropylisopropylaminomethylamino, cyclopropylisopropylaminoethylamino, cyclopropylisopropylaminopropylamino, cyclopropylisopropylaminobutylamino, cyclopropylbutylaminomethylamino, cyclopropylbutylaminoethylamino, cyclopropylbutylaminopropylamino, cyclopropylbutylaminobutylamino, cyclopentylmethylaminomethylamino, cyclopentylmethylaminoethylamino, cyclopentylmethylaminopropylamino, cyclopentylmethylaminobutylamino, cyclopentylethylaminomethylamino, cyclopentylethylaminoethylamino, cyclopentylethylaminopropylamino, cyclopentylethylaminobutylamino, cyclopentylpropylaminomethylamino, cyclopentylpropylaminoethylamino, cyclopentylpropylaminopropylamino, cyclopentylisopropylaminomethylamino, cyclopentylisopropylaminoethylamino, cyclopentylisopropylaminopropylamino, cyclopentylisopropylaminobutylamino, cyclopentylbutylaminomethylamino, cyclopentylbutylaminoethylamino, cyclopentylbutylaminopropylamino, cyclopentylbutylaminobutylamino, cyclohexylmethylaminomethylamino, cyclohexylmethylaminoethylamino, cyclohexylmethylaminopropylamino, cyclohexylmethylaminobutylamino, cyclohexylethylaminomethylamino, cyclohexylethylaminoethylamino, cycylohexylethylaminopropylamino, cyclohexylethylaminobutylamino, cyclohexylpropylaminomethylamino, cyclohexylpropylaminoethylamino, cyclohexylpropylaminopropylamino, cyclohexylisopropylaminomethylamino, cyclohexylisopropylaminoethylamino, cyclohexylisopropylaminopropylamino, cyclohexylisopropylaminobutylamino, cyclohexylbutyl- aminomethylamino, cyclohexylbutylaminoethylamino, cyclohexylbutylaminopropylamino and cyclohexylbutylaminobutylamino groups. Among them, mono- or di-($C_{1-4}$ alkyl)amino ($C_{1-4}$ alkyl)amino groups are particularly preferred.

Examples of the "phenylalkyl group" include phenyl($C_{1-6}$ alkyl) groups such as benzyl, phenetyl, 1-phenylethyl, 1-phenylpropyl, 2-phenylpropyl, 3-phenylpropyl, 1-methyl-1-phenylethyl, 1-ethyl-2-phenylethyl, 1-phenylbutyl, 2-phenylbutyl, 3-phenylbutyl, 4-phenylbutyl, 1-benzylpropyl, 1-methyl-1-phenylpropyl, 1-methyl-2-phenylpropyl, 1-methyl3-phenylpropyl, 2-methyl-1-phenylpropyl, 2-methyl-2-phenylpropyl, 2-methyl-3-phenylpropyl and 1,1-dimethyl-2-phenylethyl groups.

Examples of the "lower alkylthio group" include $C_{1-6}$ alkylthio groups such as methylthio, ethylthio, propylthio, isopropylthio, cyclopropylthio, butylthio, isobutylthio, sec-butylthio, tert-butylthio, cyclobutylthio, pentylthio, 1-methylbutylthio, 2-methylbutylthio, isopentylthio, tert-pentylthio, 1,2-dimethylpropylthio, neopentylthio, 1-ethylpropylthio, cyclopentylthio, hexylthio, 1-methylpentylthio, 2-methylpentylthio, 3-methylpentylthio, isohexylthio, 1-ethylbutylthio, 2-ethylbutylthio, 1,1-dimethylbutylthio, 1,2-diemthylbutylthio, 1,3-dimethylbutylthio, 2,2-dimethylbutylthio, 2,3-dimethylbutylthio, 3,3-dimethylbutylthio, 1-methyl-1-ethylpropylthio, 1-ethyl-2-methylpropylthio, 1,1,2-trimethylpropylthio, 1,2,2-trimethylpropylthio and cyclohexylthio groups. Among them, $C_{1-4}$ alkylthio groups are particularly preferred.

The term "saturated nitrogen-containing heterocyclic group" means a saturated 5–7 membered heterocyclic group containing at least one nitrogen atom in the ring thereof. Preferred examples include saturated 5–6 membered heterocyclic groups each containing one or two nitrogen atoms and 0 or 1 oxygen or sulfur atom, such as pyrrolidinyl, imidazolidinyl, pyrazolidinyl, oxazolidinyl, thiazolydinyl, isooxazolidinyl, isothiazolidinyl, piperidinyl, piperazinyl, morpholino and thiomorpholino groups.

The "unsaturated nitrogen-containing heterocyclic group" means an unsaturated 5–7 membered heterocyclic group containing at least one nitrogen atom in the ring thereof. Preferred are unsaturated 5–6 membered heterocyclic groups each containing 1 to 4 nitrogen atoms and 0 or 1 oxygen or sulfur atom. Specific examples include pyrrolyl, imidazolyl, pyrazolyl, triazolyl, tetrazolyl, oxazolyl, thiazolyl, isooxazolyl, isothiazolyl, pyridyl, dihydropyridyl and tetrahydropyridyl groups.

Examples of the "branched alkylamino group" include branched $C_{2-6}$ alkylamino groups, more specifically, isopropylamino, sec-butylamino and isobutylamino groups.

Examples of the "piperidinylalkylamino group" include piperidinyl ($C_{1-6}$ alkyl)amino groups, more specifically, piperidinylmethylamino and piperidinylethylamino groups.

In the invention compound (I), it is preferred that one of $R^1$, $R^2$ and $R^3$ represents a lower alkoxy, nitro or formylamino group and the other two are selected from a hydrogen atom, a hydroxy group, a lower alkyl group, a lower alkoxy group, a lower alkylcarbonyloxy group, a halogen atom, a nitro group, an amino group, a mono- or di-(lower alkyl) amino group, mono- or di-(lower alkyl)carbonylamino group, formylamino group and mono- or di-(lower alkyl) aminoalkylamino group. As the nitrogen-containing heterocyclic group represented independently by $R^6$ and $R^7$, piperidinyl, piperazinyl and pyridyl groups are particularly preferred.

As the nitrogen-containing heterocyclic group which is formed by $R^6$ and $R^7$ together with the adjacent nitrogen atom, saturated nitrogen-containing heterocyclic groups are preferred, with pyrrolidinyl, imidazolidinyl, pyrazolidinyl, piperidinyl, piperazinyl, isooxazolidinyl and morpholino groups being particularly preferred.

As the nitrogen-containing saturated heterocyclic group which is formed by $R^8$ and $R^9$ together with the adjacent carbon atom, pyrrolidinyl, imidazolidinyl, pyrazolidinyl, oxazolidinyl, thiazolidinyl groups are particularly preferred.

In the formula (I), it is preferred that one of $R^1$, $R^2$ and $R^3$ represents a lower alkoxy, nitro or formylamino group and the other two are selected from a hydrogen atom, a hydroxy group, a lower alkyl group, a lower alkoxy group, a lower alkylcarbonyloxy group, a halogen atom, a nitro group, an amino group, a mono- or di-(lower alkyl)amino group, a mono or di-(lower alkyl)carbonylamino group, a formylamino group and a mono- or di-(lower alkyl) aminoalkylamino group; $R^4$ represents a hydrogen atom or a lower alkyl group; $R^5$ represents a hydrogen atom, a halogen atom or a lower alkyl group; A represents —N($R^6$)$R^7$ (in which $R^6$ and $R^7$ have the same meanings as defined above); B represents an imino group which may be substituted by a lower alkyl group; and m stands for 2 to 4.

Furthermore, in the formula (I), it is particularly preferred that one of $R^1$, $R^2$ and $R^3$ represents a lower alkoxy, nitro or formylamino group and the other two are selected from a hydrogen atom, a hydroxy group, a lower alkoxy group and a halogen atom; $R^4$ and $R^5$ each represents a hydrogen atom; B represents an imino group which may be substituted by a lower alkyl group; m stands for 2 to 4; and A represents —N($R^6$)$R^7$ (in which $R^6$ and $R^7$ have the same meanings as defined above).

The invention compound (I) or intermediate (II) for the preparation of the invention compound can be converted into its salt in a manner known per se in the art. Examples of the salt of the invention compound (I) or intermediate (II) include acid addition salts with an inorganic acid, such as hydrochloride, sulfate, nitrate, phosphate, hydrobromide and hydroiodide; and acid addition salts with an organic acid such as acetate, oxalate, malonate, succinate, maleate, fumarate, lactate, malate, citrate, tartrate, methanesulfonate and ethanesulfonate.

The present invention also embraces various solvates, such as hydrates, of the invention compound (I) or the intermediate (II).

The invention compound (I) sometimes exhibits proton tautomerism, particularly imine-enamine tautomerism. Examples of such tautomerism include:

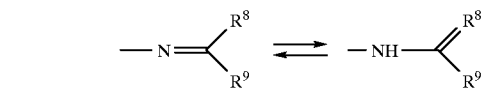

The invention compound (I) or the intermediate (II) can be prepared by various synthesis processes, with its basic skeleton or characteristics of its group taken into consideration. Typical synthesis processes (A and B) for it will be described below. Here, it is possible to prepare the invention compound by any one of the preparation process A, preparation process B and processes in accordance therewith.

Preparation Process A:

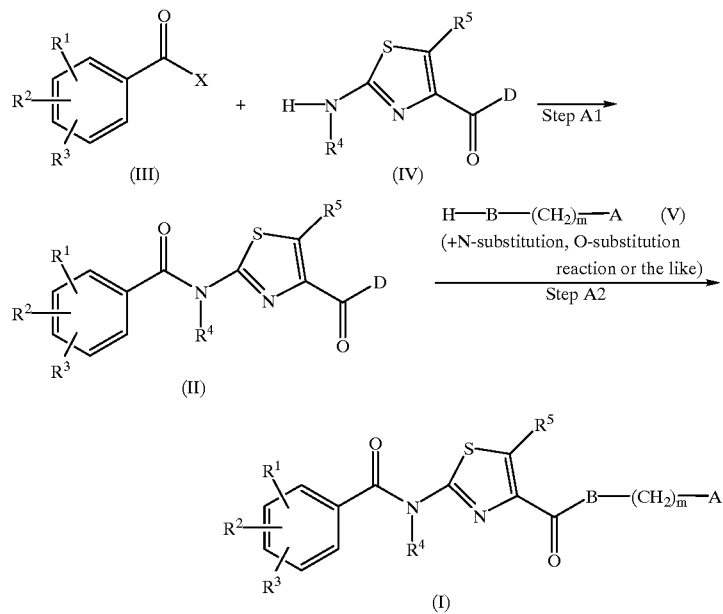

wherein X represents an eliminating group such as p-nitrophenoxy group, a halogen atom or a hydroxy group, and $R^1$, $R^2$, $R^3$, $R^4$, $R^5$, A, B, D and m have the same meanings as defined above.

This process will hereinafter be described by each step.

Step A1:

A thiazole derivative (II) can be prepared by reacting the compound represented by the formula (III) with the compound represented by the formula (IV). The reaction is carried out in the presence or absence of a base, for example, an alkali metal carbonate such as potassium carbonate, potassium bicarbonate, sodium carbonate or sodium bicarbonate, an alkali metal hydroxide such as potassium hydroxide, sodium hydroxide or lithium hydroxide, an alkylamine such as triethylamine or diisopropylethylamine, or a pyridine base compound such as pyridine, lutidine or 4-dimethylaminopyridine in a solventless manner or in a solvent which does not exert an influence on the reaction, for example, an aprotic polar solvent such as acetonitrile, N,N-dimethylformamide or dimethylsulfoxide, a halogen base solvent such as methylene chloride, chloroform or 1,2-dichloroethane, an ether base solvent such as ether, tetrahydrofuran or dioxane or a benzene base solvent such as toluene. The reaction can ordinarily be carried out at room temperature or under heating.

When X of Compound (III) represents a hydroxy group, the main reaction can be carried out after it is converted into a highly reactive substituent such as p-nitrophenoxy group or halogen atom in a manner known per se in the art.

Incidentally, when the thiazole derivative (II) or invention compound (I) containing as any one of $R^1$, $R^2$ and $R^3$ an amino group or a lower-alkyl-substituted amino group is prepared, the main reaction is effected after protection of the amino group of Compound (III), followed by deprotection after the main reaction or after the reaction in the subsequent step A2; or the main reaction is effected by using a nitro-containing Compound (III), followed by reduction after the main reaction or after the reaction in the step A2 to convert the nitro group into an amino group.

When the thiazole derivative (II) or invention compound (I) containing a hydroxy group as any one of $R^1$, $R^2$ and $R^3$ is prepared, Compound (III) containing an alkoxy group can be used instead of that containing a hydroxy group. In this case, after the main reaction or the reaction in the subsequent step A2, the alkoxy group is converted into a hydroxy group through the dealkylation reaction by using a pyridine hydrochloride, boron tribromide, a solution of hydrogenbromide solution in acetic acid, catalytic reduction or the like.

When the thiazole derivative (II) or invention compound (I) containing a lower alkylcarbonyloxy group as any one of $R^1$, $R^2$ and $R^3$ is prepared, a carboxylic acid or reactive derivative thereof is acted to the invention compound which has been prepared above and contains a hydroxy group as any one of $R^1$, $R^2$ and $R^3$.

When the thiazole derivative (II) or invention compound (I) containing as any one of $R^1$, $R^2$ and $R^3$ a halogen atom, hydroxy group or nitro group is prepared, a nitrite salt and a strong acid are acted on the amino-containing compound (III) to convert it into a diazonium salt and then the resulting diazonium salt is converted it into various substituents by the substitution reaction (Sandmeyer method, Gattermann reaction, Schiemann reaction). This operation can be carried out after the main reaction or after the reaction in the subsequent step A2.

Step A2

The invention compound (I) can be obtained by reacting the thiazole derivative (II) obtained in the step A1 with Compound (V) and then subjecting the reaction mixture to N-substitution reaction as needed. The reaction is effected as in Step A1.

When D of the thiazole derivative (II) represents a hydroxy group, it is also possible to carry out the main reaction after converting the derivative into a highly reactive substituent such as p-nitrophenoxy group or halogen atom in a manner known per se in the art.

The invention compound (I) can be introduced into another invention compound (I) by subjecting it to N-substitution reaction or O-substitution reaction. The N-substitution reaction can be effected by the method known to date such as monoalkylation, dialkylation or amidation. More specifically, the N-substitution can be carried out as needed by the reaction in which a reducing agent such as formic acid or boron hydride compound and an aldehyde such as formaldehyde, acetaldehyde or glyoxal or an acid anhydride such as acetic anhydride are used in combination, the reaction in which a carboxylic acid or reactive derivative thereof is used, the reaction in which an alkyl halide is used, the reaction in which a compound containing therein an eliminating group such as lower alkoxy, lower alkylthio, lower alkylsulfonyl or lower alkylsulfinyl, or a halogen atom is used, the reduction reaction in which an aldehyde or ketone is acted to form an imine derivative, followed by the addition of a boron hydride compound or the hydrogenation reaction in which a palladium carbon or the like is used as a catalyst, or a combination thereof. Incidentally, when a phthalimide-substituted alkyl halide is employed in the N-substitution reaction using an alkyl halide, it is possible to convert the phthalimide group into an amino group by a base such as methylamine (Gabriel synthesis) and then subject the resulting amino group to the N-substitution reaction.

The O-substitution reaction can be effected by the method known to date such as alkylation or acylation. It is possible to effect the O-substitution reaction as needed in accordance with the reaction in which a carboxylic acid or reactive derivative thereof is used or the reaction in which an alkyl halide is used, or a combination thereof.

Incidentally, as Compound (V), a commercially-available compound can be employed or alternatively, it can be prepared by using the above-described reactions for N-substitution in combination as needed.

Preparation Process B

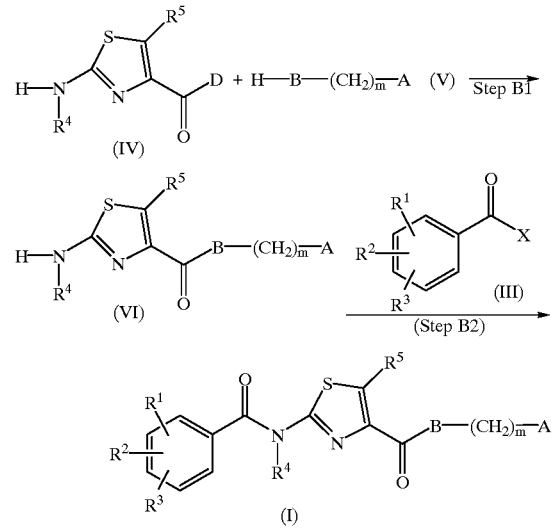

wherein X, $R^1$, $R^2$, $R^3$, $R^4$, $R^5$, A, B, D and m have the same meanings as defined above.

Step B1

Compound (VI) can be prepared by reacting Compound (IV) with Compound (V). The reaction is effected in a similar manner to Step A2.

Step B2

Compound (VI) obtained in Step B1 can be introduced into the invention compound (I) by being reacted with Compound (III). The reaction is effected in a similar manner to Step A1.

Incidentally, when the invention compound (I) containing as any one of $R^1$, $R^2$ and $R^3$ an amino group or (lower alkyl)-substituted amino group is prepared, the main reaction is effected after the protection of the amino group of Compound (III), followed by deprotection; or the main reaction is effected using a nitro-containing Compound (III), followed by reduction after the main reaction to convert the nitro group into an amino group.

When the thiazole derivative (II) or invention compound (I) containing as any one of $R^1$, $R^2$ and $R^3$ a hydroxy group is prepared, it is possible to use an alkoxycontaining Compound (III) instead of using a hydroxycontaining Compound (III). When the alkoxy-containing Compound (III) is used, the derivative or the invention compound is prepared, subsequent to the main reaction or the reaction in Step A2, by the dealkylation reaction using pyridine hydrochloride, boron tribromide, a solution of hydrogenbromide solution in acetic acid, or catalytic reduction to convert the alkoxy group into a hydroxy group.

When the thiazole derivative (II) or invention compound (I) containing as any one of $R^1$, $R^2$ and $R^3$ an alkylcarbonyloxy group is prepared, a carboxylic acid or reactive derivative thereof is acted to the invention compound which has been prepared above and contains as any one of $R^1$, $R^2$ and $R^3$ a hydroxy group.

When the thiazole derivative (II) or invention compound (I) containing as any one of $R^1$, $R^2$ and $R^3$ a halogen atom, hydroxy group or nitro group is prepared, a nitrite salt and a strong acid are acted on the amino-containing compound (III) to convert it into a diazonium salt and then the resulting diazonium salt is converted it into various substituents by the substitution reaction (Sandmeyer method, Gattermann reaction, Schiemann reaction). This procedure can be carried out after the main reaction or after the reaction in the subsequent step A2.

Invention Compound (I) prepared by any one of the above-described Preparation Processes A and B and processes in accordance therewith can be prepared in the form of a salt in a manner known per se in the art.

Invention Compound (I) so obtained has, as will be described later, excellent improving effects on gastrointestinal dysmotility and at the same time has high safety so that it is useful for the prevention and treatment of dysmotility in the gastrointestinal tract. Examples of the symptoms and diseases caused by digestive dysmotility include epigastric dyscomfort, nausea, vomiting, heart burn, anorexia, epigastric pain, abdominal flatulence, chronic gastritis, reflux esophagitis and postgastrectomy syndrome. The invention compound (I) can be formed as a composition for oral or parenteral administration, mixed with a pharmaceutically acceptable carrier. The invention compound (I) can be formulated into tablets, powders, granules or capsules by adding suitable additives, for example, an excipient such as lactose, mannitol, corn starch or crystalline cellulose, a binder such as cellulose derivative, gum arabic or gelatin, a disintegrator such as carboxymethyl cellulose calcium and a lubricant such as talc or magnesium stearate as needed. These solid preparations can also be formed into an enteric-coated preparation by using a covering base such as hydroxypropyl methylcellulose phthalate, hydroxypropyl methylcellulose acetate succinate, cellulose acetate phthalate or methacrylate copolymer. As a composition for parenteral administration, the invention compound can be formulated into a liquid agent for injection by using water, ethanol, glycerin and ordinarily-used surfactant, or into a suppository by using a suppository base in combination.

The dosage of the invention compound (I) varies depending on the age, weight, symptom, treatment effects, administration method and administration term. In the case of oral administration, the compound (I) is generally administered at a dose of 0.1 to 2,000 mg/day, preferably 1 to 300 mg/day in one to three portions a day. (Gastroprokinetic activity)

Force transducers (F-121S; Star Medical) were chronically implanted onto the gastric antrum and duodenum of a male dog (weight: 9 to 10 kg) [Itoh, Z. et al., Am. J. Dig. Dis., 22, 117–124(1977)]. The test was carried out two hours after feeding (30 g/kg, Gaines meal; Ajinomoto General Foods). Contraction signals obtained from each transducer were amplified (RTA-1200; Nihon Kohden) and recorded on a recorder and a computer.

The area under the contraction wave and base line in the antrum was integrated by an analysis program (DSSFFT, V. 21; Nihon Kohden). Motor activity in the antrum was expressed as the motor index. The test compound was dissolved in physiological saline and given intravenously.

The results were calculated by the following equation and are shown in Table 1 as % of motor index.

$$\text{Motor index}(\%) = \frac{\text{Motor index for 10 min after administration}}{\text{Motor index for 10 min before administration}} \times 100$$

TABLE 1

| Compound | Dose (mg/kg) | Motor index (%) |
|---|---|---|
| Compound of Ex. 3 | 5 | 202.3 |
| Compound of Ex. 6 | 5 | 284.5 |
| Compound of Ex. 9 | 5 | 316.7 |
| Compound of Ex. 10 | 1 | 254.8 |
| Compound of Ex. 11 | 1 | 310.7 |
| Compound of Ex. 12 | 0.5 | 229.5 |
| Compound of Ex. 17 | 5 | 356.0 |
| Compound of Ex. 18 | 5 | 299.0 |
| Compound of Ex. 19 | 5 | 420.9 |
| Compound of Ex. 21 | 1 | 157.1 |
| Compound of Ex. 38 | 1 | 213.3 |
| Compound of Ex. 115 | 1 | 342.9 |
| Compound of Ex. 117 | 1 | 437.4 |
| Compound of Ex. 156 | 1 | 257.0 |
| Compound of Ex. 162 | 1 | 265.7 |

(Toxicity Test)

Three ICR mice (4–5 weeks) were employed in each group. Test compound suspended with 5% gum arabic was given orally at a dose of 500 mg/kg. Within one week observation, no case of death was observed in each group.

EXAMPLES

The present invention will hereinafter be described more specifically by Referential Examples and Examples but it should however be borne in mind that the present invention is not limited to or by the following examples.

Referential Example 1

2-[N-(3,4-Dimethoxybenzoyl)amino]-4-(ethoxycarbonyl)-1,3-thiazole

In 100 ml of methylene chloride, 21.3 g of 2-amino-4-ethoxycarbonyl-1,3-thiazole was suspended, followed by the addition of 24.8 g of 3,4-dimethoxybenzoyl chloride, 25.3 g of triethylamine and 0.15 g of 4-dimethylaminopyridine. The resulting mixture was refluxed for 2 hours. After the reaction mixture was allowed to cool down, methylene chloride was distilled off under reduced pressure. To the residue, 1000 ml of water was added. Crystals so precipitated were collected by filtration and then recrystallized from ethanol, whereby 30.3 g of the title compound was obtained. Yield: 73%.

$^1$H-NMR(CDCl$_3$)δ: 1.39(3H,t), 3.95(3H,s), 3.97(3H,s), 4.39(2H,q), 6.95(1H,d), 7.46–7.51(2H,m), 7.88(1H,s), 9.91 (1H,brs).

Referential Example 2

2-[N-(2,4,5-Trimethoxybenzoyl)amino]-4-(ethoxycarbonyl)-1,3-thiazole

In a similar manner to Referential Example 1 except that 2,4,5-trimethoxybenzoyl chloride was used instead of 3,4-dimethoxybenzoyl chloride, the title compound was obtained.

IR(KBr)cm$^{-1}$: 3299, 3127, 1728, 1665; $^1$H-NMR(CDCl$_3$) δ: 1.42(3H,t), 3.92(3H,s), 3.97(3H,s), 4.09(3H,s), 4.43(2H, q), 6.58(1H,s), 7.77(1H,s), 7.85(1H,s), 11.13(1H,brs).

Referential Example 3
2-[N-(2,4,5-Trimethoxybenzoyl)amino]-4-(hydroxycarbonyl)-1,3-thiazole In 100 ml of methanol, 15 g of 2-[N-(2,4,5-trimethoxybenzoyl)amino]-4-(ethoxycarbonyl)-1,3-thiazole obtained in Referential Example 2 were suspended, followed by the addition of an aqueous solution which had been obtained by dissolving 8.19 g of sodium hydroxide in 100 ml of water. The resulting mixture was stirred at room temperature for one hour. The reaction mixture was made acidic with 1N hydrochloric acid and the crystals so precipitated were collected by filtration, whereby 9.2 g of the title compound was obtained. Yield: 66%.

MS(FAB,m/z): 399(MH$^+$); IR(KBr)cm$^{-1}$: 1719, 1655; $^1$H-NMR(DMSO-d$_6$)δ: 3.78(3H,s), 3.92(3H,s), 4.03(3H,s), 6.85(1H,s), 7.43(1H,s), 8.00(1H,s), 9.00(1H,brs), 11.52(1H, brs).

Referential Example 4
2-[N-Methyl-N-(3,4-dimethoxybenzoyl)amino]-4-(ethoxycarbonyl)-1,3-thiazole In a similar manner to Referential Example 1 except that 2-(N-methylamino)-4-(ethoxycarbony)-1,3-thiazole was used instead of 2-amino-4-ethoxycarbonyl-1,3-thiazole, the title compound was obtained.

MS(EI,m/z): 350(M$^+$); IR(KBr)cm$^{-1}$: 1719, 1655; $^1$H-NMR(DMSO-d$_6$)δ: 1.41(3H,t), 3.80(3H,s), 3.92(3H,s), 3.95(3H,s), 4.41(2H,q), 6.93–6.96(1H,m), 7.15–7.21(2H, m), 7.90(1H,s).

Referential Example 5
2-(N-Methylamino)-4-[(2-dimethylaminoethyl)aminocarbonyl]-1,3-thiazole In 3.5 g of N,N-dimethylethylenediamine, 2.5 g of 2-(N-methylamino)-4-(ethoxycarbonyl)-1,3-thiazole was dissolved, followed by stirring at 100° C. for 6 hours. The reaction mixture was poured into isopropyl alcohol and the crystals so precipitated were collected by filtration, whereby 1.68 g of the title compound was obtained. Yield: 51.5%.

MS (EI,m/z): 228(M$^+$); IR(KBr)cm$^{-1}$: 3395, 3198, 3104, 2824, 1657; $^1$H-NMR(CDCl$_3$)δ: 2.27(6H,s), 2.50(2H,t), 2.97(3H,d), 3.49(2H,m), 5.37(1H,br), 7.30(1H,s), 7.46(1H, br).

Referential Example 6
2-[N-(4,5-Dimethoxy-2-hydroxybenzoyl)amino]-4-(ethoxycarbonyl)-1,3-thiazole acetate To 18.2 g of 2-[N-(2,4,5-trimethoxybenzoyl)amino]-4-(ethoxycarbonyl)-1,3-thiazole obtained in Referential Example 2, 17.5 g of pyridine chloride, 3.93 g of pyridine and 150 ml of N,N-dimethylformamide were added, followed by reflux for 6 hours. The reaction mixture was poured into ice water. The crystals so precipitated were collected by filtration, washed with water and then dried under reduced pressure. The crystals so obtained were recrystallized from acetic acid, whereby 14.3 g of the title compound was obtained. Yield: 70%.

MS(EI,m/z): 413(M$^+$); IR(KBr)cm$^{-1}$: 3135, 1715, 1709, 1644; $^1$H-NMR(DMSO-d$_6$)δ: 1.31(3H,t), 1.91(3H,s), 3.78 (3H,s), 3.83(3H,s), 4.30(2H,q), 6.61(1H,s), 7.64(1H,s), 8.11 (1H,s), 11.5(1H,brs), 12.4(1H,brs).

Example 1
2-[N-Methyl-N-(3,4-dimethoxybenzoyl)amino]-4-[(2dimethylaminoethyl)aminocarbonyl]-1,3-thiazole maleate (Preparation Process A)
A mixture of 8.41 g of 2-[N-methyl-N-(3,4-dimethoxybenzoyl)amino]-4-(ethoxycarbonyl)-1,3-thiazole obtained in Referential Example 4 and N,N-dimethylethylenediamine was stirred at 100° C. for 4 hours. After being allowed to cool down, the reaction mixture was purified by chromatography on a silica gel column (chloroform:methanol=5:1), whereby 7.8 g of the title compound was obtained as a free base. The compound so obtained was converted into its maleate and thus, the title compound was obtained. Yield: 82%.

MS(EI,m/z): 392(M$^+$); IR(KBr)cm$^{-1}$: 3380, 1649; $^1$H-NMR(DMSO-d$_6$)δ: 2.84(6H,s), 3.21–3.35(2H,m), 3.60–3.66(2H,m), 3.70(3H,s), 3.82(3H,s), 3.84(3H,s), 6.01 (2H,s), 7.09(1H,d), 7.25–7.28(2H,m), 7.93(1H,s), 8.56(1H, t), 8.60–10.00(1H,br), 13.00–14.00(1H,br).

(Preparation Process B)
1.68 g of 2-(N-methylamino)-4-[(2-dimethylaminoethyl)-aminocarbonyl]-1,3-thiazole obtained in Referential Example 5 and 2.23 g of p-nitrophenyl 3,4-dimethoxyphenylbenzoate were stirred at 140° C. for 6 hours. The reaction mixture was dissolved in chloroform, washed successively with a saturated aqueous solution of sodium bicarbonate and saturated saline and then dried. The solvent was distilled off and the residue was recrystallized from ethyl acetate, whereby 675 mg of the title compound was obtained as a free base. The compound so obtained was converted into a maleate as in Preparation Process 1 and thus, the title compound was obtained.

Example 2
2-[N-(3,4-Dimethoxybenzoyl)amino]-4-[(2-aminoethyl)-aminocarbonyl]-1,3-thiazole hydrochloride A mixture of 8 g of 2-[N-(3,4-dimethoxybenzoyl)amino]-4-(ethoxycarbonyl)-1,3-thiazole obtained in Referential Example 1 and 14.3 g of ethylenediamine was stirred at 100° C. for one hour. The reaction mixture was subjected to distillation under reduced pressure. To the residue, 50 ml of methanol was added and crystals so precipitated were collected by filtration, whereby 6.5 g of the title compound was obtained as a free base. The compound was converted into its hydrochloride and thus, the title compound was obtained. Yield: 78%.

MS (FAB,m/z): 351(MH$^+$); IR(KBr)cm$^{-1}$: 3400, 3381, 1653, 1650; $^1$H-NMR(DMSO-d$_6$)δ: 2.99(2H,m), 3.56(2H, m), 3.86(3H,s), 3.87(3H,s), 7.11(1H,d), 7.73–7.80(2H,m), 8.14(3H,br), 8.23(1H,t), 12.68(1H,br), 13.00–14.00(1H,br).

In a similar manner to Example 1 or 2, Compounds of Examples 3 to 21 which will be described below were prepared using a compound selected from those obtained in Referential Examples 1 to 5.

Example 3
2-[N-(3,4-Dimethoxybenzoyl)amino]-4-[(2-dimethylaminoethyl)aminocarbonyl]-1,3-thiazole maleate MS(FAB,m/z): 379(MH$^+$); IR(KBr)cm$^{-1}$: 3359, 1650, 1551; $^1$H-NMR(DMSO-d$_6$)δ: 2.83(6H,s), 3.24(2H,t), 3.64 (2H,q), 3.86(3H,s), 3.87(3H,s), 6.03(2H,s), 7.12(1H,d), 7.71–7.80(2H,m), 7.88(1H,s), 8.20(1H,brs), 12.58(3H,brs).

Example 4
2-[N-(3,4-Dimethoxybenzoyl)amino]-4-[[2-(1-imidazolyl)-ethyl]aminocarbonyl]-1,3-thiazole dihydrochloride MS(EI,m/z): 401(M$^+$); IR(KBr)cm$^{-1}$: 3142, 1676, 1578; $^1$H-NMR(DMSO$_6$)δ: 3.73–3.86(8H,m), 4.39–4.42(2H,m), 7.11(1H,d), 7.66–8.28(6H,m), 9.20–9.21(1H,m), 12.64(1H, br), 14.77(1H,br), 13.00–14.00(1H,br).

Example 5
2-[N-(3,4-Dimethoxybenzoyl)amino]-4-[(2-diethylaminoethyl)aminocarbonyl]-1,3-thiazole MS(FAB,m/z): 407(MH$^+$); IR(KBr)cm$^{-1}$: 3390, 3246, 1684, 1659; $^1$H-NMR(DMSO$_6$)δ: 1.25(6H,t), 3.13–3.25(6H, m), 3.65–3.72(2H,m), 3.87(6H,s), 7.12(1H,d), 7.73–7.80 (2H,m), 7.96(1H,s), 8.40(1H,t), 10.57(1H,br), 12.67(1H,br).

Example 6
2-[N-(3,4-Dimethoxybenzoyl)amino]-4-[(2-diisopropylaminoethyl)aminocarbonyl]-1,3-thiazole maleate MS(EI,m/z): 434(M$^+$); IR(KBr)cm$^{-1}$: 3403, 1671, 1651; $^1$H-NMR(DMSO-d$_6$)δ: 1.30(12H,d), 3.10–3.78(6H,m), 3.86 (6H,s), 6.05(2H,s), 7.12(1H,d), 7.70–7.89(3H,m), 8.30–8.70 (3H,br), 12.54(1H,s).

Example 7
2-[N-(3,4-Dimethoxybenzoyl)amino]-4-[N-methyl-N-(2-dimethylaminoethyl)aminocarbonyl]-1,3-thiazole fumarate MS(FAB,m/z): 393(MH$^+$); IR(KBr)cm$^{-1}$: 3453, 1617, 1516, 1269; $^1$H-NMR(DMSO-d$_6$)δ: 2.40(6H,br), 2.81(2H, m), 3.06(3H,m), 3.68(2H,brs), 3.85(3H,s), 3.86(3H,s), 6.59 (2H,s), 7.11(1H,d), 7.59(1H,d), 7.77(2H,m).

Example 8
2-[N-(2,4-Dimethoxybenzoyl)amino]-4-[(2-dimethylaminoethyl)aminocarbonyl]-1,3-thiazole maleate MS(EI,m/z): 377(M$^+$); IR(KBr)cm$^{-1}$: 3335, 1709, 1653; $^1$H-NMR(DMSO-d$_6$)δ: 2.59(2H,t), 2.84(6H,s), 3.61(2H,q), 3.89(3H,s), 4.04(3H,s), 6.02(2H,s), 6.73–6.80(2H,m), 7.87–7.96(2H,m), 8.47(1H,t), 8.60–10.00(1H,br), 11.23(1H, s), 13.00–14.00(1H,br).

Example 9
2-[N-(2,4,5-Trimethoxybenzoyl)amino]-4-[(2-dimethylaminoethyl)aminocarbonyl]-1,3-thiazole maleate MS(EI,m/z): 407(M$^+$); IR(KBr)cm$^{-1}$: 3322, 1657, 1611; $^1$H-NMR(DMSO-d$_6$)δ: 2.83(6H,s), 3.25(2H,t), 3.60(2H,t), 3.78(3H,s), 3.93(3H,s), 4.07(3H,s), 6.02(2H,s), 6.89(1H,s), 7.51(1H,s), 7.89(1H,s), 8.52(1H,t), 8.60–10.00(1H,br), 11.25(1H,s), 13.00–14.00(1H,br).

Example 10
2-[N-(2,4,5-Trimethoxybenzoyl)amino]-4-[(2-diethylaminoethyl)aminocarbonyl]-1,3-thiazole maleate MS(FAB,m/z): 437(MH$^+$); IR(KBr)cm$^{-1}$: 3380, 3331, 1664, 1610; $^1$H-NMR(DMSO-d$_6$)δ: 1.21(6H,t), 3.16–3.26 (6H,m), 3.57–3.64(2H,m), 3.93(3H,s), 4.07(3H,s), 4.20(3H, s), 6.01(2H,s), 6.89(1H,s), 7.51(1H,s), 7.89(1H,s), 8.51(1H, br), 11.24(1H,br), 13.00–14.00(1H,br).

Example 11
2-[N-(2,4,5-Trimethoxybenzoyl)amino]-4-[(2-diisopropylaminoethyl)aminocarbonyl]-1,3-thiazole maleate MS(EI,m/z): 464(M$^+$); IR(KBr)cm$^{-1}$: 3320, 1660, 1609; $^1$H-NMR(DMSO-d$_6$)δ: 1.29(12H,d), 3.18–3.77(6H,m), 3.79 (3H,s), 3.93(3H,s), 4.07(3H,s), 6.02(2H,s), 6.89(1H,s), 7.51 (1H,s), 7.89(1H,s), 8.50–8.55(2H,br), 13.00–14.00(1H,br).

Example 12
2-[N-(2,4,5-Trimethoxybenzoyl)amino]-4-[N-methyl-N-(2-diisopropylaminoethyl)aminocarbonyl]-1,3-thiazole maleate MS(EI,m/z): 478(M$^+$); IR(KBr)cm$^{-1}$: 3333, 1657, 1620; $^1$H-NMR(DMSO-d$_6$)δ: 1.15–1.43(12H,br), 3.05–3.78(12H, m), 3.92(3H,s), 4.04(3H,s), 6.03(2H,s), 6.87(1H,s), 7.46 (1H,br), 7.70(1H,s), 8.30–8.90(1H,br), 11.30–11.45(1H,m), 13.00–14.00(1H,br).

Example 13
2-[N-(2,4,5-Trimethoxybenzoyl)amino]-4-[[2-(N-isopropyl-N-methylamino)ethyl]aminocarbonyl]-1,3-thiazol MS(FAB,m/z): 437(MH$^+$); IR(KBr)cm$^{-1}$: 3220, 2965, 1657; $^1$H-NMR(CDCl$_3$)δ: 1.05(6H,d), 2.27(3H,s), 2.62(2H, t), 2.90(1H,m), 3.49(2H,dd), 3.93(3H,s), 3.99(3H,s), 4.11 (3H,s), 6.59(1H,s), 7.64(1H,brs), 7.74(1H,s), 7.78(1H,s), 11.05(1H,s).

Example 14
2-[N-(2,4,5-Trimethoxybenzoyl)amino]-4-[[2-(N-isopropyl-N-ethylamino)ethyl]aminocarbonyl]-1,3-thiazole dihydrochloride MS(FAB,m/z): 451(MH$^+$); IR(KBr)cm$^{-1}$: 3350, 2970, 1655, 1609; $^1$H-NMR(DMSO-d$_6$)δ: 1.27(9H,m), 3.16(4H, m), 3.64(3H,brs), 3.78(3H,s), 3.93(3H,s), 4.08(3H,s), 6.89 (1H,s), 7.51(1H,s), 7.90(1H,s), 8.69(1H,t), 10.11(1H,brs), 11.31(1H,s).

Example 15
2-[N-(2,4,5-Trimethoxybenzoyl)amino]-4-[[2-N-[2-(3,4-dimethoxyphenyl)ethyl]-N-methylamino]ethyl]aminocarbonyl]-1,3-thiazole MS(FAB,m/z): 559(MH$^+$); IR(neat)cm$^{-1}$: 3300, 3250, 1655; $^1$H-NMR(CDCl$_3$)δ: 2.38(3H,s), 2.66–2.75(4H,m), 3.53–3.56(2H,m), 3.76–3.86(2H,m), 3.80(3H,s), 3.85(3H,s), 3.91(3H,s), 3.97(3H,s), 4.04(3H,s), 6.56(1H,s), 6.75–6.82 (3H,m), 7.52(1H,br), 7.74–7.75(2H,m), 11.04(1H,br).

Example 16
2-[N-(2,4,5-Trimethoxybenzoyl)amino]-4-[[2-[N-(2-hydroxyethyl)-N-isopropylamino]ethyl]aminocarbonyl]-1,3-thiazole MS(FAB,m/z): 467(MH$^+$); IR(neat)cm$^{-1}$: 3322, 1655; $^1$H-NMR(CDCl$_3$)δ: 1.05(6H,d), 2.64(2H,t), 2.30(1H,br), 2.70(2H,t), 3.02(1H,quint), 3.47(2H,q), 3.61(2H,t), 3.92 (3H,s), 3.99(3H,s), 4.14(3H,s), 6.58(1H,s), 7.71(1H,br), 7.74(1H,s), 7.77(1H,s), 11.20(1H,brs).

Example 17
2-[N-(2,4,5-Trimethoxybenzoyl)amino]-4-[[2-(2-isooxazolynyl)ethyl]aminocarbonyl]-1,3-thiazole MS(FAB,m/z): 249(MH$^+$); IR(KBr)cm$^{-1}$: 3312, 1732, 1662; $^1$H-NMR(CDCl$_3$)δ: 2.35(2H,quint), 3.42(2H,t), 3.76–3.81(2H,m), 3.92(3H,s), 3.99(3H,s), 4.03(3H,s), 4.16 (2H,t), 6.58(1H,s), 7.77(1H,s), 7.87(1H,s), 11.12(1H,s)

Example 18
2-[N-(2,4,5-Trimethoxybenzoyl)amino]-4-[[2-(N-isopropylamino)ethyl]aminocarbonyl]-1,3-thiazole MS(FAB,m/z): 423(MH$^+$); IR(KBr)cm$^{-1}$: 3220, 2959, 1659, 1608; $^1$H-NMR(CDCl$_3$)δ: 1.09(6H,d), 2.86(3H,m), 3.54(2H,dd), 3.93(3H,s), 3.99(3H,s), 4.13(3H,s), 6.59(1H, s), 7.55(1H,t), 7.76(1H,s), 7.78(1H,s), 11.00(1H,brs).

Example 19
2-[N-(2,4,5-Trimethoxybenzoyl)amino]-4-[[2-[N-(ethoxycarbonylmethyl)-N-isopropyl]aminoethyl]-aminocarbonyl]-1,3-thiazole MS(FAB,m/z): 496(MH$^+$); IR(neat)cm$^{-1}$: 3346, 1743, 1655; $^1$H-NMR(CDCl$_3$)δ: 1.06(6H,d), 1.26(3H,t), 2.79(2H, t), 3.06(1H,quint), 3.33(2H,s), 3.48(2H,q), 3.93(3H,s), 3.99 (3H,s), 4.12(3H,s), 4.23(2H,q), 6.59(1H,s), 7.75(1H,s), 7.79 (1H,s), 7.89–7.91(1H,m), 11.10(1H,s).

Example 20
2-[N-(2,4,5-Trimethoxybenzoyl)amino]-4-[[2-[N-(hydroxycarbonylmethyl)-N-isopropyl]aminoethyl]-aminocarbonyl]-1,3-thiazole MS(FAB,m/z): 467(MH$^+$); IR(neat)cm$^{-1}$: 3307, 1655; $^1$H-NMR(DMSO-d$_6$)δ: 1.00(6H,d), 2.88(2H,t), 3.13(1H, quint), 3.15(2H,s), 3.48–3.52(2H,m), 3.78(3H,s), 3.92(3H, s), 4.05(3H,s), 6.87(1H,s), 7.48(1H,S), 7.88(1H,s), 8.53–8.56(1H,m), 8.73–8.76(1H,m), 12.23(1H,br).

Example 21
2-[N-(3,4-Dimethoxybenzoyl)amino]-4-[(3-dimethylaminopropyl)aminocarbonyl]-1,3-thiazole fumarate MS(FAB,m/z): 393(MH$^+$); IR(KBr)cm$^{-1}$: 3389, 1695; $^1$H-NMR(DMSO-d$_6$)δ: 1.74(2H,q), 2.33(6H,s), 3.17(2H,s), 3.32(2H,q), 3.85(3H,s), 3.87(3H,s), 6.51(1H,s), 7.11(1H,d), 7.77(2H,m), 7.97(1H,t).

Example 22
2-[N-(3,4-Dimethoxybenzoyl)amino]-4-[2-(1-piperazinyl)-ethylaminocarbonyl]-1,3-thiazole maleate A mixture of 10.0 g of 2-[N-(3,4-dimethoxybenzoyl)-amino]-4-(ethoxycarbonyl)-1,3-thiazole obtained in Referential Example 1 and 15.4 g of 2-(1-piperazinyl)ethylamine was stirred at 100° C. for 2 hours. The reaction mixture was subjected to distillation under reduced pressure. To the residue, 10 ml of methanol was added. The crystals so precipitated were collected by filtration. After conversion into a maleate, the resulting crystals were recrystallized from methanol, whereby 12.2 g of the title compound was obtained. Yield: 77%.

MS(FAB,m/z): 420(MH$^+$); IR(KBr)cm$^{-1}$: 3568, 3550, 3416, 1668; $^1$H-NMR(DMSO-d$_6$)δ: 2.49–2.63(4H,m), 3.07–3.10(2H,m), 3.31–3.46(6H,m), 3.86(3H,s), 3.87(3H,s), 6.02(2H,s), 7.12(1H,d), 7.72–7.83(4H,m), 8.47(1H,br), 12.50(1H,br), 13.00–14.00(2H,br).

Example 23
2-[N-(3,4-Dimethoxybenzoyl)amino]-4-[2-(4-methyl-1-piperazinyl)ethylaminocarbonyl]-1,3-thiazole hydrochloride In 30 ml of formic acid, 2.0 g of the compound obtained in Example 22 in the form of a free base was dissolved. To the resulting solution, 950 mg of 35% formaldehyde was added, followed by stirring at 80° C. for one hour. After allowed to cool down, the reaction mixture was subjected to distillation under reduced pressure. To the residue, 20 ml of ethanol was added, followed by the addition of a 4N hydrochloric acid—dioxane solution. The crystals so precipitated were collected by filtration. The crystals so obtained were recrystallized from methanol, whereby 1.6 g of the title compound was obtained. Yield: 59%.

MS (FAB,m/z): 434(MH$^+$); IR(KBr)cm$^{-1}$: 3280, 3200, 1655; $^1$H-NMR(DMSO-d$_6$)δ: 2.83(3H,s), 3.38–3.71(12H, m), 3.86(3H,s), 3.87(3H,s), 7.12(1H,d), 7.73–7.95(3H,m), 8.31(1H,br), 12.68(1H,br), 13.00–14.00(1H,br).

Example 24
2-[N-(3,4-Dimethoxybenzoyl)amino]-4-[2-[4-(2hydroxyethyl)-1-piperazinyl]ethylaminocarbonyl]-1,3-thiazole trihydrochloride In 30 ml of methanol, 2.0 g of the compound obtained in Example 22 in the form of a free base was suspended. To the resulting suspension, 1.4 g of a 40% aqueous solution of glyoxal was added, followed by stirring at room temperature for 3 hours. After ice cooling, the reaction mixture was added with 400 mg of sodium borohydride. The resulting mixture was stirred at room temperature for 12 hours. To the reaction mixture, 50 ml of water was added, followed by extraction with a mixed solution of chloroform and methanol. The organic layer was washed with 2N hydrochloric acid. By the addition of potassium carbonate, the water layer was made alkaline, followed by extraction with a mixed solution of chloroform and methanol. After drying through molecular sieves, the solvent was distilled off under reduced pressure. The residue was purified by chromatography on a silica gel column (chloroform:methanol=20:1). The compound so obtained was dissolved in 20 ml of ethanol, followed by the addition of a 4N hydrochloric acid—dioxane solution. The crystals so precipitated were collected by filtration, followed by recrystallization from ethanol, whereby 650 mg of the title compound was obtained. Yield: 27%.

MS(FAB,m/z): 464(MH$^+$); IR(KBr)cm$^{-1}$: 3300, 3225, 1676; $^1$H-NMP(DMSO$_6$)δ: 2.38–2.53(12H,m), 3.19–3.51 (5H,m), 3.86(3H,s), 3.87(3H,s), 7.09(1H,d), 7.52–7.77(4H, m), 11.00–11.50(1H,br), 13.00–14.00(3H,br).

Example 25
2-[N-(3,4-Dimethoxybenzoyl)amino]-4-[2-[(2-thiazolidinidene)imino]ethylaminocarbonyl]-1,3-thiazole A mixture of 5 g of the compound obtained in Example 2 in the form of a free base and 5.7 g of 2-methylthiothiazoline was stirred at 150° C. for one hour. After the reaction mixture was allowed to cool down, 50 ml of methanol was added. The crystals so precipitated were collected by filtration, whereby 3.63 g of the title compound was obtained. Yield: 58%.

MS(FAB,m/z): 436(MH$^+$); IR(KBr)cm$^{-1}$: 3400, 3000, 1642; $^1$H-NMR(CH$_3$OD)δ: 3.56–3.66(6H,m), 3.94(6H,s), 4.01(2H,t), 7.10(1H,d), 7.63(1H,d), 7.69(1H,dd), 7.82(1H, s).

In a similar manner to Example 25, compounds of Example 26 to 28 were prepared.

Example 26
2-[N-(3,4-Dimethoxybenzoyl)amino]-4-[2-[(2-pyrrolidinidene)imino]ethylaminocarbonyl]-1,3-thiazol hydroiodide MS(FAB,m/z): 418(MH$^+$); IR(KBr)cm$^{-1}$: 3420, 3083, 1649, 1618; $^1$H-NMR(DMSO-d$_6$)δ: 2.03(2H,q), 2.78(2H,t), 3.41–3.63(6H,m), 3.85(3H,s), 3.86(3H,s), 7.12(1H,d), 7.71 (1H,d), 7.76(1H,dd), 7.86(1H,s), 8.06(1H,brs), 9.55(2H, brs), 12.57(1H,brs).

Example 27
2-[N-(3,4-Dimethoxybenzoyl)amino]-4-[2-[(2-oxazolidinidene)imino]ethylaminocarbonyl]-1,3-thiazol MS(FAB,m/z): 420(MH$^+$); IR(KBr)cm$^{-1}$: 3380, 2910, 1643; $^1$H-NMR(DMSO-d$_6$)δ: 3.34(2H,t), 3.54(2H,t), 3.70 (2H,t), 3.92(3H,s), 3.93(3H,s), 4.29(2H,t), 7.08(1H,d), 7.63 (1H,d), 7.68(1H,q), 7.76(1H,s).

Example 28
2-[N-(3,4-Dimethoxybenzoyl)amino]-4-[2-[(2-imidazolidinidene)imino]ethylaminocarbonyl]-1,3-thiazole hydrochloride MS(FAB,m/z): 419(MH$^+$); IR(KBr)cm$^{-1}$: 3389, 3197, 1676; $^1$H-NMR(DMSO-d$_6$)δ: 3.17(1H,s), 3.31(2H,m), 3.40 (2H,brs), 3.57(4H,s), 3.78(3H,s), 3.79(3H,s), 6.92(1H,d), 7.26(1H,s), 7.68(2H,m), 8.31(1H,br).

Example 29
2-[N-(3,4-Dimethoxybenzoyl)amino]-4-[(4-dimethylaminobutyl)aminocarbonyl]-1,3-thiazole dihydrochloride To 5 g of the compound obtained in Referential Example 1, 13.1 g of 1,4-butanediamine was added, followed by stirring at 100° C. for 2 hours. The reaction mixture was subjected to distillation under reduced pressure. To the residue, water was added. The resulting mixture was extracted with a mixed solution of chloroform and methanol, followed by drying through molecular sieves. The solvent was then distilled off, whereby 4.5 g of 2-[N-(3,4-dimethoxybenzoyl)amino]-4-[(4-aminobutyl)aminocarbonyl]-1,3-thiazole was obtained.

Then, the compound so obtained was dissolved in 45 ml of formic acid. Under ice cooling, 2.3 g of a 35% aqueous solution of formaldehyde was added to the resulting solution, followed by reflux for one hour. After the reaction mixture was subjected to distillation under reduced pressure, the residue was neutralized with an aqueous solution of sodium bicarbonate, followed by extraction with a mixed solution of chloroform and methanol. The extract was dried through molecular sieves and the solvent was distilled off under reduced pressure. The residue so obtained was purified by chromatography on a silica gel column (chloroform:methanol=50:1), whereby 1.0 g of the title compound was obtained in the form of a free base. The compound was converted into its dihydrochloride and thus, the title compound was obtained.

MS(FAB,m/z): 407(MH$^+$); IR(KBr)cm$^{-1}$: 3350, 3245, 1601; $^1$H-NMR(DMSO-d$_6$)δ: 1.55(2H,m), 1.64(2H,m), 2.70 (3H,s), 2.72(3H,s), 3.03(2H,m), 3.30(2H,m), 3.85(3H,s), 3.87(3H,s), 7.12(1H,d), 7.73–7.80(2H,m), 7.85(1H,s), 7.97 (1H,t), 10.48(1H,br), 12.64(1H,br).

Example 30
2-[N-(2,4,5-Trimethoxybenzoyl)amino]-4-[(2-dimethylaminoethoxy)carbonyl]-1,3-thiazole In 10 ml of N,N-dimethylformamide, 278 mg of sodium hydride was suspended. To the resulting suspension, 620 mg of N,N-dimethylaminoethanol was added dropwise, followed by stirring at room temperature for one hour. In another 10 ml portion of N,N-dimethylformamide, 1.57 g of 2-[N-(2,4,5-trimethoxybenzoyl)amino]-4-(hydroxycarbonyl)-1,3-thiazole was suspended. To the resulting suspension, 827 mg of carbonyl diimiazole was added, followed by stirring at room temperature for one hour. Two reaction mixtures so obtained were combined and were stirred at 100° C. for one hour. The reaction mixture was poured into an ice water and the crystals so precipitated were collected by filtration. The crystals so obtained were recrystallized from isopropyl alcohol, whereby 1.4 g of the title compound was obtained. Yield: 74%.

MS(FAB,m/z): 410(MH$^+$); IR(KBr)cm$^{-1}$: 3316, 1727, 1655; $^1$H-NMR(CDCl$_3$)δ: 2.35(6H,s), 2.73(2H,t), 3.92(3H, s), 3.99(3H,s), 4.10(3H,s), 4.46(2H,t), 6.58(1H,s), 7.77(1H, s), 7.86(1H,t), 11.14(1H,brs).

In a similar manner to Example 30, compounds of Example 31 to 33 which will be described later were prepared.

Example 31
2-[N-(2,4,5-Trimethoxybenzoyl)amino]-4-[(2-diethylaminoethoxy)carbonyl]-1,3-thiazole MS(FAB,m/z): 438(MH$^+$); IR(KBr)cm$^{-1}$: 3308, 1721, 1659; $^1$H-NMR(CDCl$_3$)δ: 1.07(6H,t), 2.63(4H,q), 2.86(2H, t), 3.92(3H,s), 3.98(3H,s), 4.09(3H,s), 4.42(2H,t), 6.58(1H, s), 7.77(1H,s), 7.83(1H,s), 11.13(1H,brs).

Example 32
2-[N-(2,4,5-Trimethoxybenzoyl)amino]-4-[(2-diisopropylaminoethoxy)carbonyl]-1,3-thiazole MS(FAB,m/z): 466(MH$^+$); IR(KBr)cm$^{-1}$: 3306, 1721, 1655; $^1$H-NMR(CDCl$_3$)δ: 1.04(12H,d), 2.80(2H,t), 3.04 (2H,q), 3.92(3H,s), 3.99(3H,s), 4.09(3H,s), 4.28(2H,t), 6.58 (1H,s), 7.77(1H,s), 7.84(1H,s), 11.13(1H,brs).

Example 33
2-[N-(3,4-Dimethoxybenzoyl)amino]-4-[(2-dimethylaminoethoxy)carbonyl]-1,3-thiazole MS(FAB,m/z): 380(MH$^+$); IR(KBr)cm$^{-1}$: 3245, 1738, 1680; $^1$H-NMR(CDCl$_3$)δ: 2.31(6H,s), 2.68(2H,t), 3.94(3H, s), 3.96(3H,s), 4.38(2H,t), 6.94(1H,d), 7.48–7.53(2H,m), 7.87(1H,s), 9.50(1H,brs).

In a similar manner to Referential Example 1 except that 3,4-dimethoxybenzoyl chloride was replaced by a corresponding 3-substituted benzoyl chloride, an intermediate was prepared. In a similar manner to Example 2, compounds of Examples 34 to 41, which will be described below, were prepared using the intermediate so obtained.

Example 34
2-[N-(2-Amino-4,5-dimethoxybenzoyl)amino]-4-[(2-dimethylaminoethyl)aminocarbonyl]-1,3-thiazole dihydrochloride MS (FAB,m/z): 394(MH$^+$); IR(KBr)cm$^{-1}$: 3393, 2955, 1655, 1526, 1296; $^1$H-NMR(DMSO-d$_6$)δ: 2.80(3H,s), 2.82 (3H,s), 3.26(2H,q), 3.68(2H,q), 3.80(3H,s), 3.82(3H,s), 4.40–6.40(4H,br), 6.83(1H,s), 7.53(1H,s), 7.98(1H,s), 8.43 (1H,t), 10.59(1H,brs).

Example 35
2-[N-(4,5-Dimethoxy-2-nitrobenzoyl)amino]-4-[(2-dimethylaminoethyl)aminocarbonyl]-1,3-thiazole MS(FAB,m/z): 424(MH$^+$); IR(KBr)cm.$^{-1}$: 3428, 1663, 1549, 1522, 1298; $^1$H-NMR(DMSO-d$_6$)δ: 2.20(6H,s), 2.43 (2H,t), 3.37(2H,q), 3.93(6H,s), 7.36(1H,s), 7.70(2H,m), 7.84(1H,s).

Example 36
2-[N-(2-Bromo-4,5-dimethoxybenzoyl)amino]-4-[(2-dimethylaminoethyl)aminocarbonyl]-1,3-thiazole MS (FAB,m/z): 457(MH$^+$); IR(KBr)cm$^{-1}$: 3410, 1672, 1657, 1545, 1507, 1269; $^1$H-NMR(CDCl$_3$)δ: 2.22(6H,s), 2.57(2H,t), 3.54(2H,q); 3.91(3H,s), 3.94(3H,s), 7.09(1H,s), 7.36(1H,s), 7.57(1H,t), 7.76(1H,s).

Example 37
2-[N-(4,5-Dimethoxy-2-hydroxybenzoyl)amino]-4-[(2-dimethylaminoethyl)aminocarbonyl]-1,3-thiazole MS(FAB,m/z): 395(MH$^+$); IR(KBr)cm$^{-1}$: 3401, 1655, 1549, 1491, 1244, 1217, 1206 $^1$H-NMR(CDCl$_3$)δ: 2.58(6H, s), 2.93(2H,t), 3.48(2H,q), 3.72(3H,s), 3.75(3H,s), 6.43(1H, s), 7.42(1H,s), 7.59(IH,s), 8.25(1H,t).

Example 38
2-[N-(4,5-Dimethoxy-2-hydroxybenzoyl)amino]-4-[(2-diisopropylaminoethyl)aminocarbonyl]-1,3-thiazole A mixture of 15.4 g of 2-[N-(4,5-dimethoxy-2-hydroxybenzoyl)amino]-4-(ethoxycarbonyl)-1,3-thiazole acetate obtained in Referential Example 6 and 26.9 g of diisopropylethylenediamine was stirred at 120° C. for 30 minutes under an argon gas stream. The reaction mixture was subjected to distillation under reduced pressure. To the residue, chloroform was added for dilution, followed by washing with water. The chloroform layer was dried over sodium sulfate. The solvent was distilled off under reduced pressure, whereby 11.7 g of the title compound was obtained. Yield: 69%.

MS(FAB,m/z): 451(MH$^+$); IR(KBr)cm$^{-1}$: 3401, 1661, 1522, 1267; $^1$H-NMR(DMSO-d$_6$)δ: 1.32(12H,m), 3.16(2H, m), 3.63(4H,m), 3.77(3H,s), 3.82(3H,s), 6.84(1H,s), 7.50 (1H,s), 7.89(1H,s), 8.71(1H,t), 9.56(1H,br), 11.79(1H,brs), 12.00(1H,br).

In addition, 11.7 g of the title compound was dissolved in isopropyl alcohol. A hydrochloric acid gas was blown into the resulting solution under ice cooling. The crystals so precipitated were collected by filtration, followed by recrystallization from a mixed solvent of isopropyl alcohol and water, whereby 14.0 of the hydrochloride of the title compound was obtained.

Example 39
2-[N-(4,5-Dimethoxy-2-dimethylaminobenzoyl)amino]-4-[(2-dimethylaminoethyl)aminocarbonyl]-1,3-thiazole dihydrochloride MS(FAB,m/z): 422(MH$^+$); IR(KBr)cm$^{-1}$: 3410, 1526, 1422, 1339, 1294; $^1$H-NMR(DMSO$_6$)δ: 2.81(3H,s), 2.83 (3H,s), 3.12(6H,s), 3.28(2H,q), 3.68(2H,q), 3.94(3H,s), 4.80 (3H,s), 7.49(1H,s), 7.67(1H,s), 8.05(1H,s), 8.99(1H,brs), 10.70(1H,brs).

Example 40
2-[N-(4,5-Dimethoxy-2-methylbenzoyl)amino]-4-[(2-dimethylaminoethyl)aminocarbonyl]-1,3-thiazole MS(FAB,m/z): 393(MH$^+$); IR(KBr)cm$^{-1}$: 3474, 2983, 1674, 1561, 1271, 1146; $^1$H-NMR(CDCl$_3$)δ: 2.15(6H,s), 2.50(3H,s), 2.55(2H,t), 3.53(2H,q), 3.91(3H,s), 3.93(3H,s), 6.76(1H,s), 7.22(1H,s), 7.62(1H,t), 7.71(1H,s).

Example 41
2-[N-(4,5-Dimethoxy-2-acetylaminobenzoyl)amino]-4-[(2-dimethylaminoethyl)aminocarbonyl]-1,3-thiazole MS(FAB, m/z): 436(MH$^+$); IR(KBr)cm$^{-1}$: 3565, 1650, 1555, 1534, 1292; $^1$H-NMR(CDCl$_3$)δ: 2.24(9H,s), 2.57(2H, t), 3.50(2H,q), 3.76(3H,s), 3.99(3H,s), 7.38(1H,s), 7.62(1H, t), 7.74(1H,s), 8.43(1H,s).

Example 42
2-[N-(Benzoyl)amino]-4-[(2-dimethylaminoethyl) aminocarbonyl]-1,3-thiazole hydrochloride MS(EI,m/z): 318(M$^+$); IR(KBr)cm$^{-1}$: 3400, 1669, 1644; $^1$H-NMR(DMSO-d$_6$)δ: 2.81(6H,d), 3.24–3.30(2H,m), 3.65–3.72(2H,m), 7.53–7.70(3H,m), 8.00–8.41(4H,m), 10.58(1H,brs), 12.84(1H,s).

Example 43
2-[N-(2-Methoxybenzoyl)amino]-4-[(2-dimethylaminoethyl)-aminocarbonyl]-1,3-thiazole maleate IR(KBr)cm$^{-1}$: 3320, 3050, 1660, 1610, 1570, 1540 $^1$H-NMR(DMSO-d$_6$)δ: 2.83(6H,s), 2.76(2H,q), 3.61(2H,q), 3.98(3H,s), 6.02(2H,s), 7.13(1H,t), 7.27(1H,d), 7.58–7.63 (2H,m), 7.84(1H,dd), 7.93(1H,s), 9.30(2H,brs), 11.67(1H,s)

Example 44
2-[N-(3-Methoxybenzoyl)amino]-4-[(2-dimethylaminoethyl)-aminocarbonyl]-1,3-thiazole dihydrochloride IR(KBr)cm$^{-1}$: 3400, 3200, 2966, 2689, 1690, 1670, 1580, 1560, 1520; $^1$H-NMR(DMSO-d$_6$)δ: 2.80(3H,s), 2.82(3H,s), 3.26(2H,q), 3.68(2H,q), 3.86(3H,s), 6.91(1H,brs), 7.71–7.24 (1H,m), 7.47(1H,t), 7.65–7.70(2H,m), 8.01(1H,s), 8.39(1H, t), 10.68(1H,brs), 12.84(1H,brs).

Example 45
2-[N-(3-Chlorobenzoyl)amino]-4-[(2-dimethylaminoethyl)-aminocarbonyl]-1,3-thiazole maleate IR(KBr)cm$^{-1}$: 3300, 1669, 1659, 1541; $^1$H-NMR (DMSO-d$_6$)δ: 2.83(6H,s), 3.24(2H,t), 3.31(3H,brs), 3.63 (2H,m), 6.02(2H,s), 7.60(1H,t), 7.72(1H,m), 7.93(1H,s), 8.04(1H,m), 8.15(1H,m), 8.21(1H,t).

Example 46
2-[N-(4-Methoxybenzoyl)amino]-4-[(2-dimethylaminoethyl)-aminocarbonyl]-1,3-thiazole dihydrochloride IR(KBr)cm$^{-1}$: 3400, 3150, 3050, 2950, 2700, 1670, 1655, 1603; $^1$H-NMR(DMSO-d$_6$)δ: 2.80(3H,s), 2.82(3H,s), 3.25 (2H,q), 3.68(2H,q), 3.85(3H,s), 4.68(1H,s), 7.05–7.15(2H, m), 7.96(1H,s), 8.01–8.15(2H,m), 8.36(1H,t), 10.54(1H,s), 12.64 (1H, s)

Example 47
2-[N-(2,3-Dimethoxybenzoyl)amino]-4-[(2-dimethylaminoethyl)aminocarbonyl]-1,3-thiazole maleate MS(EI,m/z): 318(M$^+$); IR(KBr)cm$^{-1}$: 3403, 3297, 1671, 1580; $^1$H-NMR(DMSO-d$_6$)δ: 2.83(6H,s), 3.25(2H,t), 3.61 (2H,q), 3.88(3H,s), 3.89(3H,s), 6.02(2H,s), 7.20–7.33(3H, m), 7.91(1H,s), 8.35(1H,t), 9.00–10.00(2H,br), 12.00(1H, brs).

Example 48
2-[N-(2-Hydroxy-3-methoxybenzoyl)amino]-4-[(2-dimethylaminoethyl)aminocarbonyl]-1,3-thiazole maleate MS(EI,m/z): 304(M$^+$); IR(KBr)cm$^{-1}$: 3400, 1660, 1551; $^1$H-NMR(DMSO-d$_6$)δ: 2.83(6H,s), 3.26(2H,t), 3.60(2H,q), 3.89(3H,s), 6.03(2H,s), 6.94(1H,t), 7.22(1H,dd), 7.59(1H, dd), 7.85(1H,s), 8.54(1H,t), 9.00–12.00(3H,br).

Example 49
2-[N-(4-Hydroxy-2-methoxybenzoyl)amino]-4-[(2-diisopropylaminoethyl)aminocarbonyl]-1,3-thiazole dihydrochloride $^1$H-NMR(DMSO-d$_6$)δ: 1.29–1.33(12H,m), 2.47–2.51 (2H,m), 3.19–3.58(4H,m), 3.59–3.76(2H,m), 3.97(3H,s), 6.82(1H,s), 7.87(1H,s), 7.90(1H,s), 8.53–8.68(1H,m), 9.09–9.23(1H,m), 11.28(1H,s), 11.41(1H,s).

Example 50
2-[N-(2-Hydroxy-4-methoxybenzoyl)amino]-4-[(2-diisopropylaminoethyl)aminocarbonyl]-1,3-thiazole $^1$H-NMR(CDCl$_3$)δ: 1.22(12H,d), 2.88–2.91(2H,m), 3.25–3.31(2H,m), 3.61–3.65(2H,m), 3.82(3H,s), 6.41–6.50 (2H,m), 7.69(1H,s), 7.81–7.84(1H,m), 8.07(1H,d), 10.82 (1H,s), 11.43(1H,s).

Example 51
2-[N-(2,5-Dimethoxybenzoyl)amino]-4-[(2-dimethylaminoethyl)aminocarbonyl]-1,3-thiazole maleate MS(EI,m/z): 378(M$^+$); IR(KBr)cm$^{-1}$: 3305, 1661; $^1$H-NMR(DMSO$_6$)δ: 2.84(6H,s), 3.26(2H,t), 3.61(2H,q), 3.79(3H,s), 3.96(3H,s), 6.02(2H,s), 7.18–7.43(3H,m), 7.91 (1H,s), 8.43(1H,t), 8.50–11.00(2H,br), 11.63(1H,brs).

Example 52
2-[N-(2,6-Dimethoxybenzoyl)amino]-4-[(2-dimethylaminoethyl)aminocarbonyl]-1,3-thiazole maleate MS(EI,m/z): 318(M$^+$); IR(KBr)cm$^{-1}$: 3303, 1661, 1599; $^1$H-NMR(DMSO-d$_6$)δ: 2.81(6H,s), 3.23(2H,t), 3.61(2H,q), 3.76(6H,s), 6.02(2H,s), 6.75(2H,d), 7.40(1H,t), 7.85(1H,s), 8.13(1H,t), 9.00–9.50(2H,br), 12.40(1H,brs).

Example 53
2-[N-(3,5-Dimethoxybenzoyl)amino]-4-[(2-dimethylaminoethyl)aminocarbonyl]-1,3-thiazole hydrochloride IR(KBr)cm$^{-1}$: 3600, 3250, 3100, 1650, 1637, 1601
$^1$H-NMR(DMSO-d$_6$)δ: 2.80(3H,s), 2.82(3H,s), 3.30–3.60 (2H,m), 3.60–3.75(2H,m), 3.83(6H,s), 6.75(1H,s), 7.28(1H, s), 7.29(1H,s), 7.99(1H,s), 8.30–8.40(1H,m), 10.38(1H,brs), 12.79(1H,s).

Example 54
2-[N-(3,4-Dimethoxybenzoyl)amino]-4-[(2-methylaminoethyl)aminocarbonyl]-1,3-thiazole dihydrochloride IR(KBr)cm$^{-1}$: 3450, 1674, 1601, 1560; $^1$H-NMR (DMSO$_6$)δ: 2.57(3H,t), 3.08(2H,t), 3.63(2H,q), 3.86(3H,s), 3.87(3H,s), 4.88(1H,brs), 7.12(1H,d), 7.74–7.80(2H,m), 7.96(1H,s), 8.28(1H,t), 9.11(2H,brs), 12.70(1H,brs).

Example 55
2-[N-(3,4-Dimethoxybenzoyl)amino]-4-[N-(2-methylaminoethyl)-N-methylaminocarbonyl]-1,3-thiazole dihydrochloride IR(KBr)cm$^{-1}$: 3450, 1680, 1636, 1559, 1279;
$^1$H-NMR(CD$_3$OD)δ: 3.20(6H,s), 3.88(3H,s), 3.91(3H,s), 3.99(4H,s), 6.99(1H,d), 7.59(1H,s), 7.80(1H,dd), 7.84(1H, d).

Example 56
2-[N-(3,4-Dimethoxybenzoyl)amino]-4-[(2-isopropylaminoethyl)aminocarbonyl]-1,3-thiazole maleate $^1$H-NMR(CDCl$_3$)δ: 1.42(6H,d), 3.26–3.39(2H,m), 3.45–3.51(1H,m), 3.68–3.79(2H,m), 3.89(3H,s), 3.93(3H,s), 6.26(2H,s), 6.94–6.97(1H,m), 7.58(1H,s), 7.59(1H,s), 7.93 (1H,d), 8.84–8.91(1H,m), 9.39(2H,s), 11.10(1H,s).

Example 57
2-[N-(4-Hydroxy-3-methoxybenzoyl)amino]-4-[(2-diisopropylaminoethyl)aminocarbonyl]-1,3-thiazole dihydrochloride $^1$H-NMR(DMSO-d$_6$)δ: 1.30–1.37(12H,m), 3.16–3.20 (2H,m), 3.59–3.67(4H,m), 3.82(1H,s), 3.87(3H,s), 6.91–6.94(1H,m), 7.61–7.65(1H,m), 7.72(1H,s), 7.91(1H,s), 8.40–8.45(1H,m), 9.97–9.99(2H,m), 12.55(1H,s).

Example 58
2-[N-(3-Hydroxy-4-methoxybenzoyl)amino]-4-[(2-diisopropylaminoethyl)aminocarbonyl]-1,3-thiazole dihydrochloride $^1$H-NMR(DMSO-d$_6$)δ: 1.30–1.37(12H,m), 3.13–3.18 (2H,m), 3.57(1H,s), 3.56–3.65(4H,m), 3.86(3H,s), 7.04–7.07(1H,m), 7.51(1H,s), 7.63–7.67(1H,m), 7.90(1H,s), 8.41–8.50(1H,m), 9.94–9.99(2H,m), 12.51(1H,s).

Example 59
2-[N-(3,4-Dimethoxybenzoyl)amino]-4-[[2-(N-2-pyridylamino)ethyl]aminocarbonyl]-1,3-thiazole hydrochloride MS (FAB,m/z): 428(MH$^+$); $^1$H-NMR(DMSO-d$_6$)δ: 3.60 (2H,brs), 3.76(2H,brs), 3.85(3H,s), 3.87(3H,s), 6.82–6.87 (1H,m), 7.08–7.14(2H,m), 7.73–7.79(2H,m), 7.85–7.92(2H, m), 8.10(1H,brs), 9.09(1H,brs), 12.67(1H,s), 14.09(2H,brs).

Example 60
2-[N-(3,4-Dimethoxybenzoyl)amino]-4-[[2-(1-pyrrolidyl)ethyl]aminocarbonyl]-1,3-thiazole maleate MS(FAB,m/z): 405(MH$^+$); IR(KBr)cm$^{-1}$: 3450, 1669, 1545, 1515; $^1$H-NMR(CD$_3$OD)δ: 2.10(4H,brs), 3.30–3.32 (4H,m), 3.46(2H,t), 3.87(2H,t), 3.92(3H,s), 3.93(3H,s), 6.23 (2H,s), 7.09(1H,d), 7.61(1H,d), 7.68(1H,dd), 7.83(1H,s).

Example 61
2-[N-(3,4-Dimethoxybenzoyl)amino]-4-[[2-(1-piperidyl)ethyl]aminocarbonyl]-1,3-thiazole dihydrochloride MS(FAB,m/z): 419(MH$^+$); IR(KBr)cm$^{-1}$: 3300, 1675, 1665, 1605, 1555, 1534; $^1$H-NMR(CD$_3$OD)δ: 1.45–2.05 (6H,m), 2.90–3.10(2H,m), 3.41(2H,t), 3.63–3.81(4H,m), 3.93(6H,s), 6.26(2H,s), 7.10(1H,d), 7.61(1H,d), 7.69(1H dd), 7.84(1H,s).

Example 62
2-[N-(3,4-Dimethoxybenzoyl)amino]-4-[[2-(2-pyrrolidon-1yl)ethyl]aminocarbonyl]-1,3-thiazole IR(KBr)cm$^{-1}$: 3411, 1684, 1650, 1603; $^1$H-NMR(DMSO-d$_6$)δ: 1.91(2H,quint), 2.18(2H,t), 3.30–3.50(6H,m), 3.85 (3H,s), 3.87(3H,s), 7.11(1H,d), 7.70–7.80(2H,m), 7.83(1H, s), 7.91(1H,t), 12.63(1H,s).

Example 63
2-[N-(3,4-Dimethoxybenzoyl)amino]-4-[[2-(2-piperidon-1yl)ethyl]aminocarbonyl]-1,3-thiazole IR(KBr)cm$^{-1}$: 3450, 1650, 1613, 1551, 1518; $^1$H-NMR (DMSO-d$_6$)δ: 1.60–1.80(4H,m), 2.18(2H,t), 3.25–3.40(2H, m), 3.40–3.50(4H,m), 3.85(3H,s), 3.87(3H,s), 7.11(1H,d), 7.70–7.79(3H,m), 7.80(1H,s), 7.95(1H,brs)

Example 64
2-[N-(3,4-Dimethoxybenzoyl)amino]-4-[(2-guanidinoethyl) aminocarbonyl]-1,3-thiazole hydrochloride MS(FAB,m/z): 393(MH$^+$); IR(KBr)cm$^{-1}$: 3160, 1663, 1603, 1565, 1532; $^1$H-NMR(DMSO-d$_6$)δ: 3.32–3.46(4H, m), 3.86(3H,s), 3.87(3H,s), 6.52(2H,brs), 7.10–7.65(3H,m), 7.73–7.79(2H,m), 7.86–7.90(2H,m), 8.03–8.07(1H,m), 12.67(1H,brs)

Example 65
2-[N-(3,4-Dimethoxybenzoyl)amino]-4-[2-[3-(1-methylthioureido)ethyl]aminocarbonyl]-1,3-thiazole dihydrochloride $^1$H-NMR(DMSO-d$_6$)δ: 2.79–2.98(2H,m), 3.57(3H,s), 3.62–3.73(2H,m), 3.85(3H,s), 3.86(3H,s), 5.19–5.74(2H,s), 7.12(1H,s), 7.73–7.78(2H,m), 7.94(1H,s), 8.19–8.29(1H,m), 8.92–9.08(1H,m), 10.02–10.31(1H,m), 12.49–12.78(1H,m).

Example 66
2-[N-(3,4-Dimethoxybenzoyl)amino]-4-[[2-[3-(1,2-dimethyl)thioureido]ethyl]aminocarbonyl]-1,3-thiazole dihydrochloride $^1$H-NMR(CDCl$_3$)δ: 2.38(3H,s), 2.95(3H,s), 3.47–3.53 (2H,m), 3.58–3.63(2H,m), 3.97(6H,s), 5.55(4H,brs), 6.96–6.99(1H,m), 7.66–7.74(4H,m).

Example 67
2-[N-(2,3,4-Trimethoxybenzoyl)amino]-4-[(2-dimethylaminoethyl)aminocarbonyl]-1,3-thiazole maleate IR(KBr)cm$^{-1}$: 3400, 3300, 1660; $^1$H-NMR(DMSO-d$_6$)δ: 2.82(6H,s), 3.24(2H,t), 3.58(2H,q), 3.82(3H,s), 3.89(3H,s), 3.99(3H,s), 6.01(2H,s), 7.03(1H,d), 7.65(1H,d), 7.89(1H,s), 8.44(1H,t), 9.25(2H,brs), 11.56(1H,s).

Example 68
2-[N-(2,3,5-Trimethoxybenzoyl)amino]-4-[(2-dimethylaminoethyl)aminocarbonyl]-1,3-thiazole maleate MS(EI,m/z): 348(M$^+$); IR(KBr)cm$^{-1}$: 3306, 1667, 1607; $^1$H-NMR(DMSO-d$_6$)δ: 2.83(6H,s), 3.25(2H,t), 3.61(2H,q), 3.80(3H,s), 3.81(3H,s), 3.87(3H,s), 6.02(2H,s), 6.85(1H,d), 6.88(1H,d), 7.92(1H,s), 8.37(1H,t), 9.00–9.50(2H,br), 11.98 (1H,brs).

Example 69
2-[N-(2,3,6-Trimethoxybenzoyl)amino]-4-[(2-dimethylaminoethyl)aminocarbonyl]-1,3-thiazole maleate MS(EI,m/z): 348(M$^+$); IR(KBr)cm$^{-1}$: 3000, 1682, 1650; $^1$H-NMR(DMSO-d$_6$)δ: 2.82(6H,s), 3.23(2H,t), 3.61(2H,q), 3.72(3H,s), 3.74(3H,s), 3.80(3H,s), 6.02(2H,s), 6.80(1H,d), 7.11(1H,d), 7.87(1H,s), 8.15(1H,t), 8.80–10.00(2H,br), 12.51(1H,brs).

Example 70

2-[N-(2,4,6-Trimethoxybenzoyl)amino]-4-[(2-dimethylaminoethyl)aminocarbonyl]-1,3-thiazole maleate IR(KBr)cm$^{-1}$: 3400, 2360, 1670; $^1$H-NMR(CDCl$_3$)δ: 2.84(6H,s), 3.25(2H,t), 3.61(2H,t), 3.76(6H,s), 3.83(3H,s), 6.01(2H,s), 6.30(2H,s), 7.82(1H,s), 8.13(1H,t), 9.25(2H,brs), 12.24(1H,s).

Example 71

2-[N-(3,4,5-Trimethoxybenzoyl)amino]-4-[(2-dimethylaminoethyl)aminocarbonyl]-1,3-thiazole fumarate IR(KBr)cm$^{-1}$: 3300, 1670, 1590, 1550; $^1$H-NMR (DMSO-d$_6$)δ: 2.31(6H,s), 2.58(2H,t), 3.46(2H,q), 3.76(3H,s), 3.89(6H,s), 6.58(2H,s), 7.49(2H,s), 7.81(1H,t), 7.85(1H,s).

Example 72

2-[N-(2,4,5-Trimethoxybenzoyl)amino]-4-[(2-cyclopropylaminoethyl)aminocarbonyl]-1,3-thiazole MS(FAB,m/z): 421(MH$^+$); IR(KBr)cm$^{-1}$: 1653, 1512, 1259, 1024; $^1$H-NMR(CDCl$_3$)δ: 0.36–0.53(4H,m), 2.20(1H, ddd), 2.97(2H,t), 3.56(2H,q), 3.93(3H,s), 4.00(3H,s), 4.14(3H,s), 6.59(1H,s), 7.48(1H,t), 7.76(1H,s), 7.78(1H,s), 11.05(1H,s).

Example 73

2-[N-(2,4,5-Trimethoxybenzoyl)amino]-4-[(2-tert-butylaminoethyl)aminocarbonyl]-1,3-thiazole dihydrochloride $^1$H-NMR(DMSO-d$_6$)δ: 1.30(9H,s), 2.98–3.09(2H,m), 3.17(1H,s), 3.53–3.70(2H,m), 3.78(3H,s), 3.93(3H,s), 4.08(3H,s), 6.89(1H,s), 7.50(1H,s), 7.90(1H,s), 8.49–8.63(1H,m), 8.82–9.00(2H(m), 11.32(1H,s).

Example 74

2-[N-(2,4,5-Trimethoxybenzoyl)amino]-4-[(3-diisopropylaminopropyl)aminocarbonyl]-1,3-thiazole dihydrochloride MS(FAB,m/z): 479(MH$^+$); IR(KBr)cm$^{-1}$: 3410, 1674, 1663, 1611, 1584, 1553, 1520; $^1$H-NMR(CDCl$_3$)δ: 1.27–1.34(12H,m), 2.00–2.06(2H,m ), 3.06–3.10(2H,m), 3.29–3.36(2H,m), 3.56–3.62(2H,m), 3.78(3H,s), 3.93(3H,s), 4.07(3H,s), 6.88(1H,s), 7.49(1H,s), 7.87(1H,s), 8.47(1H,brs), 9.92(2H,brs), 11.33(1H,s).

Example 75

2-[N-(2,4,5-Trimethoxybenzoyl)amino]-4-[[N-(2-diethylaminoethyl)-N-methyl]aminocarbonyl]-1,3-thiazole maleate IR(KBr)cm$^{-1}$: 3400, 3320, 1640, 1625; $^1$H-NMR(CDCl$_3$)δ: 1.23(6H,t), 3.14(3H,s), 3.15(2H,q), 3.29(2H,t), 3.76(3H,s), 3.77(4H,q), 3.92(3H,s), 4.03(3H,s), 6.02(2H,s), 6.86(3H,s), 7.49(1H,s), 7.65(1H,s), 9.50(2H,brs), 11.26(1H,s).

Example 76

2-[[N-Methyl-N-(2,4,5-trimethoxybenzoyl)amino]-4-[(2-dimethylaminoethyl)aminocarbonyl]-1,3-thiazole maleate IR(KBr)cm$^{-1}$: 3300, 1655; $^1$H-NMR(CDCl$_3$)δ: 2.91(6H,s), 3.33–3.38(2H,m), 3.55(3H,s), 3.81–3.99(2H,m), 3.84(3H,s), 3.88(3H,s), 3.96(3H,s), 6.16(2H,s), 6.55(1H,s), 6.95(1H,s), 7.83(1H,s), 8.12(1H,t), 12.50(2H,brs).

Example 77

2-[[N-Methyl-N-(2,4,5-trimethoxybenzoyl)amino]-4-[(2-diisopropylaminoethyl)aminocarbonyl]-1,3-thiazole maleate IR(KBr)cm$^{-1}$: 3300, 1655, 1541; $^1$H-NMR(CDCl$_3$)δ: 1.37(6H,d), 1.41(6H,d), 3.25–3.35(2H,m), 3.52(3H,s), 3.58–3.68(2H,m), 3.85(3H,s), 3.86(3H,s), 3.83–3.89(2H,m), 3.97(3H,s), 6.26(2H,s), 6.56(1H,s), 6.91(1H,s), 7.82(1H,s), 8.88(1H,t), 10.70(1H,s).

Example 78

2-[N-(2,4,5-Trimethoxybenzoyl)amino]-4-[(2-di-n-propylaminoethyl)aminocarbonyl]-1,3-thiazole dihydrochloride IR(KBr)cm$^{-1}$: 3400, 1663, 1611, 1550; $^1$H-NMR(DMSO-d$_6$)δ: 0.91(6H,t), 1.65–1.80(4H,m), 3.00–3.10(4H,m), 3.20–3.25(2H,m), 3.60–3.70(2H,m), 3.79(3H,s), 3.93(3H,s), 4.08(3H,s), 6.89(1H,s), 7.50(1H,s), 7.91(1H,s), 8.69(1H,t), 10.55(2H,brs), 11.32(1H,s).

Example 79

2-[N-(2,4,5-Trimethoxybenzoyl)amino]-4-[(2-di-n-butylaminoethyl)aminocarbonyl]-1,3-thiazole dihydrochloride MS(FAB,m/z): 493(MH$^+$); IR(KBr)cm$^{-1}$: 3400, 1655, 1615, 1578, 1561; $^1$H-NMR(CDCl$_3$)δ: 0.93–0.99(6H,m), 1.33–1.47(4H,m), 1.77–1.88(4H,m), 3.11–3.15(4H,m), 3.39–3.41(2H,m), 3.92(3H,s), 3.98(2H,brs), 3.99(3H,s), 4.21(3H,s), 6.58(1H,s), 7.71(1H,s), 8.06(1H,s), 8.93(1H,brs), 11.61(2H,brs), 11.76(1H,brs).

Example 80

2-[N-(2,4,5-Trimethoxybenzoyl)amino]-4-[(2-diisobutylaminoethyl)aminocarbonyl]-1,3-thiazole hydrochloride MS(FAB,m/z): 493(MH$^+$); IR(KBr)cm$^{-1}$: 3650, 1559, 1541, 1509; $^1$H-NMR(DMSO-d$_6$)δ: 0.99–1.05(12H,m), 2.09–2.19(2H,m), 3.01–3.05(4H,m), 3.31(2H,brs), 3.69–3.71(2H,m), 3.79(3H,s), 3.93(3H,s), 4.07(3H,s), 6.89(1H,s), 7.50(1H,s), 7.94(1H,s), 8.78(1H,s), 9.55(1H,s), 11.31(1H,s).

Example 81

2-[N-(2,4,5-Trimethoxybenzoyl)amino]-4-[(2-dicyclohexylaminoethyl)aminocarbonyl]-1,3-thiazole MS(FAB,m/z): 545(MH$^+$); IR(KBr)cm$^{-1}$: 3400, 1657, 1611, 1543, 1518; $^1$H-NMR(CDCl$_3$)δ: 1.05–1.80(20H,m), 2.57(2H,brs), 2.77–2.82(2H,m), 3.36–3.43(2H,m), 3.93(3H,s), 3.99(3H,s), 4.10(3H,s), 6.59(1H,s), 7.73(1H,s), 7.73–7.77(1H,m), 7.79(1H,s), 11.06(1H,brs).

Example 82

2-[N-(2,4,5-Trimethoxybenzoyl)amino]-4-[[2-(N-ethyl-N-methylamino)ethyl]aminocarbonyl]-1,3-thiazole MS(EI,m/z): 422(M$^+$); IR(KBr)cm$^{-1}$: 3318, 1650, 1609; $^1$H-NMR(CDCl$_3$)δ: 1.11(3H,t), 2.30(3H,s), 2.52(2H,q), 2.61(2H,t), 3.54(2H,q), 3.93(3H,s), 3.99(3H,s), 4.13(3H,s), 6.59(1H,s), 7.56(1H,brt), 7.75(1H,s), 7.78(1H,s), 11.05(1H,brs).

Example 83

2-[N-(2,4,5-Trimethoxybenzoyl)amino]-4-[[2-(N-isopropyl-N-n-propylamino)ethyl]aminocarbonyl]-1,3-thiazole dihydrochloride $^1$H-NMR(CDCl$_3$)δ: 0.96(3H,t), 1.02–1.10(6H,m), 1.43–1.60(2H,m), 1.58–1.79(4H,m), 2.38–2.53(2H,m), 2.59–2.72(2H,m), 2.97–3.09(1H,m), 3.41–3.55(2H,m), 3.93(3H,s), 3.99(3H,s), 4.10(3H,s), 6.59(1H,s), 7.74(1H,s), 7.79(1H,s), 7.74–8.02(1H,m), 11.42(1H,s).

Example 84

2-[N-(2,4,5-Trimethoxybenzoyl)amino]-4-[[2-(N-isopropyl-N-n-butylamino)ethyl]aminocarbonyl]-1,3-thiazole dihydrochloride ¹H-NMR(CDCl₃)δ: 0.91(3H,t), 1.05(6H,d), 1.33–1.47(4H,m), 1.83–2.02(2H,m), 2.45–2.51(2H,m), 2.63–2.68(2H,m), 3.01–3.06(1H,m), 3.44–3.49(2H,m), 3.93(3H,s), 3.99(3H,s), 4.16(3H,s), 6.59(1H,s), 7.74(1H,s), 7.79(1H,s), 7.72–7.79(1H,m), 9.86–9.98(2H,m), 11.07(1H,s).

Example 85
2-[N-(2,4,5-Trimethoxybenzoyl)amino]-4-[(2-diisopropylaminoethyl)aminocarbonyl]-5-chloro-1,3-thiazole dihydrochloride ¹H-NMR(DMSO-d₆)δ: 1.30–1.37(12H,m), 3.10–3.28(2H,m), 3.53–3.89(4H,m), 3.78(3H,s), 3.93(3H,s), 4.07(3H,s), 6.88(1H,s), 7.46(1H,s), 8.67–8.80(1H,m), 9.76–9.94(2H,m), 11.42(1H,s).

Example 86
2-[N-(2,4,5-Trimethoxybenzoyl)amino]-4-[(2-diisopropylaminoethyl)aminocarbonyl]-5-methyl-1,3-thiazole dihydrochloride ¹H-NMR(DMSO-d₆)δ: 1.29–1.36(12H,m), 2.68(3H,s), 3.16–3.24(2H,m), 3.52–3.61(4H,m), 3.78(3H,s), 3.92(3H,s), 4.08(3H,s), 6.88(1H,s), 7.50(1H,s), 8.54–8.63(1H,m), 9.58–9.70(2H,m), 11.16(1H,s).

Example 87
2-[N-(2,4,5-Trimethoxybenzoyl)amino]-4-[[2-(N-methoxy-N-methylamino)ethyl]aminocarbonyl]-1,3-thiazole MS(FAB,m/z): 425(MH⁺); IR(KBr)cm⁻¹: 1657, 1608, 1537, 1263, 1024; ¹H-NMR(CDCl₃)δ: 2.65(3H,s), 2.87(2H,t), 3.60(3H,s), 3.65(2H,q), 3.93(3H,s), 4.00(3H,s), 4.12(3H,s), 6.59(1H,s), 7.59(1H,t), 7.76(1H,s), 7.78(1H,s), 11.03(1H,s).

Example 88
2-[N-(2,4,5-Trimethoxybenzoyl)amino]-4-[[2-(N-2-methoxyethyl-N-isopropylamino)ethyl]aminocarbonyl]-1,3-thiazole dihydrochloride MS(FAB,m/z): 481(MH⁺); IR(KBr)cm⁻¹: 1655, 1610, 1549, 1271, 1228, 1016; ¹H-NMR(DMSO-d₆)δ: 1.28(6H,d), 3.22–3.35(4H,m), 3.29(3H,s), 3.67–3.74(5H,m), 3.78(3H,s), 3.93(3H,s), 4.08(3H,s), 6.89(1H,s), 7.50(1H,s), 7.92(1H,s), 8.72(1H,t), 9.96(2H,brs), 11.32(1H,s).

Example 89
2-[N-(2,4,5-Trimethoxybenzoyl)amino]-4-[[2-[N-(2-dimethylaminoethyl)-N-methylamino]ethyl]aminocarbonyl]-1,3-thiazole dimaleate IR(KBr)cm⁻¹: 3322, 1655; ¹H-NMR(DMSO-d₆)δ: 2.40(3H,s), 2.76(6H,s), 2.83–2.95(2H,m), 3.15–3.20(2H,m), 3.43–3.46(4H,m), 3.50(4H,brs), 3.78(3H,s), 3.93(3H,s), 4.07(3H,s), 6.12(4H,s), 6.89(1H,s), 7.50(1H,s), 7.84(1H,s), 8.29(1H,t), 11.26(1H,s).

Example 90
2-[N-(2,4,5-Trimethoxybenzoyl)amino]-4-[[2-[N-(3,4-dimethoxybenzyl)-N-isopropylamino]ethyl]aminocarbonyl]-1,3-thiazole IR(KBr)cm⁻¹: 3339, 1671, 1658, 1611; ¹H-NMR(CDCl₃)δ: 1.08(6H,d), 2.69(2H,t), 2.95–3.05(1H,m), 3.44(2H,q), 3.59(2H,s), 3.79(3H,s), 3.81(3H,s), 3.93(3H,s), 3.99(3H,s), 4.02(3H,s), 6.57(1H,s), 6.78(1H,d), 6.92(1H,dd), 6.98(1H,d), 7.74(1H,s), 7.74–7.79(1H,m), 7.79(1H,s), 11.09(1H,s).

Example 91
2-[N-(2,4,5-Trimethoxybenzoyl)amino]-4-[[2-[N-[2-(3,4-dimethoxyphenyl)ethyl]-N-isopropylamino]ethyl]aminocarbonyl]-1,3-thiazole hydrochloride IR(KBr)cm⁻¹: 3450, 1675, 1600, 1609; ¹H-NMR(DMSO-d₆)δ: 1.32(6H,t), 3.07(2H,t), 3.11–3.40(4H,m), 3.70–3.80(4H,m), 3.71(3H,s), 3.75(3H,s), 3.79(3H,s), 3.93(3H,s), 4.08(3H,s), 6.79–6.93(3H,m), 7.51(1H,s), 7.91(1H,s), 8.77(1H,t), 10.52(1H,brs), 11.34(1H,s).

Example 92
2-[N-(2-Ethoxy-4,5-dimethoxybenzoyl)amino]-4-[(2-dimethylaminoethyl)aminocarbonyl]-1,3-thiazole IR(KBr)cm⁻¹: 3314, 1661, 1611, 1545, 1514; ¹H-NMR(CDCl₃)δ: 1.69(3H,t), 2.29(6H,s), 2.53(2H,t), 3.51(2H,q), 3.93(3H,s), 3.97(3H,s), 4.34(2H,q), 6.58(1H,s), 7.70(1H,brs), 7.74(1H,s), 7.77(1H,s), 11.37(1H,s).

Example 93
2-[N-(4,5-Dimethoxy-2-isopropylbenzoyl)amino]-4-[(2-dimethylaminoethyl)aminocarbonyl]-1,3-thiazole IR(KBr)cm⁻¹: 3308, 1673, 1661, 1613; ¹H-NMR(CDCl₃)δ: 1.56(6H,d), 2.30(6H,s), 2.53(2H,t), 3.52(2H,q), 3.93(3H,s), 3.96(3H,s), 4.75–4.85(1H,m), 6.59(1H,s), 7.71(1H,brs), 7.74(1H,s), 7.75(1H,s), 11.54(1H,s).

Example 94
2-[N-(4,5-Diethoxy-2-methoxybenzoyl)amino]-4-[(2-diisopropylaminoethyl)aminocarbonyl]-1,3-thiazole fumarate IR(KBr)cm⁻¹: 3300, 2980, 2960, 2600, 2500, 1670, 1650, 1600; ¹H-NMR(DMSO-d₆)δ: 1.11(12H,d), 1.31(3H,t), 1.38(3H,t), 2.75–2.85(2H,m), 3.18–3.35(2H,m), 3.35–3.45(2H,m), 3.80(2H,brs), 4.02(2H,q), 4.04(3H,s), 4.20(2H,q), 6.59(2H,s), 6.85(1H,s), 7.49(1H,s), 7.83(1H,s), 8.37(1H,brs), 11.29(1H,s).

Example 95
2-[N-(2-Benzyloxy-4,5-dimethoxybenzoyl)amino]-4-[(2-dimethylaminoethyl)aminocarbonyl]-1,3-thiazole IR(KBr)cm⁻¹: 3318, 1671, 1647, 1607; ¹H-NMR(CDCl₃)δ: 2.32(6H,s), 2.54(2H,t), 3.55(2H,q), 3.93(3H,s), 3.94(3H,s), 5.33(2H,s), 6.65(1H,s), 7.25(1H,brs), 7.42–7.57(5H,m), 7.72(1H,s), 7.78(1H,s), 11.19(1H,s).

Example 96
2-[N-(2-Hydroxy-4,5-dimethoxybenzoyl)amino]-4-[(2-isopropylaminoethyl)aminocarbonyl]-1,3-thiazole dihydrochloride MS(FAB,m/z): 409(MH⁺); IR(KBr)cm⁻¹: 2976, 1647, 1560, 1269, 1213; ¹H-NMR(DMSO-d₆)δ: 1.23(6H,d), 3.07(2H,brs), 3.33(1H,dt), 3.55–3.62(2H,m), 3.77(3H,s), 3.81(3H,s), 6.89(1H,s), 7.50(1H,s), 7.90(1H,s), 8.64–8.70(3H,m), 11.80(1H,s), 12.02(2H,brs).

Example 97
2-[N-(2-Hydroxy-4,5-dimethoxybenzoyl)amino]-4-[[2-(N-methyl-N-isopropylamino)ethyl]aminocarbonyl]-1,3-thiazole dihydrochloride MS(FAB, m/z): 423(MH⁺); IR(KBr)cm⁻¹: 3010, 1662, 1551, 1292, 1213; ¹H-NMR(DMSO-d₆)δ: 1.24(6H,dd), 2.72(3H,d), 3.07–3.14(1H,m), 3.26–3.33(1H,m), 3.58–3.65(3H,m), 3.77(3H,s), 3.81(3H,s), 6.88(1H,s), 7.50(1H,s), 7.90(1H,s), 8.71(1H,t), 9.80(1H,brs), 11.79(1H,s), 12.02(2H,brs).

Example 98
2-[N-(2-Hydroxy-3,4-dimethoxybenzoyl)amino]-4-[[2-(N-ethyl-N-isopropylamino)ethyl]aminocarbonyl]-1,3-thiazole dihydrochloride MS(FAB,m/z): 437(MH⁺); IR(KBr)cm⁻¹: 3010, 1660, 1551, 1520, 1292, 1161; ¹H-NMR(DMSO-d₆)δ: 1.24–1.31(9H,m), 3.10–3.35(4H,m), 3.59–3.67(3H,m), 3.77(3H,s), 3.82(3H,s), 6.84(1H,s), 7.50(1H,s), 7.90(1H,s), 8.72(1H,t), 9.56(1H,brs), 11.78(1H,s), 12.00(2H,brs).

Example 99
2-[N-(2-Hydroxy-4,5-dimethoxybenzoyl)amino]-4-[[2-(N-isopropyl-N-n-propylamino)ethyl]aminocarbonyl]-1,3-thiazole dihydrochloride MS(FAB,m/z): 451 (MH$^+$); IR(KBr)cm$^{-1}$: 2980, 1672, 1641, 1600, 1265, 1213; $^1$H-NMR(DMSO-d$_6$)δ: 0.93(3H,t), 1.27(6H,d), 1.75(2H,dt), 2.98–3.16(3H,m), 3.23–3.30(1H, m), 3.62–3.66(3H,m), 3.77(3H,s), 3.81(3H,s), 6.91(1H,s), 7.49(1H,s), 7.90(1H,s), 8.76(1H,t), 9,85(1H,brs), 11.79(1H, s), 12.02(2H,brs).

Example 100
2-[N-(4-Hydroxy-2,5-dimethoxybenzoyl)amino]-4-[(2-dimethylaminoethyl)aminocarbonyl]-1,3-thiazole maleate IR(KBr)cm$^{-1}$: 3386, 3291, 1647, 1607, 1527; $^1$H-NMR(DMSO-d$_6$)δ: 2.83(6H,s), 3.24–3.33(4H,m), 3.50–3.61(2H, m), 3.80(3H,s), 3.97(3H,s), 6.01(2H,s), 6.74(1H,s), 7.53(1H,s), 7.87(1H,s), 8.50–8.70(1H,m), 10.30(1H,s), 11.16(1H,s).

Example 101
2-[N-(4-Hydroxy-2,5-dimethoxybenzoyl)amino]-4-[(2-isopropylaminoethyl)aminocarbonyl]-1,3-thiazole hydrochloride IR(KBr)cm$^{-1}$: 3308, 1674; $^1$H-NMR(DMSO-d$_6$)δ: 1.24(6H,d), 3.00–3.13(2H,m), 3.26–3.38(1H,m), 3.56–3.66(2H, m), 3.80(3H,s), 3.90–4.10(1H,m), 3.98(3H,s), 6.78(1H,s), 7.52(1H,s), 7.89(1H,s), 8.59(1H,t), 8.70–8.95(2H,br), 11.22(1H,s).

Example 102
2-[N-(4-Hydroxy-2,5-dimethoxybenzoyl)amino]-4-[[2-(N-methyl-N-isopropylamino)ethyl]aminocarbonyl]-1,3-thiazole hydrochloride IR(KBr)cm$^{-1}$: 3200, 1684; $^1$H-NMR(DMSO-d$_6$)δ: 1.25(6H,dd), 2.71(3H,d), 3.01–3.16(1H,m), 3.22–3.36(1H,m), 3.51–3.78(3H,m), 3.80(3H,s), 3.98(3H,s), 3.80–4.00(1H,m), 6.78(1H,s), 7.52(1H,s), 7.89(1H,s), 8.66(1H,t), 10.20–10.30(1H,br), 11.22(1H, s).

Example 103
2-[N-(4-Hydroxy-2,5-dimethoxybenzoyl)amino]-4-[[2-(N-ethyl-N-isopropylamino)ethyl]aminocarbonyl]-1,3-thiazole hydrochloride IR(KBr)cm$^{-1}$: 3200, 1675; $^1$H-NMR(DMSO-d$_6$)δ: 1.22–1.31(9H,m), 3.10–3.30(4H,m), 3.60–3.75(3H,m), 3.80(3H,s), 3.98(3H,s), 6.74(1H,s), 7.52(1H,s), 7.89(1H,s), 8.60–8.70(1H,m), 9.30–9.40(1H,br), 10.30(1H,s), 11.18(1H,s).

Example 104
2-[N-(4-Hydroxy-2,5-dimethoxybenzoyl)amino]-4-[(2-diisopropylaminoethyl)aminocarbonyl]-1,3-thiazole maleate IR(KBr)cm$^{-1}$: 3570, 3200, 1655, 1603, 1561; $^1$H-NMR(DMSO-d$_6$)δ: 1.29(12H,d), 3.10–3.75(8H,m), 3.80(3H,s), 3.97(3H,s), 6.03(2H,s), 6.74(1H,s), 7.52(1H,s), 7.89(1H,s), 8.56(1H,brs), 10.32(1H,s), 11.17(1H,s).

Example 105
2-[N-(4-Hydroxy-2,5-dimethoxybenzoyl)amino]-4-[[2-(N-isopropyl-N-n-propylamino)ethyl]aminocarbonyl]-1,3-thiazole dihydrochloride IR(KBr)cm$^{-1}$: 3400, 3200, 1686, 1665, 1617, 1553; $^1$H-NMR(DMSO-d$_6$)δ: 0.93(3H,t), 1.27(3H,d), 1.28(3H,d), 1.73–1.82(2H,m), 3.00–3.17(4H,m), 3.20–3.35(1H,m), 3.57–3.78(2H,m), 3.80(3H,s), 3.98(3H,s), 6.00–6.30(2H, br), 6.79(1H,s), 7.52(1H,s), 7.89(1H,s), 8.70(1H,t), 10.20(1H,brs), 11.22(1H,s).

Example 106
2-[N-(5-Hydroxy-2,4-dimethoxybenzoyl)amino]-4-[(2-diisopropylaminoethyl)aminocarbonyl]-1,3-thiazole maleate IR(KBr)cm$^{-1}$: 3650, 3200, 1663, 1541; $^1$H-NMR(DMSO-d$_6$)δ: 1.30(12H,d), 3.19(2H,brs), 3.33(2H,brs), 3.56(2H,brs), 3.68(2H,brs), 3.92(3H,s), 4.04(3H,s), 6.02(2H,s), 6.84(1H,s), 7.42(1H,s), 7.88(1H,s), 8.55(1H,brs), 9.15(1H, s), 11.22(1H,s).

Example 107
2-[N-(4,5-Dihydroxy-2-methoxybenzoyl)amino]-4-[(2-diisopropylaminoethyl)aminocarbonyl]-1,3-thiazole hydrochloride IR(KBr)cm$^{-1}$: 3400, 1655, 1607; $^1$H-NMR(DMSO-d$_6$)δ: 1.31(6H,d), 1.34(6H,d), 3.15–3.18(2H,m), 3.60–3.75(4H, m), 3.96(3H,s), 6.69(1H,s), 7.44(1H,s), 7.85(1H,d), 8.66(1H,t), 9.20(1H,s), 9.70(1H,brs), 10.10(1H,s), 11.18(1H,s).

Example 108
2-[N-(2,4-Dihydroxy-5-methoxybenzoyl)amino]-4-[(2-diisopropylaminoethyl)aminocarbonyl]-1,3-thiazole dihydrochloride $^1$H-NMR(CDCl$_3$)δ: 1.46(12H,d), 1.84–1.89(2H,m), 3.21–3.27(2H,m), 3.65–3.78(2H,m), 3.92–3.98(2H,m), 3.94(3H,s), 6.58(1H,s), 7.54(1H,s), 7.80(1H,s), 8.97–9.05(1H, m), 10.79–10.92(2H,m), 11.45(1H,s).

Example 109
2-[N-(2-Acetyloxy-4,5-dimethoxybenzoyl)amino]-4-[(2-diisopropylaminoethyl)aminocarbonyl]-1,3-thiazole hydrochloride In 10.5 ml of acetic anhydride, 3.7 g of 2-[N-(4,5-dimethoxy-2-hydroxybenzoyl)amino]-4-[(2-diisopropylaminoethyl)aminocarbonyl]-1,3-thiazole hydrochloride obtained in Example 38 was suspended, followed by stirring at 90° C. for 3 hours. After the reaction mixture was allowed to cool down, 100 ml of toluene was added thereto. The crystals so precipitated were collected by filtration, followed by drying, whereby 3.33 g of the title compound was obtained. Yield: 91%.

$^1$H-NMR(DMSO-d$_6$)δ: 1.31(6H,d), 1.35(6H,d), 3.19(2H, brs), 3.59–3.69(4H,m), 3.83(3H,s), 3.87(3H,s), 6.91(1H,s), 7.42(1H,s), 7.91(1H,s), 8,44(1H,t), 10.07(1H,brs), 12.49(1H,s).

Example 110
2-[N-(2-Chloro-4,5-dimethoxybenzoyl)amino]-4-[(2-dimethylaminoethyl)aminocarbonyl]-1,3-thiazole dihydrochloride $^1$H-NMR(CDCl$_3$)δ: 2.27(6H,s), 2.52–2.57(2H,m), 3.51–3.55(2H,m), 3.94(3H,s), 3.96(3H,s), 6.93(1H,s), 7.53(1H,s), 7.55(1H,s), 7.79(1H,s), 10.50(3H,brs).

Example 111
2-[N-(2-Chloro-4,5-dimethoxybenzoyl)amino]-4-[(2-diisopropylaminoethyl)aminocarbonyl]-1,3-thiazole dihydrochloride $^1$H-NMR(CDCl$_3$)δ: 1.44–1.53(12H,m), 3.39–3.50(2H, m), 3.48–3.82(4H,m), 3.71–3.93(2H,m), 3.95(3H,s), 4.02(3H,s), 6.90–7.02(1H,m), 6.96(1H,s), 7.57(1H,s), 8.38(1H, s), 9.60–9.75(1H,m), 10.10–10.37(1H,m), 13.46–13.68(1H, m).

Example 112
2-[N-(2-Bromo-4,5-dimethoxybenzoyl)amino]-4-[(2-diisoopropylaminoethyl)aminocarbonyl]-1,3-thiazole dihydrochloride IR(KBr)cm$^{-1}$: 3250, 1690, 1597, 1559; $^1$H-NMR (DMSO-d$_6$)δ: 1.31(6H,d), 1.35(6H,d), 3.17(2H,brs), 3.50–3.70(4H,m), 3.81(3H,s), 3.85(3H,s), 7.24(1H,s), 7.26(1H,s), 7.95(1H,s), 8.44(1H,t), 10.19(2H,brs), 12.72(1H, brs).

Example 113
2-[N-(4,5-Dimethoxy-2-nitrobenzoyl)amino]-4-[(2-diisopropylaminoethyl)aminocarbonyl]-1,3-thiazole
MS(FAB,m/z): 480(MH$^+$);
IR(KBr)cm$^{-1}$: 1549, 1523, 1294, 1059; $^1$H-NMR(CDCl$_3$) δ: 0.98(12H,d), 2.62(2H,t), 2.99(2H,dt), 3.29(2H,q), 3.97(3H,s), 4.02(3H,s), 6.99(1H,s), 7.36(1H,brs), 7.63(1H,s), 7.74(1H,s).

Example 114
2-[N-(2-Amino-4,5-dimethoxybenzoyl)amino]-4-[(2-diisopropylaminoethyl)aminocarbonyl]-1,3-thiazole dihydrochloride
$^1$H-NMR(DMSO-d$_6$)δ: 1.30–1.37(12H,m), 3.18(2H,brs), 3.60–3.69(4H,m), 3.80(3H,s), 3.81(3H,s), 4.25–5.75(4H,m), 6.82(1H,s), 7.52(1H,s), 7.93(1H,s), 8.50(1H,t), 10.15(1H,s).

Example 115
2-[N-(4,5-Dimethoxy-2-fluorobenzoyl)amino]-4-[(2-diisopropylaminoethyl)aminocarbonyl]-1,3-thiazole maleate
MS(FAB,m/z): 453(MH$^+$); IR(KBr)cm$^{-1}$: 1662, 1545, 1354, 1273; $^1$H-NMR(DMSO-d$_6$)δ: 1.29(12H,d), 3.19(2H, brs), 3.55(2H,brs), 3.67(2H,brs), 3.82(3H,s), 3.86(3H,s), 6.02(2H,s), 7.07(1H,d), 7.31(1H,d), 7.92(1H,s), 8.39(1H, brs), 8.56(2H,brs), 12.11(1H,s).

Example 116
2-[N-(4-Amino-2,5-dimethoxybenzoyl)amino]-4-[(2-diisopropylaminoethyl)aminocarbonyl]-1,3-thiazole fumarate
$^1$H-NMR(DMSO-d$_6$)δ: 1.07–1.12(12H,m), 2.72–2.76(2H,m), 3.17–3.22(2H,m), 3.31–3.42(2H,m), 3.80(3H,s), 3.95(2H,s), 4.01(3H,s), 5.95(1H,s), 6.59(2H,s), 6.78(1H,s), 7.39(1H,d), 7.77(1H,d), 8.31–8.33(1H,m), 8.81(1H,s), 11.14(1H,s).

Example 117
2-[N-(2,5-Dimethoxy-4-formylaminobenzoyl)amino]-4-[(2-diisopropylaminoethyl)aminocarbonyl]-1,3-thiazole
$^1$H-NMR(CDCl$_3$)δ: 1.08(12H,d), 1.61(1H,s), 2.67–2.72(2H,m), 3.05–3.12(2H,m), 3.40–3.43(2H,m), 3.95(3H,s), 4.10(3H,s), 7.75(1H,s), 7.82(1H,s), 8.08(1H,s), 8.38(1H,s), 8.55(1H,s), 11.18(1H,s).

Example 118
2-[N-(4-Acetylamino-2,5-dimethoxybenzoyl)amino]-4-[(2-diisopropylaminoethyl)aminocarbonyl]-1,3-thiazole hydrochloride
$^1$H-NMR(DMSO-d$_6$)δ: 1.33–1.37(12H,m), 2.18(3H,s), 3.15–3.17(2H,m), 3.56–3.70(4H,m), 3.89(3H,s), 3.98(3H,s), 4.90–5.20(2H,m), 7.55(1H,s), 7.91(1H,s), 8.22(1H,s), 8.65–8.73(1H,m), 9.50(1H,s), 10.03(1H,s), 11.42(1H,s).

Example 119
2-[N-(2,5-Dimethoxy-4-nitrobenzoyl)amino]-4-[(2-diisopropylaminoethyl)aminocarbonyl]-1,3-thiazole hydrochloride
$^1$H-NMR(CDCl$_3$)δ: 1.42–1.54(12H,m), 1.57(2H,s), 3.20–3.22(2H,m), 3.61–3.64(2H,m), 3.92–4.01(2H,m), 4.01(3H,s), 4.23(3H,s), 7.55(1H,s), 7.86(1H,s), 8.06(1H,s), 9.10–9.20(1H,m), 11.20–11.30(1H,m), 11.46(1H,s).

Example 120
2-[N-(4-Bromo-2,5-dimethoxybenzoyl)amino]-4-[(2-diisopropylaminoethyl)aminocarbonyl]-1,3-thiazole hydrochloride
$^1$H-NMR(CDCl$_3$)δ: 1.43(6H,d), 1.53(6H,d), 3.15–3.30(2H,m), 3.50–3.65(2H,m), 3.90–4.05(2H,m), 3.94(3H,s), 4.17(3H,s), 7.29(1H,s), 7.81(1H,s), 7.82(1H,s), 9.07(1H, brs), 11.25(1H,brs), 11.40(1H,s).

Example 121
2-[N-(4-Bromo-2-hydroxy-5-methoxybenzoyl)amino]-4-[(2-diisopropylaminoethyl)aminocarbonyl]-1,3-thiazole hydrochloride
$^1$H-NMR(CDCl$_3$+5%—CD$_3$OD)δ: 1.40–1.50(12H,m), 3.28(2H,t), 3.37–3.75(2H,m), 3.88(2H,t), 3.95(3H,s), 7.37(1H,s), 7.66(1H,s), 7.84(1H,s).

Example 122
2-[N-(4,5-Dichloro-2-methoxybenzoyl)amino]-4-[(2-diisopropylaminoethyl)aminocarbonyl]-1,3-thiazole hydrochloride
$^1$H-NMR(CDCl$_3$)δ: 1.43(6H,d), 1.52(6H,d), 3.20(2H, brs), 3.57–3.64(2H,m), 3.90–4.00(2H,m), 4.21(3H,s), 7.17(1H,s), 7.82(1H,s), 8.35(1H,s), 9.10(1H,brs), 11.21(1H,s).

Example 123
2-[N-(4,5-Dichloro-2-hydroxybenzoyl)amino]-4-[(2-diisopropylaminoethyl)aminocarbonyl]-1,3-thiazole hydrochloride
$^1$H-NMR(CDCl$_3$)δ: 1.45(6H,d), 1.53(6H,d), 3.32(2H, brs), 3.66(2H,brs), 3.96(2H,brs), 7.30(1H,s), 7.82(1H,s), 8.22(1H,s), 8.97(1H,brs), 10.49(1H,brs).

Example 124
2-[N-(4-Amino-5-chloro-2-methoxybenzoyl)amino]-4-[(2-dimethylaminoethyl)aminocarbonyl]-1,3-thiazole maleate
IR(KBr)cm$^{-1}$: 3400, 3350, 3220, 1655, 1601; $^1$H-NMR (CDCl$_3$, measured was a compound in the form of a free base)δ: 2.30(6H,s), 2.53(2H,t), 3.53(2H,q), 4.07(3H,s), 4.59(2H,brs), 6.35(1H,s), 7.73(1H,s), 7.45(1H,brs), 8.19(1H,s), 10.79(1H,s).

Example 125
2-[N-(4-Amino-5-chloro-2-methoxybenzoyl)amino]-4-[(2-diisopropylaminoethyl)aminocarbonyl]-1,3-thiazole dihydrochloride
$^1$H-NMR(DMSO-d$_6$)δ: 1.32–1.37(12H,m), 3.10–3.25(2H,m), 3.60–3.75(4H,m), 3.98(3H,s), 4.77(3H,brs), 6.61(1H,s), 7.80(1H,s), 7.84(1H,s), 8.70(1H,t), 10.20(1H,s), 11.03(1H,s).

Example 126
2-[N-(4-Acetylamino-5-chloro-2-methoxybenzoyl)amino]-4-[(2-diisopropylaminoethyl)aminocarbonyl]-1,3-thiazole hydrochloride
$^1$H-NMR(DMSO-d$_6$)δ: 1.32(6H,d), 1.35(6H,d), 2.19(3H, s), 3.17(2H,brs), 3.29(2H,brs), 3.50–3.75(2H,m), 3.96(3H, s), 7.84(1H,s), 7.91(1H,s), 7.92(1H,s), 8.61(1H,brs), 9.65(1H,s), 10.01(1H,brs), 11.62(1H,s).

Example 127
2-[N-(2,4,5-Trimethoxybenzoyl)amino]-4-[(2-[(2-thiazolidinidene)imino]ethyl]aminocarbonyl]-1,3-thiazole
MS(FAB,m/z): 466(MH$^+$); IR(KBr)cm$^{-1}$: 3432, 3289, 1669, 1609, 1545, 1516; $^1$H-NMR(CDCl$_3$)δ: 3.34–3.39(2H, m), 3.57–3.61(2H,m), 3.64–3.76(2H,m), 3.89(3H,s), 3.92–4.07(5H,m), 4.15(3H,s), 6.60(1H,s), 7.76–7,81(3H,m).

Example 128
2-[N-(2,4,5-Trimethoxybenzoyl)amino]-4-[[2-(1-imidazolyl)ethyl]aminocarbonyl]-1,3-thiazole MS(FAB,m/z): 432(MH⁺) IR(KBr)cm⁻¹: 3537, 3424, 3308, 1653, 1611, 1541, 1518; ¹H-NMR(CDCl₃)δ: 3.73–3.79(2H,m), 3.92(3H,s), 3.99(3H,s), 4.13(3H,s), 4.21–4.25(2H,m), 6.59(1H,s), 6.98–6.99(1H,m), 7.31(1H, brs), 7.53(1H,s), 7.77–7.79(2H,m), 11.01 (1H,s).

Example 129
2-[N-(4-Amino-2-hydroxy-5-methoxybenzoyl)amino]-4-[(2-diisopropylaminoethyl)aminocarbonyl]-1,3-thiazole ¹H-NMR(DMSO-d₆)δ: 0.91–1.30(2H,m), 2.48–2.51(2H, m), 2.55–2.82(2H,M), 2.98–3.38(4H,m), 3.76(3H,s), 5.74 (1H,s), 6.57(1H,s), 7.33(1H,s), 7.66–7.69(1H,m), 8.03–8.50 (1H,m), 8.58–8.61(1H,m).

Example 130
2-[N-(4-Formylamino-2-hydroxy-5-methoxybenzoyl) amino]-4-[(2-diisopropylaminoethyl)aminocarbonyl]-1,3-thiazole dihydrochloride ¹H-NMR(DMSO-d₆)δ: 1.25–1.36(12H,m), 3.09–3.22 (2H,m), 3.41–3.56(2H,m), 3.56(1H,s), 3.51–3.77(2H,m), 3.88(3H,s), 7.57(1H,s), 7.89(1H,s), 8.22(1H,s), 8.38(1H,s), 8.60–8.72(1H,m), 9.37–9.51(1H,m), 10.02(1H,s).

Example 131
2-[N-(2-Methoxy-4-methyl-5-nitrobenzoyl)amino]-4-[(2-diisopropylaminoethyl)aminocarbonyl]-1,3-thiazole dihydrochloride ¹H-NMR(DMSO-d₆)δ: 1.30–1.36(12H,m), 2.67(2H,s), 3.17(2H,s), 3.57(3H,s), 3.55–3.71(2H,m), 4.05(3H,s), 7.37 (1H,s), 7.94(1H,s), 8.42(1H,s), 8.50–8.61(1H,m), 9.76–9.89 (1H,m), 12.03(1H,s).

Example 132
2-[N-(2,4-Dimethoxy-5-nitrobenzoyl)amino]-4-[(2-diisopropylaminoethyl)aminocarbonyl]-1,3-thiazole hydrochloride ¹H-NMR(DMSO-d₆)δ: 1.30–1.36(12H,m), 3.14–3.22 (2H,m), 3.40–3.71(4H,m), 4.09(3H,s), 4.13(3H,s), 7.00(1H, s), 7.92(1H,s), 8.42(1H,s), 8.55–8.64(1H,m), 9.79–9.88(1H, m), 11.76(1H,s).

Example 133
2-[N-(5-Amino-2,4-dimethoxybenzoyl)amino]-4-[(2-diisopropylaminoethyl)aminocarbonyl]-1,3-thiazole dihydrochloride ¹H-NMR(DMSO-d₆)δ: 1.30–1.36(12H,m), 3.16(2H,s), 3.29–3.42(4H,m), 3.52–3.73(2H,m), 4.05(3H,s), 4.11(3H,s), 7.01(1H,s), 7.91(1H,s), 7.97(1H,s), 8.62–8.71(1H,m), 9.77–9.89(2H,m), 11.43(1H,s).

Example 134
2-[N-(5-Formylamino-2,4-dimethoxybenzoyl)amino]-4-[(2-diisopropylaminoethyl)aminocarbonyl]-1,3-thiazole hydrochloride ¹H-NMR(DMSO-d₆)δ: 1.30–1.36(12H,m), 3.10–3.23 (2H,m), 3.54–3.75(4H,m), 4.01(3H,s), 4.08(3H,s), 6.92(1H, s), 7.89(1H,s), 8.28(1H,s), 8.64–8.68(1H,m), 8.72(1H,s), 9.70(1H,s), 9.69–9.80(1H,m), 11.35(1H,s).

Example 135
2-[N-(5-Acetylamino-2,4-dimethoxybenzoyl)amino]-4-[(2-diisopropylaminoethyl)aminocarbonyl]-1,3-thiazole ¹H-NMR(CDCl₃)δ: 1.02–1.14(12H,m), 2.19(3H,s), 2.62–2.78(2H,m), 3.01–3.18(2H,m), 3.37–3.49(2H,m), 3.98 (3H,s), 4.09(3H,s), 6.54(1H,s), 7.40(1H,s), 7.61–7.72(2H, m), 9.04(1H,s), 10.89(1H,s).

Example 136
2-[N-(4-Methoxy-3-nitrobenzoyl)amino]-4-[(2-diisopropylaminoethyl)aminocarbonyl]-1,3-thiazole hydrochloride ¹H-NMR(CDCl₃)δ: 1.30–1.36(12H,m), 3.19(2H,brs), 3.54(1H,d), 3.60–3.70(4H,m), 4.04(3H,s), 4.30(1H,brs), 7.92(1H,s), 8.33–8.37(1H,m), 8.47(1H,brs), 8.67–8.71(1H, m), 9.91(1H,brs).

Example 137
2-[N-(3-Amino-4-methoxybenzoyl)amino]-4-[(2-diisopropylaminoethyl)aminocarbonyl]-1,3-thiazole dihydrochloride ¹H-NMR(DMSO-d₆)δ: 1.30–1.36(12H,m), 3.19(2H,brs), 3.60–3.75(4H,m), 3.94(3H,s), 4.70(3H,brs), 7.17(1H,d), 7.76(1H,s), 7.86(1H,d), 7.91(1H,s), 8.41(1H,t), 9.94(1H, brs), 12.60(1H,s).

Example 138
2-[N-(3-Formylamino-4-methoxybenzoyl)amino]-4-[(2-diisopropylaminoethyl)aminocarbonyl]-1,3-thiazole ¹H-NMR(DMSO-d₆)δ: 0.98–1.05(12H,m), 2.49–2.51 (2H,m), 2.99(2H,brs), 3.20–3.40(2H,m), 3.95(3H,s), 7.21 (1H,d), 7.75(1H,s), 7.78(1H,s), 7.91(1H,dd), 8.35(1H,d), 8.85(1H,d), 9.81(1H,s), 12.52(1H,brs).

Example 139
2-[N-(3-Acetylamino-4-methoxybenzoyl)amino]-4-[(2-diisopropylaminoethyl)aminocarbonyl]-1,3-thiazole hydrochloride ¹H-NMR(DMSO-d₆)δ: 1.30–1.36(12H,m), 2.12(3H,s), 3.17(2H,brs), 3.60–3.75(4H,m), 3.93(3H,s), 7.21(1H,d), 7.89–7.93(1H,m), 7.90(1H,s), 8.41(1H,t), 8.66(1H,s), 9.31 (1H,s), 9.74(1H,brs), 12.60(1H,s).

Example 140
2-[N-(3-Methoxy-4-nitrobenzoyl)amino]-4-[(2-diisopropylaminoethyl)aminocarbonyl]-1,3-thiazole hydrochloride ¹H-NMR(DMSO-d₆)δ: 1.32(12H,brs), 3.19(2H,brs), 3.64 (4H,brs), 4.04(3H,s), 7.72(1H,d), 7.98–8.05(2H,m), 8.40 (1H,s), 9.70(1H,brs), 13.15(2H,brs).

Example 141
2-[N-(4-Amino-3-methoxybenzoyl)amino]-4-[(2-diisopropylaminoethyl)aminocarbonyl]-1,3-thiazole dihydrochloride ¹H-NMR(DMSO-d₆)δ: 1.30–1.37(12H,m), 3.17(2H,brs), 3.60–3.90(4H,m), 3.90(3H,s), 5.63(3H,brs), 6.91(1H,d), 7.61(1H,d), 7.67(1H,s), 7.89(1H,s), 8.44(1H,brs), 10.15(1H, brs), 12.40(1H,brs).

Example 142
2-[N-(4-Formylamino-3-methoxybenzoyl)amino]-4-[(2-diisopropylaminoethyl)aminocarbonyl]-1,3-thiazole fumarate ¹H-NMR(DMSO-d₆)δ: 1.01–1.08(12H,m), 2.61(2H,t), 3.00–3.20(2H,m), 3.29(2H,q), 3.40(2H,brs), 3.97(3H,s), 6.58(1H,s), 7.74(1H,d), 7.80(1H,d), 7.82(1H,t), 7.95(1H,t), 8.37(1H,d), 8.38(1H,s), 9.98(1H,s).

Example 143
2-[N-(4-Acetylamino-3-methoxybenzoyl)amino]-4-[(2-diisopropylaminoethyl)aminocarbonyl]-1,3-thiazole hydrochloride ¹H-NMR(DMSO-d₆)δ: 1.30–1.37(12H,m), 2,15(3H,s), 3.19(2H,brs), 3.47(1H,brs), 3.55–3.70(4H,m), 3.96(3H,s), 7.58(1H,d), 7.69(1H,d), 7.86(1H,s), 8.24(1H,d), 8.43(1H,t), 9.37(1H,s), 9.96(1H,brs).

Example 144
2-[N-(4-Amino-2-methoxybenzoyl)amino]-4-[(2-diisopropylaminoethyl)aminocarbonyl]-1,3-thiazole ¹H-NMR(CDCl₃)δ: 1.07(12H,d), 2.67–2.71(2H,m), 3.03–3.13(2H,m), 3.37–3.44(2H,m), 4.04(3H,s), 4,21(2H,s), 6.24–6.26(1H,m), 6.38–6.42(1H,m), 7.67–7.76(1H,m), 7.69(1H,s), 8.07–8.11(1H,m), 10.90(1H,s).

Example 145
2-[N-(4-Formylamino-2-methoxybenzoyl)amino]-4-[(2-diisopropylaminoethyl)aminocarbonyl]-1,3-thiazole ¹H-NMR(CDCl₃)δ: 1.08(12H,d), 2.68–2.73(2H,m), 3.03–3.14(2H,m), 3.36–3.45(2H,m), 4.13(3H,s), 6.86–6.90(1H,m), 7.69–7.74(3H,m), 8.01(1H,s), 8.24–8.29(1H,m), 8.48(1H,s), 11.02(1H,s).

Example 146
2-[N-(4-Acetylamino-2-methoxybenzoyl)amino]-4-[(2-diisopropylaminoethyl)aminocarbonyl]-1,3-thiazole dihydrochloride ¹H-NMR(DMSO-d₆)δ: 1.24–1.46(12H,m), 2.11(3H,s), 3.17(2H,s), 3.57–4.03(6H,m), 3.99(3H,s), 7.29–7.33(1H,m), 7.68(1H,s), 7.87–7.90(2H,m), 8.60–8.65(1H,m), 9.67(2H,s), 10.45(1H,s), 11.36(1H,s).

Example 147
2-[N-(3,4-Dimethoxybenzoyl)amino]-4-[1-(4-dimethylamino)piperidinyl]carbonyl-1,3-thiazole MS(FAB,m/z): 419(MH⁺); IR(KBr)cm⁻¹: 1655, 1601, 1549, 1516, 1269; ¹H-NMR(CDCl₃)δ: 1.41–1.56(2H,m), 1.75–1.95(2H,m), 2.30(6H,s), 2.38–2.47(1H,m), 2.60–3.15(2H,m), 3.96(3H,s), 3.97(3H,s), 4.25–4.70(2H,m), 6.96(1H,d), 7.43(1H,s), 7.48–7.56(2H,m), 9.60(1H,brs).

Example 148
2-[N-(3,4-Dimethoxybenzoyl)amino]-4-[1-(4-methylpiperazinyl)]carbonyl-1,3-thiazole IR(KBr)cm⁻¹: 3084, 1655, 1601, 1547; ¹H-NMR(CDCl₃)δ: 2.30(3H,s), 2.40(4H,brs), 3.74(4H,brs), 3.95(3H,s), 3.96(3H,s), 6.94(1H,d), 7.47(1H,s), 7.51(1H,dd), 7.56(1H,d), 10.00(1H,brs).

Example 149
2-[N-(2,4,5-Trimethoxybenzoyl)amino]-4-[[(2-dimethylamino-1-methyl)ethyl]aminocarbonyl]-1,3-thiazole maleate MS(EI,m/z): 422(M⁺); IR(KBr)cm⁻¹: 3289, 1711, 1665, 1610; ¹H-NMR(DMSO-d₆)δ: 1.22(3H,d), 2.81(6H,s), 3.08–3.40(2H,m), 3.79(3H,s), 3.93(3H,s), 4.08(3H,s), 4.44–4.48(1H,m), 6.01(2H,s), 6.88(1H,s), 7.51(1H,s), 7.89(1H,s), 8.33(1H,d), 8.70–9.50(1H,br), 11.24(1H,s).

Example 150
2-[N-(2,4,5-Trimethoxybenzoyl)amino]-4-[(4-dimethylaminophenyl)aminocarbonyl]-1,3-thiazole MS(FAB,m/z): 456(MH⁺); IR(KBr)cm⁻¹: 3335, 1659, 1640, 1609, 1516; ¹H-NMR(CDCl₃)δ: 2.95(6H,s), 3.93(3H,s), 4.00(3H,s), 4.17(3H,s), 6.61(1H,s), 6.76(2H,d), 7.58(2H,d), 7.83(1H,s), 7.84(1H,s), 8.87(1H,brs), 11.06(1H,brs).

Example 151
2-[N-(2,4,5-Trimethoxybenzoyl)amino]-4-[[4-(1-methylpiperidinyl)]aminocarbonyl]-1,3-thiazole MS(FAB,m/z): 435(MH⁺); IR(KBr)cm⁻¹: 3519, 3357, 1655, 1611, 1538; ¹H-NMR(CDCl₃)δ: 1.61–1.75(2H,m), 2.03–2.24(5H,m), 2.34(3H,s), 2.87–2.92(2H,m), 3.93(3H,s), 3.99(3H,s), 4.15(3H,s), 6.60(1H,s), 7.08(1H,brd), 7.76(1H,s), 7.78(1H,s), 11.03(1H,brs).

Example 152
2-[N-(2,4,5-Trimethoxybenzoyl)amino]-4-[[[2-(1-methylpiperidinyl)]methyl]aminocarbonyl]-1,3-thiazoledihydrochloride MS(FAB,m/z) : 449(MH⁺); IR(KBr)cm⁻¹: 3185, 1665, 1607, 1551; ¹H-NMR(DMSO-d₆)δ: 1.79–1.98(6H,m), 2.80–2.83(3H,m), 3.05–3.55(4H,m), 3.79(3H,s), 3.93(3H,s), 4.10(3H,d), 4.42(1H,brs), 6.88(1H,s), 7.50(1H,d), 7.89(1H,d), 8.39(0.5H,d), 8.69(0.5H,d), 10.98(0.5H,brs), 11.30(0.5H,brs), 11.38(2H,brs).

Example 153
2-[N-(4,5-Dimethoxy-2-hydroxybenzoyl)amino]-4-[(2-diisopropylaminoethyl)oxycarbonyl]-1,3-thiazole hydrochloride IR(KBr)cm⁻¹: 3185, 1665, 1607, 1551; ¹H-NMR(DMSO-d₆)δ: 1.23–1.42(12H,m), 3.28–3.48(2H,m), 3.65–3.71(2H,m), 3.78(3H,s), 3.82(3H,s), 4.52–4.63(2H,m), 6.70(1H,s), 7.60(1H,s), 8.18(1H,s), 9.84(1H,s), 11.91–11.98(1H,m), 12.28(1H,s).

Example 154
2-[N-(2-Methoxy-3,4-methylidenedioxybenzoyl)amino]-4-[(2-diisopropylaminoethyl)aminocarbonyl]-1,3-thiazole maleate IR(KBr)cm⁻¹: 3250, 1653, 1541; ¹H-NMR(DMSO-d₆)δ: 1.30(12H,d), 3.10–3.25(2H,m), 3.50–3.72(4H,m), 3.99(3H,s), 6.03(2H,s), 6.13(2H,s), 7.09(1H,s), 7.41(1H,s), 7.89(1H,s), 8.52(1H,brs), 8.60(2H,brs), 11.34(1H,s).

Example 155
2-[N-[2-(2-Dimethylaminoethylamino)-4,5-dimethoxybenzoyl]amino]-4-[(2-dimethylaminoethyl)aminocarbonyl]-1,3-thiazole trihydrochloride IR(KBr)cm⁻¹: 3030, 1655, 1560, 1538; ¹H-NMR(DMSO-d₆)δ: 2.70–2.90(12H,m), 3.20–3.30(4H,m), 3.60–3.75(4H,m), 3.78(3H,s), 3.91(3H,s), 6.10(3H,brs), 6.46(1H,s), 7.53(1H,s), 7.93(1H,s), 8.32(1H,t), 10.40(1H,brs), 10.90(1H,brs).

Example 156
2-[N-(3-Nitrobenzoyl)amino]-4-[(2-diisopropylaminoethyl)aminocarbonyl]-1,3-thiazole hydrochloride ¹H-NMR(DMSO-d₆)δ: 1.31(6H,d), 1.34(6H,d), 3.20(2H,brs), 3.60–3.68(4H,m), 7.88(1H,dd), 7.99(1H,s), 8.48–8.52(2H,m), 8.94(1H,dd), 9.63(1H,s), 13.21(1H,s).

Example 157
2-[N-(3-Aminobenzoyl)amino]-4-[(2-diisopropylaminoethyl)aminocarbonyl]-1,3-thiazole ¹H-NMR(DMSO-d₆)δ: 0.98(12H,d), 2.51(2H,brs), 2.99(2H,brs), 3.20–3.40(2H,m), 5.37(2H,s), 6.78–6.82(1H,m), 7.14–7.22(3H,m), 7.78(1H,s), 7.82(1H,brs), 12.43(1H,s)

Example 158
2-[N-(3-Formylaminobenzoyl)amino]-4-[(2-diisopropylaminoethyl)aminocarbonyl]-1,3-thiazole ¹H-NMR(DMSO-d₆)δ: 0.99(12H,d), 2.56(2H,brs), 3.00(2H,brs), 3.15–3.35(2H,m), 7.50(1H,d), 7.70–7.91(4H,m), 8.25(1H,s), 8.34(1H,s), 10.40(1H,brs), 12.70(1H,brs)

Example 159
2-[N-(3-Acetylaminobenzoyl)amino]-4-[(2-diisopropylaminoethyl)aminocarbonyl]-1,3-thiazole ¹H-NMR(DMSO-d₆)δ: 1.30(6H,d), 1.33(6H,d), 2.09(3H,s), 3.10–3.25(2H,m), 3.60–3.75(4H,m), 7.47(1H,dd), 7.73–7.80(2H,m), 7.93(1H,s), 8.42(1H,t), 9.48(1H,brs), 10.22(1H,s), 12.71(1H,s).

Example 160
2-[N-(4-Nitrobenzoyl)amino]-4-[(2-diisopropylaminoethyl)aminocarbonyl]-1,3-thiazole hydrochloride ¹H-NMR(DMSO-d₆)δ: 1.23–1.41(12H,m), 3.20(2H,s), 3.51–3.74(4H,m), 8.00(1H,s), 8.26–8.51(5H,m), 9.53–9.76 (1H,m), 13.17(1H,s).

Example 161
2-[N-(4-Aminobenzoyl)amino]-4-[(2-diisopropylaminoethyl)aminocarbonyl]-1,3-thiazole dihydrochloride ¹H-NMR(DMSO-d₆)δ: 1.25–1.47(12H,m), 2.89(2H,s), 3.42–3.75(4H,m), 4.90–5.98(4H,m), 6.87–6.94(2H,m), 7.89 (1H,s), 7.89–7.98(2H,m), 8.41–8.63(1H,m), 10.13(2H,s), 12.43(1H,s).

Example 162
2-[N-(4-Formylaminobenzoyl)amino]-4-[(2-diisopropylaminoethyl)aminocarbonyl]-1,3-thiazole ¹H-NMR(DMSO-d₆)δ: 0.99(6H,d), 1.01(6H,d), 2.15–2.30(2H,m), 2.54(2H,brs), 2.99(2H,brs), 7.74(1H,d), 7.84(1H,brs), 7.89(2H,s), 8.06–8.09(2H,m), 8.36(1H,d), 10.54(1H,s), 12.57(1H,brs).

Example 163
2-[N-(4-Acetylaminobenzoyl)amino]-4-[(2-diisopropylaminoethyl)aminocarbonyl]-1,3-thiazole ¹H-NMR(DMSO-d₆)δ: 0.99(6H,d), 1.03(6H,d), 2.09(3H,s), 2.51(2H,brs), 2.99(2H,brs), 3.15–3.30(2H,m), 7.73(1H,d), 7.79(2H,s), 7.84(1H,brs), 8.03–8.07(2H,m), 10.28(1H,s), 12.53(1H,brs).

Example 164
2-[N-(5-Formylamino-2-hydroxy-4-methoxybenzoyl)amino]-4-[(2-diisopropylaminoethyl)aminocarbonyl]-1,3-thiazole ¹H-NMR(DMSO-d₆)δ: 1.08(6H,d), 1.10(6H,d), 2.50–2.54(2H,m), 2.93–3.02(2H,m), 3.10–3.25(2H,m), 3.75 (3H,s), 6.28(1H,s), 7.37(1H,s), 7.98(1H,s), 8.04(1H,t), 8.09 (1H,s), 8.17(1H,s), 8.77(1H,s), 9.17(1H,s).

Example 165
2-[N-(5-Amino-2-hydroxy-4-methoxybenzoyl)amino]-4-[(2-diisopropylaminoethyl)aminocarbonyl]-1,3-thiazole ¹H-NMR(DMSO-d₆)δ: 1.20(12H,d), 3.05–3.25(2H,m), 3.30–3.50(2H,m), 3.61(2H,brs), 3.70(3H,s), 4.35(1H,brs), 6.66(1H,s), 7.29(1H,s), 7.82(1H,s), 8.66(1H,t), 9.43(2H,brs), 11.75(1H,brs).

Example 166
2-[N-(5-Acetylamino-2-hydroxy-4-methoxybenzoyl)amino]-4[(2-diisopropylaminoethyl)aminocarbonyl]-1,3-thiazole hydrochloride ¹H-NMR(DMSO-d₆)δ: 1.30(6H,d), 1.32(6H,d), 2.06(3H,s), 3.17(2H,brs), 3.50–3.75(4H,m), 3.87(3H,s), 6.83(1H,s), 7.88(1H,s), 8.42(1H,s), 8.70(1H,t), 9.15(1H,s), 9.22(1H,brs), 11.60(1H,brs), 12.15(1H,brs).

Example 167
2-[N-(4,5-Dimethoxy-2-hydroxybenzoyl)-N-methylamino]-4-[(2-diisopropylaminoethyl)aminocarbonyl]-1,3-thiazole ¹H-NMR(CDCl₃)δ: 1.26–1.62(12H,m), 3.14–3.22(2H,m), 3.44–3.69(4H,m), 3.85(3H,s), 3.92(3H,s), 4.04(3H,s), 6.58–6.62(1H,m), 6.93(1H,s), 7.83(1H,s), 9.29(1H,s), 11.15–11.41(1H,m).

Example 168
2-[N-(4,5-Dimethoxy-2-hydroxybenzoyl)amino]-4-[[N-(2-diisopropylaminoethyl)-N-methyl]aminocarbonyl]-1,3-thiazole maleate ¹H-NMR(DMSO-d₆)δ: 1.20–1.40(12H,m), 2.50(3H,s), 3.26(2H,brs), 3.40(2H,brs), 3.60–3.75(4H,m), 3.77(3H,s), 3.83(3H,s), 6.62(2H,s), 7.51(1H,s), 7.56(1H,s), 7.71(1H,brs), 8.70(1H,brs), 12.10(1H,brs).

Example 169
2-[N-(2,5-Dihydroxy-4-methoxybenzoyl)amino]-4-[(2diisopropylaminoethyl)aminocarbonyl]-1,3-thiazole dihydrochloride IR(KBr)cm⁻¹: 3325, 1665, 1609, 1559; ¹H-NMR (DMSO-d₆)δ: 1.31(6H,d), 1.34(6H,d), 3.15(2H,brs), 3.50–3.70(4H,m), 3.77(3H,s), 6.00(2H,brs), 6.77(1H,s), 7.47(1H,s), 7.87(1H,s), 8.71(1H,brs), 9.74(1H,brs), 11.50–11.80(2H,m).

Example 170
2-[N-(2-Methoxy-4-nitrobenzoyl)amino]-4-[(2-diisopropylaminoethyl)aminocarbonyl]-1,3-thiazole ¹H-NMR(CDCl₃)δ: 1.08(12H,d), 2.63–2.76(2H,m), 2.98–3.18(2H,m), 3.39–3.53(2H,m), 4.25(3H,s), 7.72(1H,s), 7.81(1H,s), 7.94–7.97(1H,m), 8.01–8.04(1H,m), 8.50–8.53 (1H,m), 10.95(1H,s).

Example 171
2-[N-(5-Chloro-4-formylamino-2-methoxybenzoyl)amino]-4-[(2-diisopropylaminoethyl)aminocarbonyl]-1,3-thiazole ¹H-NMR(DMSO-d₆)δ: 1.00–1.20(12H,m), 2.93(2H,brs), 3.20–3.50(4H,m), 3.97(3H,s), 7.88(1H,s), 7.90(1H,s), 8.25 (1H,s), 8.35(1H,brs), 8.47(1H,s), 10.18(1H,s), 11.62(1H,s).

Example 172
2-[N-(3-Nitrobenzoyl)amino]-4-[(2-dimethylaminoethyl)aminocarbonyl]-1,3-thiazole hydrochloride ¹H-NMR(DMSO-d₆)δ: 2.55(6H,s), 3.24–3.29(2H,m), 3.56–3.71(2H,m), 7.87(1H,s), 8.03(1H,s), 8.42(1H,s), 8.47–8.53(2H,m), 8.94(1H,dd), 10.30(2H,brs).

Structural formulas and melting points of the compounds obtained in Referential Examples 1–6 and Examples 1–172 are shown in the following tables.

TABLE 1

| Ref. Ex. | R¹ | R² | R³ | R⁴ | R⁵ | D | Melting point (° C.) |
|---|---|---|---|---|---|---|---|
| 1 | 3-MeO | 4-MeO | H | H | H | OEt | 132–134 |
| 2 | 2-MeO | 4-MeO | 5-MeO | H | H | OEt | 229.0–231.0 |
| 3 | 2-MeO | 4-MeO | 5-MeO | H | H | OH | 243.0–245.0 |
| 4 | 3-MeO | 4-MeO | H | Me | H | OEt | |
| 6 | 2-OH | 4-MeO | 5-MeO | H | H | OEt | 211.0–213.0 (acetate) |

Referential Example 5

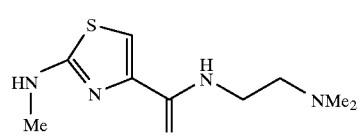

Melting point: 85.7 to 86.7° C.

TABLE 2

[Structure: R¹, R², R³ substituted benzoyl-N(R⁴)-thiazole(R⁵)-C(O)-N(R¹⁰)-(CH₂)ₘ-R¹¹]

| Ex. | R¹ | R² | R³ | R⁴ | R⁵ | R¹⁰ | m | R¹¹ | Melting point (°C.) |
|---|---|---|---|---|---|---|---|---|---|
| 1 | 3-MeO | 4-MeO | H | Me | H | H | 2 | NMe₂ | 196–197 (maleate, decomposed) |
| 2 | 3-MeO | 4-MeO | H | H | H | H | 2 | NH₂ | 272–273 (hydrochloride) |
| 3 | 3-MeO | 4-MeO | H | H | H | H | 2 | NMe₂ | 188–190 (maleate) |
| 4 | 3-MeO | 4-MeO | H | H | H | H | 2 | imidazol-1-yl | 220 (dihydrochloride, decomposed) |
| 5 | 3-MeO | 4-MeO | H | H | H | H | 2 | NEt₂ | 176.5–177.3 |
| 6 | 3-MeO | 4-MeO | H | H | H | H | 2 | N(Pr-i)₂ | 154–155 (maleate) |
| 7 | 3-MeO | 4-MeO | H | H | H | Me | 2 | NMe₂ | 150–154 (fumarate) |
| 8 | 2-MeO | 4-MeO | H | H | H | H | 2 | NMe₂ | 189–191 (maleate) |
| 9 | 2-MeO | 4-MeO | 5-MeO | H | H | H | 2 | NMe₂ | 167–168 (maleate) |
| 10 | 2-MeO | 4-MeO | 5-MeO | H | H | H | 2 | NEt₂ | 154.6–155.2 (maleate) |
| 11 | 2-MeO | 4-MeO | 5-MeO | H | H | H | 2 | N(Pr-i)₂ | 176–178 (maleate, decomposed) |
| 12 | 2-MeO | 4-MeO | 5-MeO | H | H | Me | 2 | N(Pr-i)₂ | 161–162 (maleate) |
| 13 | 2-MeO | 4-MeO | 5-MeO | H | H | H | 2 | N(Me)(Pr-i) | 150–151.0 |
| 14 | 2-MeO | 4-MeO | 5-MeO | H | H | H | 2 | N(Et)(Pr-i) | 174–176 (dihydrochloride, decomposed) |
| 15 | 2-MeO | 4-MeO | 5-MeO | H | H | H | 2 | N(Me)-CH₂-(3,4-diOMe-phenyl) | oil |
| 16 | 2-MeO | 4-MeO | 5-MeO | H | H | H | 2 | N(Pr-i)-CH₂CH₂OH | oil |
| 17 | 2-MeO | 4-MeO | 5-MeO | H | H | H | 2 | isoxazolidin-2-yl | oil |
| 18 | 2-MeO | 4-MeO | 5-MeO | H | H | H | 2 | NH-Pr-i | 159–160 |
| 19 | 2-MeO | 4-MeO | 5-MeO | H | H | H | 2 | N(Pr-i)-COOEt | oil |

TABLE 3

| Ex. | R¹ | R² | R³ | R⁴ | R⁵ | R¹⁰ | m | R¹¹ | Melting point (° C.) |
|---|---|---|---|---|---|---|---|---|---|
| 20 | 2-MeO | 4-MeO | 5-MeO | H | H | H | 2 | —N(Pr-i)CH$_2$COOH | oil |
| 21 | 3-MeO | 4-MeO | H | H | H | H | 3 | NMe$_2$ | 250–252 (fumarate, decomposed) |
| 22 | 3-MeO | 4-MeO | H | H | H | H | 2 | —N(piperazinyl)NH | 181.1–183.3 (maleate) |
| 23 | 3-MeO | 4-MeO | H | H | H | H | 2 | —N(piperazinyl)NMe | 188.2–189.5 (hydrochloride) |
| 24 | 3-MeO | 4-MeO | H | H | H | H | 2 | —N(piperazinyl)N-CH$_2$CH$_2$OH | 196.2–198.5 (trihydrochloride) |
| 25 | 3-MeO | 4-MeO | H | H | H | H | 2 | —N=C(S)(NH) (thiazolidin-2-ylidene) | 155–158 |
| 26 | 3-MeO | 4-MeO | H | H | H | H | 2 | —N=C (pyrrolidin-2-ylidene) | 215–220 (hydroiodide) |
| 27 | 3-MeO | 4-MeO | H | H | H | H | 2 | —N=C(O)(NH) (oxazolidin-2-ylidene) | 190–210 (decomposed) |
| 28 | 3-MeO | 4-MeO | H | H | H | H | 2 | —N=C(NH)(NH) (imidazolidin-2-ylidene) | 190–200 (hydrochloride, decomposed) |
| 29 | 3-MeO | 4-MeO | H | H | H | H | 4 | NMe$_2$ | 174–176 (dihydrochloride) |

TABLE 4

| Ex. | R¹ | R² | R³ | R⁴ | R⁵ | D | Melting point (° C.) |
|---|---|---|---|---|---|---|---|
| 30 | 2-MeO | 4-MeO | 5-MeO | H | H | —O-CH$_2$CH$_2$-NMe$_2$ | 188–189 |
| 31 | 2-MeO | 4-MeO | 5-MeO | H | H | —O-CH$_2$CH$_2$-NEt$_2$ | 186–187 |

TABLE 4-continued

Structure: R¹, R², R³-substituted benzoyl-N(R⁴)-thiazole(R⁵)-C(=O)-D

| Ex. | R¹ | R² | R³ | R⁴ | R⁵ | D | Melting point (° C.) |
|---|---|---|---|---|---|---|---|
| 32 | 2-MeO | 4-MeO | 5-MeO | H | H | —O-CH₂CH₂-N(Pr-i)(Pr-i) | 225–227 |
| 33 | 3-MeO | 4-MeO | H | H | H | —O-CH₂CH₂-NMe₂ | 160–163 |

TABLE 5

Structure: R¹,R²,R³-substituted benzoyl-N(R⁴)-thiazole(R⁵)-C(=O)-N(R¹⁰)-(CH₂)ₘ-R¹¹

| Ex. | R¹ | R² | R³ | R⁴ | R⁵ | R¹⁰ | m | R¹¹ | Melting point (° C.) |
|---|---|---|---|---|---|---|---|---|---|
| 34 | 2-NH₂ | 4-MeO | 5-MeO | H | H | H | 2 | NMe₂ | 181–184 (dihydrochloride, decomposed) |
| 35 | 2-NO₂ | 4-MeO | 5-MeO | H | H | H | 2 | NMe₂ | 213–215 |
| 36 | 2-Br | 4-MeO | 5-MeO | H | H | H | 2 | NMe₂ | 206–209 (decomposed) |
| 37 | 2-OH | 4-MeO | 5-MeO | H | H | H | 2 | NMe₂ | 219–222 |
| 38 | 2-OH | 4-MeO | 5-MeO | H | H | H | 2 | —N(Pr-i)(Pr-i) | 179–182 (decomposed) / 160 (hydrochloride) |
| 39 | 2-NMe₂ | 4-MeO | 5-MeO | H | H | H | 2 | NMe₂ | 242–244 (dihydrochloride, decomposed) |
| 40 | 2-Me | 4-MeO | 5-MeO | H | H | H | 2 | NMe₂ | 182–185 (decomposed) |
| 41 | 2-NHAc | 4-MeO | 5-MeO | H | H | H | 2 | NMe₂ | 111–113 (decomposed) |
| 42 | H | H | H | H | H | H | 2 | NMe₂ | 94.0 (hydrochloride) |
| 43 | 2-MeO | H | H | H | H | H | 2 | NMe₂ | 143–144 (maleate) |
| 44 | 3-MeO | H | H | H | H | H | 2 | NMe₂ | 207–208.0 (dihydrochloride) |
| 45 | 3-Cl | H | H | H | H | H | 2 | NMe₂ | 176–179 (maleate) |
| 46 | 4-MeO | H | H | H | H | H | 2 | NMe₂ | 208.5–209 (dihydrochloride) |
| 47 | 2-MeO | 3-MeO | H | H | H | H | 2 | NMe₂ | 182–184 (maleate) |
| 48 | 2-OH | 3-MeO | H | H | H | H | 2 | NMe₂ | 188 (maleate) |
| 49 | 2-MeO | 4-OH | H | H | H | H | 2 | —N(Pr-i)(Pr-i) | 220–225 (dihydrochloride) |
| 50 | 2-OH | 4-MeO | H | H | H | H | 2 | —N(Pr-i)(Pr-i) | 135–148 |
| 51 | 2-MeO | 5-MeO | H | H | H | H | 2 | NMe₂ | 166 (maleate) |
| 52 | 2-MeO | 6-MeO | H | H | H | H | 2 | NMe₂ | 205 (maleate) |
| 53 | 3-MeO | 5-MeO | H | H | H | H | 2 | NMe₂ | 149–150 (hydrochloride) |
| 54 | 3-MeO | 4-MeO | H | H | H | H | 2 | NHMe | 208–212 (dihydrochloride) |
| 55 | 3-MeO | 4-MeO | H | H | H | Me | 2 | NHMe | 168–172 (dihydrochloride) |
| 56 | 3-MeO | 4-MeO | H | H | H | H | 2 | NH-iPr | 108–110 (maleate) |
| 57 | 4-OH | 3-MeO | H | H | H | H | 2 | —N(Pr-i)(Pr-i) | 130–145 (dihydrochloride) |

TABLE 5-continued

[Structure: R¹, R², R³ substituents on benzene ring connected via C(=O)-N(R⁴)- to thiazole (with R⁵) which has C(=O)-N(R¹⁰)-(CH₂)ₘ-R¹¹ group]

| Ex. | R¹ | R² | R³ | R⁴ | R⁵ | R¹⁰ | m | R¹¹ | Melting point (° C.) |
|-----|------|------|---|----|----|-----|---|-----|----------------------|
| 58 | 3-OH | 4-MeO | H | H | H | H | 2 | —N(Pr-i)₂ | 150–160 (dihydrochloride) |
| 59 | 3-MeO | 4-MeO | H | H | H | H | 2 | —NH-(2-pyridyl) | 170–175 (hydrochloride) |

TABLE 6

| Ex. | R¹ | R² | R³ | R⁴ | R⁵ | R¹⁰ | m | R¹¹ | Melting point (° C.) |
|-----|------|------|------|----|----|-----|---|-----|----------------------|
| 60 | 3-MeO | 4-MeO | H | H | H | H | 2 | pyrrolidin-1-yl | 88–90 (maleate) |
| 61 | 3-MeO | 4-MeO | H | H | H | H | 2 | piperidin-1-yl | 233–235 (dihydrochloride) |
| 62 | 3-MeO | 4-MeO | H | H | H | H | 2 | 2-oxopyrrolidin-1-yl | 197–200 |
| 63 | 3-MeO | 4-MeO | H | H | H | H | 2 | 2-oxopiperidin-1-yl | 192–194 |
| 64 | 3-MeO | 4-MeO | H | H | H | H | 2 | —N=C(NH₂)₂ | 225 (hydrochloride) |
| 65 | 3-MeO | 4-MeO | H | H | H | H | 2 | —N=C(SH)(NHMe) | 213–216 (dihydrochloride) |
| 66 | 3-MeO | 4-MeO | H | H | H | H | 2 | —N=C(SMe)(NHMe) | 161–163 (dihydrochloride) |
| 67 | 2-MeO | 3-MeO | 4-MeO | H | H | H | 2 | NMe₂ | 148–150 (maleate) |
| 68 | 2-MeO | 3-MeO | 5-MeO | H | H | H | 2 | NMe₂ | 164–166 (maleate) |
| 69 | 2-MeO | 3-MeO | 6-MeO | H | H | H | 2 | NMe₂ | 175–176.5 (maleate) |
| 70 | 2-MeO | 4-MeO | 6-MeO | H | H | H | 2 | NMe₂ | 91–93 (maleate) |
| 71 | 3-MeO | 4-MeO | 5-MeO | H | H | H | 2 | NMe₂ | 226–228 (fumarate) |

TABLE 6-continued

| Ex. | R¹ | R² | R³ | R⁴ | R⁵ | R¹⁰ | m | R¹¹ | Melting point (° C.) |
|---|---|---|---|---|---|---|---|---|---|
| 72 | 2-MeO | 4-MeO | 5-MeO | H | H | H | 2 | —NH-cyclopropyl | 143–144 |
| 73 | 2-MeO | 4-MeO | 5-MeO | H | H | H | 2 | NH-tBu | 196–197 (dihydrochloride) |
| 74 | 2-MeO | 4-MeO | 5-MeO | H | H | H | 3 | —N(Pr-i)₂ | 176–178 (dihydrochloride) |
| 75 | 2-MeO | 4-MeO | 5-MeO | H | H | Me | 2 | NEt₂ | 100–101 (maleate) |
| 76 | 2-MeO | 4-MeO | 5-MeO | Me | H | H | 2 | NMe₂ | 115.5–117.0 (maleate) |
| 77 | 2-MeO | 4-MeO | 5-MeO | Me | H | H | 2 | —N(Pr-i)₂ | 176–177.5 (maleate) |
| 78 | 2-MeO | 4-MeO | 5-MeO | H | H | H | 2 | —N(Pr-n)₂ | 148–150 (dihydrochloride) |
| 79 | 2-MeO | 4-MeO | 5-MeO | H | H | H | 2 | —N(Bu-n)₂ | 163–165 (dihydrochloride) |

TABLE 7

| Ex. | R¹ | R² | R³ | R⁴ | R⁵ | R¹⁰ | m | R¹¹ | Melting point (° C.) |
|---|---|---|---|---|---|---|---|---|---|
| 80 | 2-MeO | 4-MeO | 5-MeO | H | H | H | 2 | —N(Bu-i)₂ | 185–187 (hydrochloride) |
| 81 | 2-MeO | 4-MeO | 5-MeO | H | H | H | 2 | —N(dicyclohexyl) | 128–129 |
| 82 | 2-MeO | 4-MeO | 5-MeO | H | H | H | 2 | NMeEt | 163.0–165 |
| 83 | 2-MeO | 4-MeO | 5-MeO | H | H | H | 2 | —N(Pr-i)(Pr-n) | 178–179 (dihydrochloride) |
| 84 | 2-MeO | 4-MeO | 5-MeO | H | H | H | 2 | —N(Pr-i)(Bu-n) | 203–205 (dihydrochloride) |
| 85 | 2-MeO | 4-MeO | 5-MeO | H | Cl | H | 2 | —N(Pr-i)₂ | 189–191 (dihydrochloride) |
| 86 | 2-MeO | 4-MeO | 5-MeO | H | Me | H | 2 | —N(Pr-i)₂ | 187–189 (dihydrochloride) |
| 87 | 2-MeO | 4-MeO | 5-MeO | H | H | H | 2 | —N(Me)(O—Me) | 128–129 |
| 88 | 2-MeO | 4-MeO | 5-MeO | H | H | H | 2 | —N(Pr-i)(CH₂CH₂O-Me) | 182–184 (dihydrochloride) |

TABLE 7-continued

| Ex. | R¹ | R² | R³ | R⁴ | R⁵ | R¹⁰ | m | R¹¹ | Melting point (° C.) |
|---|---|---|---|---|---|---|---|---|---|
| 89 | 2-MeO | 4-MeO | 5-MeO | H | H | H | 2 | —N(Me)CH₂CH₂N(Me)Me | 179–181 (dimaleate) |
| 90 | 2-MeO | 4-MeO | 5-MeO | H | H | H | 2 | —N(Pr-i)CH₂-(3,4-dimethoxyphenyl) | 150–152 |
| 91 | 2-MeO | 4-MeO | 5-MeO | H | H | H | 2 | —N(Pr-i)CH₂CH₂-(3,4-dimethoxyphenyl) | 148–150 (hydrochloride) |
| 92 | 2-EtO | 4-MeO | 5-MeO | H | H | H | 2 | NMe₂ | 186–188 |
| 93 | 2-iPro | 4-MeO | 5-MeO | H | H | H | 2 | NMe₂ | 171–172 |
| 94 | 2-MeO | 4-EtO | 5-EtO | H | H | H | 2 | —N(Pr-i)(Pr-i) | 145–147 (fumarate) |
| 95 | 2-BnO | 4-MeO | 5-MeO | H | H | H | 2 | NMe₂ | 183–185 |
| 96 | 2-OH | 4-MeO | 5-MeO | H | H | H | 2 | NH-iPr | 208–209 (dihydrochloride) |
| 97 | 2-OH | 4-MeO | 5-MeO | H | H | H | 2 | —N(Me)(Pr-i) | 185–186 (dihydrochloride) |

TABLE 8

| Ex. | R¹ | R² | R³ | R⁴ | R⁵ | R¹⁰ | m | R¹¹ | Melting point (° C.) |
|---|---|---|---|---|---|---|---|---|---|
| 98 | 2-OH | 4-MeO | 5-MeO | H | H | H | 2 | —N(Et)(Pr-i) | 186–187 (dihydrochloride) |
| 99 | 2-OH | 4-MeO | 5-MeO | H | H | H | 2 | —N(Pr-n)(Pr-i) | 201–202 (dihydrochloride) |
| 100 | 2-MeO | 4-OH | 5-MeO | H | H | H | 2 | NMe₂ | 207–209 (maleate) |
| 101 | 2-MeO | 4-OH | 5-MeO | H | H | H | 2 | NH-iPr | 250–252 (hydrochloride) |
| 102 | 2-MeO | 4-OH | 5-MeO | H | H | H | 2 | —N(Me)(Pr-i) | 193–195 (hydrochloride) |
| 103 | 2-MeO | 4-OH | 5-MeO | H | H | H | 2 | —N(Et)(Pr-i) | 158–160 (hydrochloride) |
| 104 | 2-MeO | 4-OH | 5-MeO | H | H | H | 2 | —N(Pr-i)(Pr-i) | 166.5–168.5 (maleate) |
| 105 | 2-MeO | 4-OH | 5-MeO | H | H | H | 2 | —N(Pr-n)(Pr-i) | 118–121 (dihydrochloride) |

TABLE 8-continued

| Ex. | R$^1$ | R$^2$ | R$^3$ | R$^4$ | R$^5$ | R$^{10}$ | m | R$^{11}$ | Melting point (° C.) |
|---|---|---|---|---|---|---|---|---|---|
| 106 | 2-MeO | 4-MeO | 5-OH | H | H | H | 2 | —N(Pr-i)$_2$ | 191.5–193.5 (maleate) |
| 107 | 2-MeO | 4-OH | 5-OH | H | H | H | 2 | —N(Pr-i)$_2$ | 253–255.5 (hydrochloride) |
| 108 | 2-OH | 4-OH | 5-MeO | H | H | H | 2 | —N(Pr-i)$_2$ | 194–196 (dihydrochloride) |
| 109 | 2-AcO | 4-MeO | 5-MeO | H | H | H | 2 | —N(Pr-i)$_2$ | 222.5–223.0 (hydrochloride) |
| 110 | 2-Cl | 4-MeO | 5-MeO | H | H | H | 2 | NMe$_2$ | 159–162 (dihydrochloride) |
| 111 | 2-Cl | 4-MeO | 5-MeO | H | H | H | 2 | —N(Pr-i)$_2$ | 146–159 (dihydrochloride) |
| 112 | 2-Br | 4-MeO | 5-MeO | H | H | H | 2 | —N(Pr-i)$_2$ | 190–195 (dihydrochloride) |
| 113 | 2-NO$_2$ | 4-MeO | 5-MeO | H | H | H | 2 | —N(Pr-i)$_2$ | 196–197 |
| 114 | 2-NH$_2$ | 4-MeO | 5-MeO | H | H | H | 2 | —N(Pr-i)$_2$ | 184–186 (dihydrochloride) |
| 115 | 2-F | 4-MeO | 5-MeO | H | H | H | 2 | —N(Pr-i)$_2$ | 171–172 (maleate) |

TABLE 9

| Ex. | R$^1$ | R$^2$ | R$^3$ | R$^4$ | R$^5$ | R$^{10}$ | m | R$^{11}$ | Melting point (° C.) |
|---|---|---|---|---|---|---|---|---|---|
| 116 | 2-MeO | 4-NH$_2$ | 5-MeO | H | H | H | 2 | —N(Pr-i)$_2$ | 93–102 (fumarate) |
| 117 | 2-MeO | 4-NHCHO | 5-MeO | H | H | H | 2 | —N(Pr-i)$_2$ | 199–201 |
| 118 | 2-MeO | 4-NHAc | 5-MeO | H | H | H | 2 | —N(Pr-i)$_2$ | 183–185 (hydrochloride) |
| 119 | 2-MeO | 4-NO$_2$ | 5-MeO | H | H | H | 2 | —N(Pr-i)$_2$ | 206–208 (hydrochloride) |
| 120 | 2-MeO | 4-Br | 5-MeO | H | H | H | 2 | —N(Pr-i)$_2$ | 238–240 (hydrochloride) |

TABLE 9-continued

| Ex. | R¹ | R² | R³ | R⁴ | R⁵ | R¹⁰ | m | R¹¹ | Melting point (° C.) |
|---|---|---|---|---|---|---|---|---|---|
| 121 | 2-OH | 4-Br | 5-MeO | H | H | H | 2 | 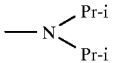 | 185–187 (hydrochloride) |
| 122 | 2-MeO | 4-Cl | 5-Cl | H | H | H | 2 | 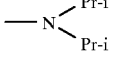 | 213–214 (hydrochloride) |
| 123 | 2-OH | 4-Cl | 5-Cl | H | H | H | 2 | 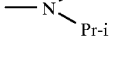 | 157–158 (hydrochloride) |
| 124 | 2-MeO | 4-NH₂ | 5-Cl | H | H | H | 2 | NMe₂ | 213.5–214.0 (maleate) |
| 125 | 2-MeO | 4-NH₂ | 5-Cl | H | H | H | 2 | 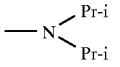 | 175–176.5 (dihydrochloride) |
| 126 | 2-MeO | 4-NHAc | 5-Cl | H | H | H | 2 | 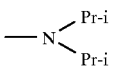 | 230–232 (hydrochloride) |
| 127 | 2-MeO | 4-MeO | 5-MeO | H | H | H | 2 | 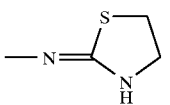 | 232–235 |
| 128 | 2-MeO | 4-MeO | 5-MeO | H | H | H | 2 | 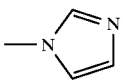 | 184–185 |
| 129 | 2-OH | 4-NH₂ | 5-MeO | H | H | H | 2 | 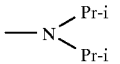 | 173–175 |
| 130 | 2-OH | 4-NHCHO | 5-MeO | H | H | H | 2 | 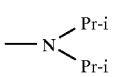 | 209–213 (dihydrochloride) |
| 131 | 2-MeO | 4-Me | 5-NO₂ | H | H | H | 2 | 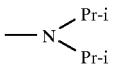 | 272–275 (dihydrochloride) |

TABLE 10

| Ex. | R₁ | R² | R³ | R⁴ | R⁵ | R¹⁰ | m | R¹¹ | Melting point (° C.) |
|---|---|---|---|---|---|---|---|---|---|
| 132 | 2-MeO | 4-MeO | 5-NO₂ | H | H | H | 2 | 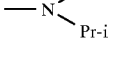 | 169–174 (hydrochloride) |
| 133 | 2-MeO | 4-MeO | 5-NH₂ | H | H | H | 2 | 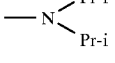 | 207–209 (dihydrochloride) |
| 134 | 2-MeO | 4-MeO | 5-NHCHO | H | H | H | 2 | 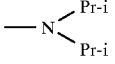 | 163–170 (hydrochloride) |
| 135 | 2-MeO | 4-MeO | 5-NHAc | H | H | H | 2 | 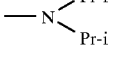 | 175–177 |

TABLE 10-continued

| Ex. | R1 | R2 | R3 | R4 | R5 | R10 | m | R11 | Melting point (°C.) |
|---|---|---|---|---|---|---|---|---|---|
| 136 | 3-NO$_2$ | 4-MeO | H | H | H | H | 2 | —N(Pr-i)$_2$ | 156–158 (hydrochloride) |
| 137 | 3-NH$_2$ | 4-MeO | H | H | H | H | 2 | —N(Pr-i)$_2$ | 223–224 (dihydrochloride) |
| 138 | 3-NHCHO | 4-MeO | H | H | H | H | 2 | —N(Pr-i)$_2$ | 175 |
| 139 | 3-NHAc | 4-MeO | H | H | H | H | 2 | —N(Pr-i)$_2$ | 185–187 (hydrochloride) |
| 140 | 3-MeO | 4-NO$_2$ | H | H | H | H | 2 | —N(Pr-i)$_2$ | 148–150 (hydrochloride) |
| 141 | 3-MeO | 4-NH$_2$ | H | H | H | H | 2 | —N(Pr-i)$_2$ | 166–168 (dihydrochloride) |
| 142 | 3-MeO | 4-NHCHO | H | H | H | H | 2 | —N(Pr-i)$_2$ | 235–236 (fumarate) |
| 143 | 3-MeO | 4-NHAc | H | H | H | H | 2 | —N(Pr-i)$_2$ | 186–188 (hydrochloride) |
| 144 | 2-MeO | 4-NH$_2$ | H | H | H | H | 2 | —N(Pr-i)$_2$ | 179–181 |
| 145 | 2-MeO | 4-NHCHO | H | H | H | H | 2 | —N(Pr-i)$_2$ | 211–214 |
| 146 | 2-MeO | 4-NHAc | H | H | H | H | 2 | —N(Pr-i)$_2$ | 82–88 (dihydrochloride) |

TABLE 11

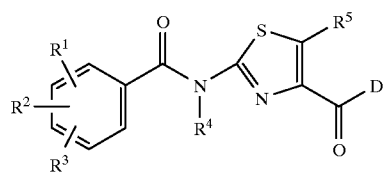

| Ex. | R1 | R2 | R3 | R4 | R5 | D | Melting point (°C.) |
|---|---|---|---|---|---|---|---|
| 147 | 3-MeO | 4-MeO | H | H | H | 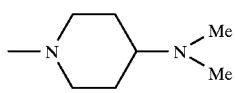 | 174–177 |

TABLE 11-continued
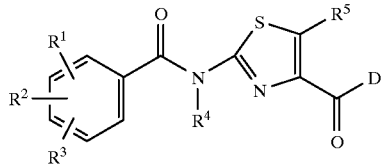
| Ex. | R¹ | R² | R³ | R⁴ | R⁵ | D | Melting point (° C.) |
|---|---|---|---|---|---|---|---|
| 148 | 3-MeO | 4-MeO | H | H | H | 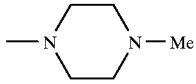 | 200–202 |
| 149 | 2-MeO | 4-MeO | 5-MeO | H | H | 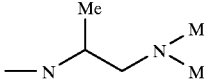 | 138.5–140 (maleate) |
| 150 | 2-MeO | 4-MeO | 5-MeO | H | H | 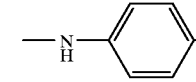 | 230–232 |
| 151 | 2-MeO | 4-MeO | 5-MeO | H | H | 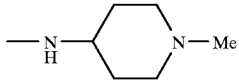 | 116–118 |
| 152 | 2-MeO | 4-MeO | 5-MeO | H | H | 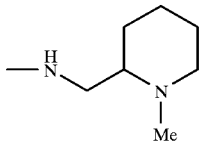 | powder (dihydrochloride) |
| 153 | 2-OH | 4-MeO | 5-MeO | H | H | 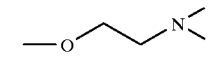 | 120 (hydrochloride) |
TABLE 12
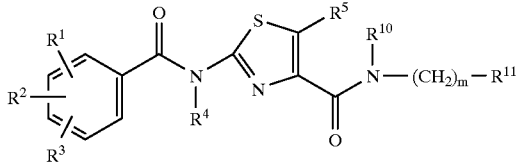
| Ex. | R¹ | R² | R³ | R⁴ | R⁵ | R¹⁰ | m | R¹¹ | Melting point (° C.) |
|---|---|---|---|---|---|---|---|---|---|
| 154 | 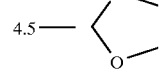 4,5— | | 2-OMe | H | H | H | 2 | 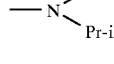 | 192–195 (maleate) |
| 155 | * | 4-OMe | 5-OMe | H | H | H | 2 | 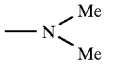 | 187–190 (trihydrochloride) |
| 156 | 3-NO₂ | H | H | H | H | H | 2 | 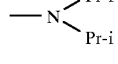 | 174–175 (hydrochloride) |

TABLE 12-continued

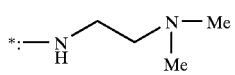

| Ex. | R¹ | R² | R³ | R⁴ | R⁵ | R¹⁰ | m | R¹¹ | Melting point (° C.) |
|---|---|---|---|---|---|---|---|---|---|
| 157 | 3-NH₂ | H | H | H | H | H | 2 | —N(Pr-i)(Pr-i) | 164–165 |
| 158 | 3-NHCHO | H | H | H | H | H | 2 | —N(Pr-i)(Pr-i) | 201–202 |
| 159 | 3-NHAc | H | H | H | H | H | 2 | —N(Pr-i)(Pr-i) | 128–130 |
| 160 | 4-NO₂ | H | H | H | H | H | 2 | —N(Pr-i)(Pr-i) | 175–179 (hydrochloride) |
| 161 | 4-NH₂ | H | H | H | H | H | 2 | —N(Pr-i)(Pr-i) | 189–194 (dihydrochloride) |
| 162 | 4-NHCHO | H | H | H | H | H | 2 | —N(Pr-i)(Pr-i) | 155–156 |
| 163 | 4-NHAc | H | H | H | H | H | 2 | —N(Pr-i)(Pr-i) | 175–177 |
| 164 | 2-OH | 4-MeO | 5-NHCHO | H | H | H | 2 | —N(Pr-i)(Pr-i) | 222–223 |
| 165 | 2-OH | 4-MeO | 5-NH₂ | H | H | H | 2 | —N(Pr-i)(Pr-i) | oil |

*: —NH—CH₂CH₂—N(Me)(Me)

TABLE 13

| Ex. | R¹ | R² | R³ | R⁴ | R⁵ | R¹⁰ | m | R¹¹ | Melting point (° C.) |
|---|---|---|---|---|---|---|---|---|---|
| 166 | 2-OH | 4-MeO | 5-NHAc | H | H | H | 2 | —N(Pr-i)(Pr-i) | 198.5–200.5 (hydrochloride) |
| 167 | 2-OH | 4-MeO | 5-MeO | Me | H | H | 2 | —N(Pr-i)(Pr-i) | 87–90 |

TABLE 13-continued

| Ex. | R¹ | R² | R³ | R⁴ | R⁵ | R¹⁰ | m | R¹¹ | Melting point (° C.) |
|---|---|---|---|---|---|---|---|---|---|
| 168 | 2-OH | 4-MeO | 5-MeO | H | H | Me | 2 | —N(Pr-i)(Pr-i) | 188–190 (maleate) |
| 169 | 2-OH | 4-MeO | 5-OH | H | H | H | 2 | —N(Pr-i)(Pr-i) | 189–191 (dihydrochloride) |
| 170 | 2-MeO | 4-NO₂ | H | H | H | H | 2 | —N(Pr-i)(Pr-i) | 158–160 |
| 171 | 2-MeO | 4-NHCHO | 5-Cl | H | H | H | 2 | —N(Pr-i)(Pr-i) | 222.0–223.0 |
| 172 | 3-NO₂ | H | H | H | H | H | 2 | —N(Me)(Me) | 239.5–240.5 (hydrochloride) |

Preparation Example 1

| | |
|---|---|
| Compound of Example 2 | 20 g |
| Lactose | 315 g |
| Corn starch | 125 g |
| Crystalline cellulose | 25 g |

The above-described ingredients were uniformly mixed, followed by the addition of 200 ml of a 7.5% aqueous hydroxypropylcellulose solution. The resulting mixture was pulverized into granules through a screen of 0.5 mm in diameter by an extrusion granulator. Immediately after that, the resultant granules were rounded by a Marumerizer, followed by drying, whereby a granular agent was obtained.

Preparation Example 2

| | |
|---|---|
| Compound of Example 24 | 20 g |
| Lactose | 100 g |
| Corn starch | 36 g |
| Crystalline cellulose | 30 g |
| Carboxymethyl cellulose calcium | 10 g |
| Magnesium stearate | 4 g |

The above-described ingredients were uniformly mixed. The resulting mixture was pressed into 200-mg tablets by a punch of 7.5 mm in diameter on a single punch tableting machine.

Preparation Example 3

| | |
|---|---|
| Compound of Example 30 | 100 mg |
| Sodium acetate | 2 mg |
| Acetic acid (for adjusting pH to 5.8) | q.s. |
| Distilled water | q.s. |
| Total | 10 ml/vial |

According to the above formulation, an injection was prepared in a manner known per se in the art.

CAPABILITY OF EXPLOITATION IN INDUSTRY

The compound according to the present invention markedly enhances gastrointestinal motility, thereby bringing about an improvement in the digestive dysmotility and at the same time, exhibits high safety so that it is useful for the prevention and treatment of various digestive dysmotility.

We claim:

1. An aminothiazole derivative represented by the following formula (Ia), or a salt thereof:

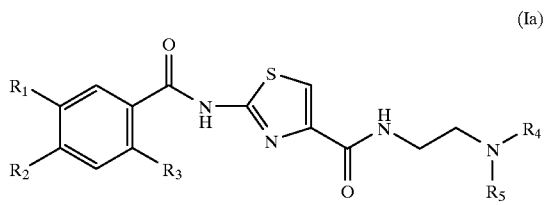

(Ia)

wherein $R_1$, $R_2$ and $R_3$ are the same or different and each independently represents a hydroxy group or a methoxy group; and $R_4$ and $R_5$ are the same or different and each independently represents a hydrogen atom, an ethyl group, n-Pr or iso-Pr, with the exception that $R_4$ and $R_5$ are not both hydrogen.

2. The aminothiazole derivative, or a salt thereof, according to claim 1, wherein $R_4$ and $R_5$ are the same or different and each independently represents a hydrogen atom, an ethyl group or iso-Pr, with the exception that $R_4$ and $R_5$ are not both hydrogen.

3. The aminothiazole derivative, or a salt thereof, according to claim 1, wherein said derivative is selected from the group consisting of compound nos. 10, 11, 14, 18, 38, 78, 83, 96, 98, 103, 104, 106, 107 and 169 of the following Table, wherein $R_1$–$R_5$ are in reference to said formula (Ia):

TABLE

| | R₁ | R₂ | R₃ | R₄ | R₅ |
|---|---|---|---|---|---|
| Compound 10 | OMe | OMe | OMe | Et | Et |
| Compound 11 | OMe | OMe | OMe | i-Pr | i-Pr |

TABLE-continued

| | R₁ | R₂ | R₃ | R₄ | R₅ |
|---|---|---|---|---|---|
| Compound 14 | OMe | OMe | OMe | Et | i-Pr |
| Compound 18 | OMe | OMe | OMe | i-Pr | H |
| Compound 38 | OMe | OMe | OH | i-Pr | i-Pr |
| Compound 78 | OMe | OMe | OMe | n-Pr | n-Pr |
| Compound 83 | OMe | OMe | OMe | i-Pr | n-Pr |
| Compound 96 | OMe | OMe | OH | H | i-Pr |
| Compound 98 | OMe | OMe | OH | Et | i-Pr |
| Compound 103 | OMe | OH | OMe | Et | i-Pr |
| Compound 104 | OMe | OH | OMe | i-Pr | i-Pr |
| Compound 106 | OH | OMe | OMe | i-Pr | i-Pr |
| Compound 107 | OH | OH | OMe | i-Pr | i-Pr |
| Compound 169 | OH | OMe | OH | i-Pr | i-Pr |

4. The aminothiazole derivative, or a salt thereof, according to claim 3, wherein said derivative is selected from the group consisting of compound Nos. 10, 11, 14, 18, 38, 103, 104 and 107 of said Table.

5. The aminothiazole derivative, or a salt thereof, according to claim 4, wherein said derivative is compound No. 38 of said Table.

6. A pharmaceutical composition comprising an aminothiazole derivative (Ia) or a salt thereof as claimed in claim 1, and a pharmaceutically acceptable carrier.

7. A pharmaceutical composition comprising an aminothiazole derivative (Ia) or a salt thereof as claimed in claim 2, and a pharmaceutically acceptable carrier.

8. A pharmaceutical composition comprising an aminothiazole derivative (Ia) or a salt thereof as claimed in claim 3, and a pharmaceutically acceptable carrier.

9. A pharmaceutical composition comprising an aminothiazole derivative (Ia) or a salt thereof as claimed in claim 4, and a pharmaceutically acceptable carrier.

10. A pharmaceutical composition comprising an aminothiazole derivative (Ia) or a salt thereof as claimed in claim 5, and a pharmaceutically acceptable carrier.

11. A method for the prevention and treatment of diseases caused by digestive dysmotility, which comprises administering, to a patient, an effective dose of an aminothiazole derivative represented by the following formula (I), or a salt thereof:

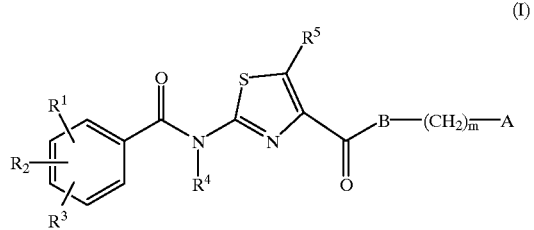

wherein $R^1$, $R^2$ and $R^3$ are the same or different and each independently represents a hydrogen atom, a hydroxy group, a lower alkyl group, a lower alkoxy group, a lower alkylcarbonyloxy group, a halogen atom, a nitro group, an amino group, a mono- or di-(lower alkyl)amino group, a mono- or di-(lower alkyl)carbonylamino group, a formylamino group or a mono- or di-(lower alkyl)aminoalkylamino group, or $R^1$ and $R^2$ may be coupled together to form a methylenedioxy group; $R^4$ represents a hydrogen atom or a lower alkyl group; $R^5$ represents a hydrogen atom, a halogen atom or a lower alkyl group; A represents a group represented by the following formula:

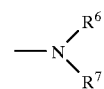

wherein $R^6$ and $R^7$ are the same or different and each independently represents a hydrogen atom, a lower alkyl group, a lower alkoxy group, a hydroxy(lower alkyl) group, a carboxy(lower alkyl) group, a lower alkoxycarbonyl (lower alkyl) group, a lower alkoxyalkyl group, a mono- or di-(lower alkyl)aminoalkyl group, a phenylalkyl group which may be substituted with one or two lower alkoxy groups on the benzene ring, a saturated or unsaturated nitrogen-containing heterocyclic group which may be substituted by a lower alkyl group, or $R^6$ and $R^7$, together with an adjacent nitrogen atom, form a saturated or unsaturated nitrogen-containing heterocyclic group which may be substituted by an oxo group (O=) or 1 to 3 lower alkyl or hydroxy (lower alkyl) groups, or a group represented by the following formula:

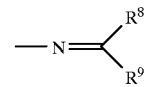

wherein $R^8$ and $R^9$ are the same or different and each independently represents an amino group, a mono- or di-(lower alkyl)amino group, a mercapto group or a lower alkylthio group, or $R^8$ and $R^9$ form, together with an adjacent carbon atom, a nitrogen-containing heterocyclic group; and B represents an imino group which may be substituted by a lower alkyl group or an oxygen atom; and m stands for an integer of 0 to 4; B—$(CH_2)_m$—A may form a piperidinyl, branched alkylamino or phenylamino group which may be substituted by a mono- or di-(lower alkyl) amino group, or a piperazinyl, piperidinylamino or piperidinylalkylamino group which may be substituted by a lower alkyl group.

12. A method according to claim 11, wherein the diseases caused by digestive dysmotility are epigastric dyscomfort, nausea, vomiting, heart burn, anorexia, epigastric pain, abdominal flatulence, chronic gastritis, reflux esophagitis and postgastrectomy syndrome.

* * * * *